(12) United States Patent
Fettelschoss et al.

(10) Patent No.: US 11,207,390 B2
(45) Date of Patent: Dec. 28, 2021

(54) TREATMENT OF PRURITUS IN HORSES

(71) Applicants: UNIVERSITÄT ZÜRICH, Zürich (CH); UNIVERSITÄT BERN, Bern (CH); EVAX AG, Münchwilen (CH)

(72) Inventors: Antonia Fettelschoss, Münchwilen Thurgau (CH); Victoria Fettelschoss, Lenzburg (CH); Martin Bachmann, Rämismühle (CH)

(73) Assignees: UNIVERSITÄT ZÜRICH, Zürich (CH); EVAX AG, Münchwilen (CH); UNIVERSITÄT BERN, Bern (CH)

( * ) Notice: Subject to any disclaimer, the term of this patent is extended or adjusted under 35 U.S.C. 154(b) by 0 days.

(21) Appl. No.: 16/491,514

(22) PCT Filed: Mar. 7, 2018

(86) PCT No.: PCT/EP2018/055644
§ 371 (c)(1),
(2) Date: Sep. 5, 2019

(87) PCT Pub. No.: WO2018/162577
PCT Pub. Date: Sep. 13, 2018

(65) Prior Publication Data
US 2020/0016248 A1    Jan. 16, 2020

(30) Foreign Application Priority Data
Mar. 7, 2017    (EP) ..................................... 17159644

(51) Int. Cl.
*A61K 39/00*    (2006.01)
*A61P 17/04*    (2006.01)

(52) U.S. Cl.
CPC .......... *A61K 39/0005* (2013.01); *A61P 17/04* (2018.01); *A61K 2039/5256* (2013.01); *A61K 2039/5258* (2013.01); *A61K 2039/552* (2013.01)

(58) Field of Classification Search
None
See application file for complete search history.

(56) References Cited

U.S. PATENT DOCUMENTS 10,093,731 B2 *    10/2018    Li ........................ C07K 16/244
2018/0250388 A1 *    9/2018    Fettelschoss .......... A61K 39/35

FOREIGN PATENT DOCUMENTS

WO    03/040164 A2    5/2003

OTHER PUBLICATIONS

Walker, "Insect Bite Hypersensitivity in Horses," Pub 3564, found at https://www.lsuagcenter.com/profiles/kkramer/articles/page1479765922917 (Year: 2016).*

(Continued)

*Primary Examiner* — M Franco G Salvoza
(74) *Attorney, Agent, or Firm* — Medler Ferro Woodhouse & Mills PLLC

(57) ABSTRACT

The present invention relates to compositions, immunogenic or vaccine compositions and pharmaceutical compositions for the prevention or treatment of a condition or disorder selected from a pruritic condition or an allergic condition, of equine mammals, preferably of horses. Furthermore, the invention provides methods for preventing or treating pruritus, preferably pruritus associated with a pruritic condition or an allergic condition such as allergic dermatitis, of equine mammals, preferably of horses.

16 Claims, 20 Drawing Sheets

Specification includes a Sequence Listing.

(56) References Cited

OTHER PUBLICATIONS

Bernstein, ("Allergy Treatment in Horses" found at http://www.lganimalderm.com/disease-info/allergy-treatment-in-horses (Year: 2016).*

International Search Report issued in International Application No. PCT/EP2018/055644 dated May 25, 2018.

Bachmann et al., "Vaccination against IL-31 for the treatment of atopic dermatitis in dogs," J Allergy Clin Immunol 142:279-281 (2018).

Cunningham et al., "Cloning, expression and biological activity of equine interleukin (IL)-5," Veterinary Immunology and Immunopathology (2003) 95:63-72.

Cunningham et al., "Equine recurrent airway obstruction and insect bite hypersensitivity Understanding the diseases and uncovering possible new therapeutic approaches," The Veterinary Journal 177:334-344 (2008).

Fadok, "Update on Equine Allergies," Vet Clin Equine 29:541-550 (2013).

Fettelschoss-Gabriel, et al., "Treating insect-bite hypersensitivity in horses with active vaccination against IL-5," J Allergy Clin Immunol 142:1194-1205.e3 (2018).

Michels et al., "A blinded, randomized, placebo-controlled, dose determination trial of lokivetmab (ZTS-00103289), a canonized, anti-canine IL-31 monoclonal antibody in client owned dogs with atopic dermatitis," Vet Dermatol 27:478-e129 (2016).

Plummer et al., "Viral nanoparticles and virus-like particles: platforms for contemporary vaccine design," WIREs Nanomedicine and Nanobiotechnology 3:174-196 (2011).

Sonkoly et al., "IL-31: A new link between T cells and pruritus in atopic skin inflammation," J Allergy Clin Immunol 117:411-417 (2006).

Zou et al., "Combined vaccination against IL-5 and eotaxin blocks eosinophilia in mice," Vaccine 28:3192-3200 (2010).

* cited by examiner

SEQUENCE LISTING

```
<160> NUMBER OF SEQ ID NOS: 31

<210> SEQ ID NO 1
<211> LENGTH: 123
<212> TYPE: PRT
<213> ORGANISM: artificial sequence
<220> FEATURE:
<223> OTHER INFORMATION: eIL-31 mature

<400> SEQUENCE: 1

Gly Pro Ile Tyr Gln Leu Gln Pro Lys Glu Ile Gln Ala Ile Ile Val
1               5                   10                  15

Glu Leu Gln Asn Leu Ser Lys Lys Leu Leu Asp Asp Tyr Leu Asn Lys
            20                  25                  30

Glu Lys Gly Val Gln Lys Phe Asp Ser Asp Leu Pro Ser Cys Phe Thr
        35                  40                  45

Ser Asp Ser Gln Ala Pro Gly Asn Ile Asn Ser Ser Ala Ile Leu Pro
    50                  55                  60

Tyr Phe Lys Ala Ile Ser Pro Ser Leu Asn Asn Asp Lys Ser Leu Tyr
65                  70                  75                  80

Ile Ile Glu Gln Leu Asp Lys Leu Asn Phe Gln Asn Ala Pro Glu Thr
                85                  90                  95

Glu Val Ser Met Pro Thr Asp Asn Phe Glu Arg Lys Arg Phe Ile Leu
            100                 105                 110

Thr Ile Leu Arg Trp Phe Ser Asn Cys Leu Glu
            115                 120

<210> SEQ ID NO 2
<211> LENGTH: 132
<212> TYPE: PRT
<213> ORGANISM: artificial sequence
<220> FEATURE:
<223> OTHER INFORMATION: eIL-31-C-His

<400> SEQUENCE: 2

Gly Pro Ile Tyr Gln Leu Gln Pro Lys Glu Ile Gln Ala Ile Ile Val
1               5                   10                  15

Glu Leu Gln Asn Leu Ser Lys Lys Leu Leu Asp Asp Tyr Leu Asn Lys
            20                  25                  30

Glu Lys Gly Val Gln Lys Phe Asp Ser Asp Leu Pro Ser Cys Phe Thr
        35                  40                  45

Ser Asp Ser Gln Ala Pro Gly Asn Ile Asn Ser Ser Ala Ile Leu Pro
    50                  55                  60

Tyr Phe Lys Ala Ile Ser Pro Ser Leu Asn Asn Asp Lys Ser Leu Tyr
65                  70                  75                  80

Ile Ile Glu Gln Leu Asp Lys Leu Asn Phe Gln Asn Ala Pro Glu Thr
                85                  90                  95

Glu Val Ser Met Pro Thr Asp Asn Phe Glu Arg Lys Arg Phe Ile Leu
            100                 105                 110

Thr Ile Leu Arg Trp Phe Ser Asn Cys Leu Glu Gly Gly Cys His His
```

His His His His
    130

<210> SEQ ID NO 3
<211> LENGTH: 132
<212> TYPE: PRT
<213> ORGANISM: artificial sequence
<220> FEATURE:
<223> OTHER INFORMATION: eIL31 antigen var1

<400> SEQUENCE: 3

Gly Pro Ile Tyr Gln Leu Gln Pro Lys Glu Ile Gln Ala Ile Ile Val
1               5                   10                  15

Glu Leu Gln Asn Leu Ser Lys Lys Leu Leu Asp Asp Tyr Leu Asn Lys
            20                  25                  30

Glu Lys Gly Val Gln Lys Phe Asp Ser Asp Leu Pro Ser Cys Phe Thr
        35                  40                  45

Ser Asp Ser Gln Ala Pro Gly Asn Ile Asn Ser Ser Ala Ile Leu Pro
    50                  55                  60

Tyr Phe Lys Ala Ile Ser Pro Ser Leu Asn Asn Asp Lys Ser Leu Tyr
65                  70                  75                  80

Ile Ile Glu Gln Leu Asp Lys Leu Asn Phe Gln Asn Ala Pro Glu Thr
                85                  90                  95

Glu Val Ser Met Pro Thr Asp Asn Phe Glu Arg Lys Arg Phe Ile Leu
            100                 105                 110

Thr Ile Leu Arg Trp Phe Ser Asn Cys Leu Glu His His His His
        115                 120                 125

His Gly Gly Cys
    130

<210> SEQ ID NO 4
<211> LENGTH: 132
<212> TYPE: PRT
<213> ORGANISM: artificial sequence
<220> FEATURE:
<223> OTHER INFORMATION: eIL31 antigen var2

<400> SEQUENCE: 4

Gly Gly Cys Gly Pro Ile Tyr Gln Leu Gln Pro Lys Glu Ile Gln Ala
1               5                   10                  15

Ile Ile Val Glu Leu Gln Asn Leu Ser Lys Lys Leu Leu Asp Asp Tyr
            20                  25                  30

Leu Asn Lys Glu Lys Gly Val Gln Lys Phe Asp Ser Asp Leu Pro Ser
        35                  40                  45

Cys Phe Thr Ser Asp Ser Gln Ala Pro G

<210> SEQ ID NO 5
<211> LENGTH: 126
<212> TYPE: PRT
<213> ORGANISM: artificial sequence
<220> FEATURE:
<223> OTHER INFORMATION: eIL31 antigen var3

<400> SEQUENCE: 5

Gly Gly Cys Gly Pro Ile Tyr Gln Leu Gln Pro Lys Glu Ile Gln Ala
1               5                   10                  15

Ile Ile Val Glu Leu Gln Asn Leu Ser Lys Lys Leu Leu Asp Asp Tyr
            20                  25                  30

Leu Asn Lys Glu Lys Gly Val Gln Lys Phe Asp Ser Asp Leu Pro Ser
        35                  40                  45

Cys Phe Thr Ser Asp Ser Gln Ala Pro Gly Asn Ile Asn Ser Ser Ala
    50                  55                  60

Ile Leu Pro Tyr Phe Lys Ala Ile Ser Pro Ser Leu Asn Asn Asp Lys
65                  70                  75                  80

Ser Leu Tyr Ile Ile Glu Gln Leu Asp Lys Leu Asn Phe Gln Asn Ala
                85                  90                  95

Pro Glu Thr Glu Val Ser Met Pro Thr Asp Asn Phe Glu Arg Lys Arg
            100                 105                 110

Phe Ile Leu Thr Ile Leu Arg Trp Phe Ser Asn Cys Leu Glu
        115                 120                 125

<210> SEQ ID NO 6
<211> LENGTH: 115
<212> TYPE: PRT
<213> ORGANISM: artificial sequence
<220> FEATURE:
<223> OTHER INFORMATION: eIL5 mature

<400> SEQUENCE: 6

Leu Ala Val Glu Ser Pro Met Asn Arg Leu Val Ala Glu Thr Leu Thr
1               5                   10                  15

Leu Leu Ser Thr His Arg Thr Leu Leu Ile Gly Asp Gly Asn Leu Met
            20                  25                  30

Ile Pro Thr Pro Glu His Lys Asn His Gln Leu Cys Ile Glu Glu Val
        35                  40                  45

Phe Gln Gly Ile Asp Thr Leu Lys Asn Gln Thr Val Gln Gly Asp Ala
    50                  55                  60

Val Ala Lys Leu Phe Gln Asn Leu Ser Leu Ile Lys Gly Tyr Ile Asp
65                  70                  75                  80

Leu Gln Lys Lys Lys Cys Gly Gly Glu Arg Trp Arg Val Lys Gln Phe
                85                  90                  95

Leu Asp Tyr Leu Gln Glu Phe Leu Gly Val Ile Asn Thr Glu Trp Thr
            100                 105                 110

Ile Glu Gly
        115

<210> SEQ ID NO 7
<211> LENGTH: 127
<212> TYPE: PRT
<213> ORGANISM: artificial sequence
<220> FEATURE:
<223> OTHER INFORMATION: eIL-5-C-His1

<400> SEQUENCE: 7

Ala Val Glu Ser Pro Met Asn Arg Leu Val Ala Glu Thr Leu Thr Leu

```
                1               5                   10                  15
            Leu Ser Thr His Arg Thr Leu Leu Ile Gly Asp Gly Asn Leu Met Ile
                        20                  25                  30

Pro Thr Pro Glu His Lys Asn His Gln Leu Cys Ile Glu Glu Val Phe
                        35                  40                  45

Gln Gly Ile Asp Thr Leu Lys Asn Gln Thr Val Gln Gly Asp Ala Val
                        50                  55                  60

Ala Lys Leu Phe Gln Asn Leu Ser Leu Ile Lys Gly Tyr Ile Asp Leu
            65                  70                  75                  80

Gln Lys Lys Lys Cys Gly Gly Glu Arg Trp Arg Val Lys Gln Phe Leu
                        85                  90                  95

Asp Tyr Leu Gln Glu Phe Leu Gly Val Ile Asn Thr Glu Trp Thr Ile
                        100                 105                 110

Glu Gly Gly Gly Cys Leu Glu His His His His His His
                        115                 120                 125

<210> SEQ ID NO 8
<211> LENGTH: 124
<212> TYPE: PRT
<213> ORGANISM: artificial sequence
<220> FEATURE:
<223> OTHER INFORMATION: eIL-5-C-His2

<400> SEQUENCE: 8

Leu Ala Val Glu Ser Pro Met Asn Arg Leu Val Ala Glu Thr Leu Thr
1               5                   10                  15

Leu Leu Ser Thr His Arg Thr Leu Leu Ile Gly Asp Gly Asn Leu Met
            20                  25                  30

Ile Pro Thr Pro Glu His Lys Asn His Gln Leu Cys Ile Glu Glu Val
            35                  40                  45

Phe Gln Gly Ile Asp Thr Leu Lys Asn Gln Thr Val Gln Gly Asp Ala
            50                  55                  60

Val Ala Lys Leu Phe Gln Asn Leu Ser Leu Ile Lys Gly Tyr Ile Asp
65                  70                  75                  80

Leu Gln Lys Lys Lys Cys Gly Gly Glu Arg Trp Arg Val Lys Gln Phe
            85                  90                  95

Leu Asp Tyr Leu Gln Glu Phe Leu Gly Val Ile Asn Thr Glu Trp Thr
            100                 105                 110

Ile Glu Gly Gly Gly Cys His His His His His His
            115                 120

<210> SEQ ID NO 9
<211> LENGTH: 124
<212> TYPE: PRT
<213> ORGANISM: artificial sequence
<220> FEATURE:
<223> OTHER INFORMATION: eIL5 antigen var1

<400> SEQUENCE: 9

Gly Gly Cys Leu Ala Val Glu Ser Pro Met Asn Arg Leu Val Ala Glu
1               5                   10                  15

Thr Leu Thr Leu Leu Ser Thr His Arg Thr Leu Leu Ile Gly Asp Gly
            20                  25                  30

Asn Leu Met Ile Pro Thr Pro Glu His Lys Asn His Gln Leu

Gly Asp Ala Val Ala Lys Leu Phe Gln Asn Leu Ser Leu Ile Lys Gly
 65                  70                  75                  80

Tyr Ile Asp Leu Gln Lys Lys Cys Gly Gly Glu Arg Trp Arg Val
                 85                  90                  95

Lys Gln Phe Leu Asp Tyr Leu Gln Glu Phe Leu Gly Val Ile Asn Thr
            100                 105                 110

Glu Trp Thr Ile Glu Gly His His His His His
        115                 120

<210> SEQ ID NO 10
<211> LENGTH: 118
<212> TYPE: PRT
<213> ORGANISM: artificial sequence
<220> FEATURE:
<223> OTHER INFORMATION: eIL5 antigen var2

<400> SEQUENCE: 10

Gly Gly Cys Leu Ala Val Glu Ser Pro Met Asn Arg Leu Val Ala Glu
1               5                   10                  15

Thr Leu Thr Leu Leu Ser Thr His Arg Thr Leu Leu Ile Gly Asp Gly
            20                  25                  30

Asn Leu Met Ile Pro Thr Pro Glu His Lys Asn His Gln Leu Cys Ile
        35                  40                  45

Glu Glu Val Phe Gln Gly Ile Asp Thr Leu Lys Asn Gln Thr Val Gln
    50                  55                  60

Gly Asp Ala Val Ala Lys Leu Phe Gln Asn Leu Ser Leu Ile Lys Gly
 65                 70                  75                  80

Tyr Ile Asp Leu Gln Lys Lys Cys Gly Gly Glu Arg Trp Arg Val
                 85                  90                  95

Lys Gln Phe Leu Asp Tyr Leu Gln Glu Phe Leu Gly Val Ile Asn Thr
            100                 105                 110

Glu Trp Thr Ile Glu Gly
        115

<210> SEQ ID NO 11
<211> LENGTH: 19
<212> TYPE: DNA
<213> ORGANISM: artificial sequence
<220> FEATURE:
<223> OTHER INFORMATION: forward primer eIL31

<400> SEQUENCE: 11
aacaaagaga agggagtgc                                                  19

<210> SEQ ID NO 12
<211> LENGTH: 19
<212> TYPE: DNA
<213> ORGANISM: artificial sequence
<220> FEATURE:
<223> OTHER INFORMATION: reverse primer eIL31

<400> SEQUENCE: 12
gctgagctgt tgatgttgc                                                  19

<210> SEQ ID NO 13
<211> LENGTH: 20
<212> TYPE: DNA
<213> ORGANISM: artificial sequence
<220> FEATURE:
<223> OTHER INFORMATION: forward primer ebeta actin

<400> SEQUENCE: 13

```
ccagcacgat gaagatcaag                                                 20

<210> SEQ ID NO 14
<211> LENGTH: 20
<212> TYPE: DNA
<213> ORGANISM: artificial sequence
<220> FEATURE:
<223> OTHER INFORMATION: reverse primer ebeta actin

<400> SEQUENCE: 14
gtggacaatg aggccagaat                                                 20

<210> SEQ ID NO 15
<211> LENGTH: 218
<212> TYPE: PRT
<213> ORGANISM: cucumber mosaic virus

<400> SEQUENCE: 15
```

Met Asp Lys Ser Glu Ser Thr Ser Ala Gly Arg Ser Arg Arg Arg
1               5                   10                  15

Pro Arg Arg Gly Ser Arg Ser Ala Pro Ser Ser Ala Asp Ala Asn Phe
            20                  25                  30

Arg Val Leu Ser Gln Gln Leu Ser Arg Leu Asn Lys Thr Leu Ala Ala
        35                  40                  45

Gly Arg Pro Thr Ile Asn His Pro Thr Phe Val Gly Ser Glu Arg Cys
    50                  55                  60

Lys Pro Gly Tyr Thr Phe Thr Ser Ile Thr Leu Lys Pro Pro Lys Ile
65                  70                  75                  80

Asp Arg Gly Ser Tyr Tyr Gly Lys Arg Leu Leu Leu Pro Asp Ser Val
                85                  90                  95

Thr Glu Tyr Asp Lys Lys Leu Val Ser Arg Ile Gln Ile Arg Val Asn
            100                 105                 110

Pro Leu Pro Lys Phe Asp Ser Thr Val Trp Val Thr Val Arg Lys Val
        115                 120                 125

Pro Ala Ser Ser Asp Leu Ser Val Ala Ala Ile Ser Ala Met Phe Ala
    130                 135                 140

Asp Gly Ala Ser Pro Val Leu Val Tyr Gln Tyr Ala Ala Ser Gly Val
145                 150                 155                 160

Gln Ala Asn Asn Lys Leu Leu Tyr Asp Leu Ser Ala Met Arg Ala Asp
                165                 170                 175

Ile Gly Asp Met Arg Lys Tyr Ala Val Leu Val Tyr Ser Lys Asp Asp
            180                 185                 190

Ala Leu Glu Thr Asp Glu Leu Val Leu His Val Asp Val Glu His Gln
        195                 200                 205

Arg Ile Pro Thr Ser Gly Val Leu Pro Val
    210                 215

```
<210> SEQ ID NO 16
<211> LENGTH: 217
<212> TYPE: PRT
<213> ORGANISM: cucumber mosaic virus

<400> SEQUENCE: 16
```

Asp Lys Ser Glu Ser Thr Ser Ala Gly Arg Asn Arg Arg Arg Pro
1               5                   10                  15

Arg Arg Gly Ser Arg Ser Ala Ser Ser Ala Asp Ala Asn Phe Arg
            20                  25                  30

```
Val Leu Ser Gln Gln Leu Ser Arg Leu Asn Lys Thr Leu Ala Ala Gly
         35                  40                  45

Arg Pro Thr Ile Asn His Pro Thr Phe Val Gly Ser Glu Arg Cys Lys
 50                  55                  60

Pro Gly Tyr Thr Phe Ser Ser Ile Thr Leu Lys Pro Lys Ile Asp
 65                  70                  75                  80

Arg Gly Ser Tyr Tyr Gly Lys Arg Leu Leu Leu Pro Asp Ser Val Thr
                 85                  90                  95

Glu Phe Asp Lys Lys Leu Val Ser Arg Ile Gln Ile Arg Val Asn Pro
                100                 105                 110

Leu Pro Lys Phe Asp Ser Thr Val Trp Val Thr Val Arg Lys Val Pro
            115                 120                 125

Ala Ser Ser Asp Leu Ser Val Ala Ala Ile Ser Ala Met Phe Ala Asp
130                 135                 140

Gly Ala Ser Pro Val Leu Val Tyr Gln Tyr Ala Ala Ser Gly Val Gln
145                 150                 155                 160

Ala Asn Asn Lys Leu Leu Tyr Asp Leu Ser Ala Met Arg Ala Asp Ile
                165                 170                 175

Gly Asp Met Arg Lys Tyr Ala Val Leu Val Tyr Ser Lys Asp Asp Ala
            180                 185                 190

Leu Glu Thr Asp Glu Leu Val Leu His Val Asp Ile Glu His Gln Arg
            195                 200                 205

Ile Pro Thr Ser Gly Val Leu Pro Val
            210                 215

<210> SEQ ID NO 17
<211> LENGTH: 218
<212> TYPE: PRT
<213> ORGANISM: cucumber mosaic virus

<400> SEQUENCE: 17

Met Asp Lys Ser Glu Ser Pro Asn Ala Ser Arg Thr Ser Arg Arg Arg
  1               5                  10                  15

Arg Pro Arg Arg Gly Ser Arg Ser Ala Ser Gly Ala Asp Ala Gly Leu
                 20                  25                  30

Arg Ala Leu Thr Gln Gln Met Leu Lys Leu Asn Lys Thr Leu Ala Ile
             35                  40                  45

Gly Arg Pro Thr Leu Asn His Pro Thr Phe Val Gly Ser Ala Ser Cys
 50                  55                  60

Lys Pro Gly Tyr Thr Phe Thr Ser Ile Thr Leu Lys Pro Pro Glu Ile
 65                  70                  75                  80

Glu Lys Gly Ser Tyr Phe Gly Arg Arg Leu Ser Leu Pro Asp Ser Val
                 85                  90                  95

Thr Asp Tyr Asp Lys Lys Leu Val Ser Arg Ile Gln Ile Arg Ile Asn
                100                 105                 110

Pro Leu Pro Lys Phe Asp Ser Thr Val Trp Val Thr Val Arg Lys Val
            115                 120                 125

Pro Ser Ser Ser Asp Leu Ser Val Ala Thr Ile Ser Ala Met Phe Gly
130                 135                 140

Asp Gly Asn Ser Pro Val Leu Val Tyr Gln Tyr Thr Ala Ser Gly Val
145                 150                 155                 160

Gln Ala Asn Asn Lys Leu Leu Tyr Asp Leu Ser Glu Met Arg Ala Asp
                165                 170                 175

Ile Gly Asp Met Arg Lys Tyr Ala Val Leu Val Tyr Ser Lys Asp Asp
            180                 185                 190
```

```
Lys Leu Glu Glu Asp Glu Ile Val Leu His Val Asp Val Glu His Gln
        195                 200                 205

Arg Ile Pro Ile Ser Arg Met Leu Pro Thr
        210                 215
```

<210> SEQ ID NO 18
<211> LENGTH: 14
<212> TYPE: PRT
<213> ORGANISM: artificial sequence
<220> FEATURE:
<223> OTHER INFORMATION: tetanus toxoid epitope tt830

<400> SEQUENCE: 18

```
Gln Tyr Ile Lys Ala Asn Ser Lys Phe Ile Gly Ile Thr Glu
1               5                   10
```

<210> SEQ ID NO 19
<211> LENGTH: 13
<212> TYPE: PRT
<213> ORGANISM: artificial sequence
<220> FEATURE:
<223> OTHER INFORMATION: PADRE

<400> SEQUENCE: 19

```
Ala Lys Phe Val Ala Ala Trp Thr Leu Lys Ala Ala Ala
1               5                   10
```

<210> SEQ ID NO 20
<211> LENGTH: 222
<212> TYPE: PRT
<213> ORGANISM: artificial sequence
<220> FEATURE:
<223> OTHER INFORMATION: CMV-Ntt830

<400> SEQUENCE: 20

```
Met Gly Gln Tyr Ile Lys Ala Asn Ser Lys Phe Ile Gly Ile Thr Glu
1               5                   10                  15

Arg Arg Arg Arg Pro Arg Arg Gly Ser Arg Ser Ala Pro Ser Ser Ala
                20                  25                  30

Asp Ala Asn Phe Arg Val Leu Ser Gln Gln Leu Ser Arg Leu Asn Lys
            35                  40                  45

Thr Leu Ala Ala Gly Arg Pro Thr Ile Asn His Pro Thr Phe Val Gly
        50                  55                  60

Ser Glu Arg Cys Lys Pro Gly Tyr Thr Phe Thr Ser Ile Thr Leu Lys
65                  70                  75                  80

Pro Pro Lys Ile Asp Arg Gly Ser Tyr Tyr Gly Lys Arg Leu Leu Leu
                85                  90                  95

Pro Asp Ser Val Thr Glu Tyr Asp Lys Lys Leu Val Ser Arg Ile Gln
            100                 105                 110

Ile Arg Val Asn Pro Leu Pro Lys Phe Asp Ser Thr Val Trp Val Thr
        115                 120                 125

Val Arg Lys Val Pro Ala Ser Ser Asp Leu Ser Val Ala Ala Ile Ser
    130                 135                 140

Ala Met Phe Ala Asp Gly Ala Ser Pro Val Leu Val Tyr Gln Tyr Ala
145                 150                 155                 160

Ala Ser Gly Val Gln Ala Asn Asn Lys Leu Leu Tyr Asp Leu Ser Ala
                165                 170                 175

Met Arg Ala Asp Ile Gly Asp Met Arg Lys Tyr Ala Val Leu Val Tyr
            180                 185                 190
```

```
Ser Lys Asp Asp Ala Leu Glu Thr Asp Glu Leu Val Leu His Val Asp
        195                 200                 205

Val Glu His Gln Arg Ile Pro Thr Ser Gly Val Leu Pro Val
    210                 215                 220
```

<210> SEQ ID NO 21
<211> LENGTH: 220
<212> TYPE: PRT
<213> ORGANISM: artificial sequence
<220> FEATURE:
<223> OTHER INFORMATION: CMV-Npadr

<400> SEQUENCE: 21

```
Met Ala Lys Phe Val Ala Ala Trp Thr Leu Lys Ala Ala Arg Arg
1               5                   10                  15

Arg Arg Pro Arg Arg Gly Ser Arg Ser Ala Pro Ser Ser Ala Asp Ala
            20                  25                  30

Asn Phe Arg Val Leu Ser Gln Gln Leu Ser Arg Leu Asn Lys Thr Leu
        35                  40                  45

Ala Ala Gly Arg Pro Thr Ile Asn His Pro Thr Phe Val Gly Ser Glu
    50                  55                  60

Arg Cys Lys Pro Gly Tyr Thr Phe Thr Ser Ile Thr Leu Lys Pro Pro
65                  70                  75                  80

Lys Ile Asp Arg Gly Ser Tyr Tyr Gly Lys Arg Leu Leu Leu Pro Asp
                85                  90                  95

Ser Val Thr Glu Tyr Asp Lys Lys Leu Val Ser Arg Ile Gln Ile Arg
            100                 105                 110

Val Asn Pro Leu Pro Lys Phe Asp Ser Thr Val Trp Val Thr Val Arg
        115                 120                 125

Lys Val Pro Ala Ser Ser Asp Leu Ser Val Ala Ala Ile Ser Ala Met
    130                 135                 140

Phe Ala Asp Gly Ala Ser Pro Val Leu Val Tyr Gln Tyr Ala Ala Ser
145                 150                 155                 160

Gly Val Gln Ala Asn Asn Lys Leu Leu Tyr Asp Leu Ser Ala Met Arg
                165                 170                 175

Ala Asp Ile Gly Asp Met Arg Lys Tyr Ala Val Leu Val Tyr Ser Lys
            180                 185                 190

Asp Asp Ala Leu Glu Thr Asp Glu Leu Val Leu His Val Asp Val Glu
        195                 200                 205

His Gln Arg Ile Pro Thr Ser Gly Val Leu Pro Val
    210                 215                 220
```

<210> SEQ ID NO 22
<211> LENGTH: 420
<212> TYPE: DNA
<213> ORGANISM: artificial sequence
<220> FEATURE:
<223> OTHER INFORMATION: pET42b-eIL-31

<400> SEQUENCE: 22

```
catatgggtc cgatttatca gctgcagccg aaagaaattc aggccattat tgttgaactg    60
cagaacctga gcaaaaaact gctggatgat tacctgaaca agaaaaaagg cgtgcagaaa   120
tttgatagcg atctgccgag ctgttttacc agcgatagcc aggcaccggg taacattaat   180
agcagcgcaa ttctgccgta tttcaaagca attagcccga gcctgaataa tgataaaagc   240
ctgtatatta tcgaacagct ggataaactg aactttcaga tgcaccggaa accgaagtt   300 agcatgccga ccgataattt tgaacgcaaa cgttttattc tgaccatcct gcgttggttt   360
```

```
agcaattgtc tggaaggtgg tggttgtctc gagcaccacc accaccacca ccaccactaa    420
```

<210> SEQ ID NO 23
<211> LENGTH: 390
<212> TYPE: DNA
<213> ORGANISM: artificial sequence
<220> FEATURE:
<223> OTHER INFORMATION: pET42b-eIL-5

<400> SEQUENCE: 23

```
catatggcag ttgaaagccc gatgaatcgt ctggttgcag aaaccctgac cctgctgagc     60
acccatcgta cactgctgat tggtgatggt aatctgatga ttccgacacc ggaacataaa    120
aatcatcagc tgtgtatcga agaagtgttt cagggcattg ataccctgaa aaatcagacc    180
gttcagggtg atgcagttgc aaaactgttt cagaatctga gcctgatcaa aggctatatc    240
gatctgcaga aaaaaaaatg cggtggtgaa cgttggcgtg ttaaacagtt tctggattat    300
ctgcaagaat ttctgggcgt gattaatacc gaatggacca ttgaaggtgg tggttgtctc    360
gagcaccacc accaccacca ccaccactaa                                     390
```

<210> SEQ ID NO 24
<211> LENGTH: 132
<212> TYPE: PRT
<213> ORGANISM: Bacteriophage Q-beta

<400> SEQUENCE: 24

```
Ala Lys Leu Glu Thr Val Thr Leu Gly Asn Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Ala Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130
```

<210> SEQ ID NO 25
<211> LENGTH: 329
<212> TYPE: PRT
<213> ORGANISM: Bacteriophage Q-beta

<400> SEQUENCE: 25

```
Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45
```

```
Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
                100                 105                 110

Leu Ala Ala Leu Leu Ala Ser Pro Leu Leu Ile Asp Ala Ile Asp Gln
                115                 120                 125

Leu Asn Pro Ala Tyr Trp Thr Leu Leu Ile Ala Gly Gly Ser Gly
    130                 135                 140

Ser Lys Pro Asp Pro Val Ile Pro Asp Pro Ile Asp Pro Pro
145                 150                 155                 160

Gly Thr Gly Lys Tyr Thr Cys Pro Phe Ala Ile Trp Ser Leu Glu Glu
                165                 170                 175

Val Tyr Glu Pro Pro Thr Lys Asn Arg Pro Trp Pro Ile Tyr Asn Ala
                180                 185                 190

Val Glu Leu Gln Pro Arg Glu Phe Asp Val Ala Leu Lys Asp Leu Leu
    195                 200                 205

Gly Asn Thr Lys Trp Arg Asp Trp Asp Ser Arg Leu Ser Tyr Thr Thr
    210                 215                 220

Phe Arg Gly Cys Arg Gly Asn Gly Tyr Ile Asp Leu Asp Ala Thr Tyr
225                 230                 235                 240

Leu Ala Thr Asp Gln Ala Met Arg Asp Gln Lys Tyr Asp Ile Arg Glu
                245                 250                 255

Gly Lys Lys Pro Gly Ala Phe Gly Asn Ile Glu Arg Phe Ile Tyr Leu
                260                 265                 270

Lys Ser Ile Asn Ala Tyr Cys Ser Leu Ser Asp Ile Ala Ala Tyr His
    275                 280                 285

Ala Asp Gly Val Ile Val Gly Phe Trp Arg Asp Pro Ser Ser Gly Gly
    290                 295                 300

Ala Ile Pro Phe Asp Phe Thr Lys Phe Asp Lys Thr Lys Cys Pro Ile
305                 310                 315                 320

Gln Ala Val Ile Val Val Pro Arg Ala
                325

<210> SEQ ID NO 26
<211> LENGTH: 131
<212> TYPE: PRT
<213> ORGANISM: Bacteriophage AP205

<400> SEQUENCE: 26

Met Ala Asn Lys Pro Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
                20                  25                  30

Leu Arg Gln Arg Val Lys Val Gly Ile Ala Glu Leu Asn Asn Val Ser
            35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95
```

-continued

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130

<210> SEQ ID NO 27
<211> LENGTH: 27
<212> TYPE: PRT
<213> ORGANISM: artificial sequence
<220> FEATURE:
<223> OTHER INFORMATION: aa 2-28 of SEQ ID NO:24

<400> SEQUENCE: 27

Asp Lys Ser Glu Ser Thr Ser Ala Gly Arg Ser Arg Arg Arg Arg Pro
1               5                   10                  15

Arg Arg Gly Ser Arg Ser Ala Pro Ser Ser Ala
            20                  25

<210> SEQ ID NO 28
<211> LENGTH: 140
<212> TYPE: PRT
<213> ORGANISM: artificial sequence
<220> FEATURE:
<223> OTHER INFORMATION: mIL31 mature

<400> SEQUENCE: 28

Thr Cys Ser Leu Ser Phe Gly Ala Pro Ile Ser Lys Glu Asp Leu Arg
1               5                   10                  15

Thr Thr Ile Asp Leu Leu Lys Gln Glu Ser Gln Asp Leu Tyr Asn Asn
            20                  25                  30

Tyr Ser Ile Lys Gln Ala Ser Gly Met Ser Ala Asp Glu Ser Ile Gln
        35                  40                  45

Leu Pro Cys Phe Ser Leu Asp Arg Glu Ala Leu Thr Asn Ile Ser Val
    50                  55                  60

Ile Ile Ala His Leu Glu Lys Val Lys Val Leu Ser Glu Asn Thr Val
65                  70                  75                  80

Asp Thr Ser Trp Val Ile Arg Trp Leu Thr Asn Ile Ser Cys Phe Asn
                85                  90                  95

Pro Leu Asn Leu Asn Ile Ser Val Pro Gly Asn Thr Asp Glu Ser Tyr
            100                 105                 110

Asp Cys Lys Val Phe Val Leu Thr Val Leu Lys Gln Phe Ser Asn Cys
        115                 120                 125

Met Ala Glu Leu Gln Ala Lys Asp Asn Thr Thr Cys
    130                 135                 140

<210> SEQ ID NO 29
<211> LENGTH: 150
<212> TYPE: PRT
<213> ORGANISM: artificial sequence
<220> FEATURE:
<223> OTHER INFORMATION: mIL-31-C-His

<400> SEQUENCE: 29

Thr Cys Ser Leu Ser Phe Gly Ala Pro Ile Ser Lys Glu Asp Leu Arg
1               5                   10                  15

Thr Thr Ile Asp Leu Leu Lys Gln Glu Ser Gln Asp Leu Tyr Asn Asn
            20                  25                  30

```
Tyr Ser Ile Lys Gln Ala Ser Gly Met Ser Ala Asp Glu Ser Ile Gln
            35                  40                  45

Leu Pro Cys Phe Ser Leu Asp Arg Glu Ala Leu Thr Asn Ile Ser Val
 50                  55                  60

Ile Ile Ala His Leu Glu Lys Val Lys Val Leu Ser Glu Asn Thr Val
 65                  70                  75                  80

Asp Thr Ser Trp Val Ile Arg Trp Leu Thr Asn Ile Ser Cys Phe Asn
                 85                  90                  95

Pro Leu Asn Leu Asn Ile Ser Val Pro Gly Asn Thr Asp Glu Ser Tyr
             100                 105                 110

Asp Cys Lys Val Phe Val Leu Thr Val Leu Lys Gln Phe Ser Asn Cys
             115                 120                 125

Met Ala Glu Leu Gln Ala Lys Asp Asn Thr Thr Cys Gly Gly Gly Cys
        130                 135                 140

His His His His His His
145                 150

<210> SEQ ID NO 30
<211> LENGTH: 20
<212> TYPE: DNA
<213> ORGANISM: artificial sequence
<220> FEATURE:
<223> OTHER INFORMATION: forward primer

<400> SEQUENCE: 30
ggctgtattc ccctccatcg                                              20

<210> SEQ ID NO 31
<211> LENGTH: 22
<212> TYPE: DNA
<213> ORGANISM: artificial sequence
<220> FEATURE:
<223> OTHER INFORMATION: reverse primer

<400> SEQUENCE: 31
ccagttggta acaatgccat gt                                           22
```

TREATMENT OF PRURITUS IN HORSES

REFERENCE TO AN ELECTRONIC SEQUENCE LISTING

The contents of the electronic sequence listing (0192_0093US1_SL.txt; Size: 33 KB; and Date of Creation: Sep. 1, 2019) is herein incorporated by reference in its entirety.

The present invention relates to compositions, immunogenic or vaccine compositions and pharmaceutical compositions for the prevention or treatment of a condition or disorder selected from a pruritic condition or an allergic condition, of equine mammals, preferably of horses. Furthermore, the invention provides methods for preventing or treating pruritus, preferably pruritus associated with a pruritic condition or an allergic condition such as allergic dermatitis, of equine mammals, preferably of horses.

RELATED ART

Pruritic conditions and allergic conditions are commonly seen in horses (S. D. White, Equine vet. Educ. (2015) 27 (3) 156-166). Pruritus-mediated itching of the skin will, for example, manifest clinically in a dermatitis phenotype and may be of allergic origin. Allergic dermatitis development is poorly understood. Potential factors involved are numerous. Although the potential cause is an allergen, antihistamines, have little effect and do neither cure nor mitigate pruritus and dermatitis (S. D. White, Equine vet. Educ. (2015) 27 (3) 156-166). An underlying allergic cause can be of environmental origin, such as allergens from trees, grass, pollens, molds, fungi, dust mites, dusts, danders, feed (provender) mites, and insects but also from components in the food. Additionally, genetic predispositions are thought to favor pruritus-induced allergic dermatitis (Yu & Rosychuk 2013, Equine Dermatology, Veterinary Clincis of North America: Equine Practice).

The best-characterized disease in horses showing hallmarks of pruritus in combination with an allergic dermatitis, is called insect bite hypersensitivity (IBH), also known as "sweet itch" or "summer eczema". It is the most common allergic skin disease of equine mammals, in particular horses, and manifests as a chronic relapsing seasonal allergic dermatitis caused by the bites of insects of the genus *Culicoides* found in various areas of the world. Various studies have suggested IBH to be associated with IgE-mediated reactions against salivary gland proteins from *Culicoides*. Clinical signs of IBH derive from intense pruritus caused by hypersensitivity reactions to bites of blood feeding insects. The disease is initially characterized by numerous papules, tufted hair, hyperesthesia, and skin sensitization followed by scratching and rubbing. This self trauma leads to localized hair loss and excoriations which contribute to the perpetuation of secondary infections. If the disease progresses and becomes chronic, it may lead to fibrosis, hypertrophy of epidermal tissue, and marked hyperkeratosis and lichenification, visible in thickening of the skin, scaling, formation of transverse ridges and folds (Schaffartzik A., et al., Vet Immunol Immunopathol, 2012, 147:113-126). Commonly, allergies caused by other allergens manifest in similar clinical signs of dermatitis (Yu & Rosychuk 2013, Equine Dermatology, Veterinary Clincis of North America: Equine Practice).

Interleukin-31 (IL-31) is preferentially secreted by activated Th2 CD4+ cells, but also from mast cells and macrophages (Dillon et al. Nat Immunol 2004; 5:752-60). Th2 cells play a key role in type I allergic reactions but also have been recently linked to represent the "missing link" in neuro-immune crosstalk between immune cells and sensory nerves in itch. IL-31 belongs to the pg130/IL-6 cytokine family and binds to a heterodimeric receptor complex composed of IL-31 receptor A (IL-31RA) and oncostatin M receptor beta (OSMRβ) subunits (Dillon et al. 2004 Nat Immunol 2004; 5:752-60; Bilsborough et al. J Allergy Clin Immunol. 2006 117(2); 418-25). Upon ligand binding IL-31 receptor complex activates Janus kinase-signal transducer and activator of transcription (JAK-STAT), mitogen-activated protein kinase (MAPK), and phosphatidylinositol 3-kinase (PI3K) pathways (Zhang et al., 2008). IL-31 can directly bind on its receptor expressed by a small subset of small-sized nociceptive neurons of dorsal root ganglia (DRG), suggesting that this cytokine may directly activate pruritogenic signals in peripheral nerves (Mizuno et al., 2009; Sonkoly et al., 2006). Moreover, the receptor is found on a variety of other cells, such as keratinocytes, macrophages, and eosinophils (Kasraie et al., 2011; Kasraie et al., 2010; Zhang et al., 2008).

Transgenic mice overexpressing IL-31 developed severe pruritus, alopecia, and skin lesions accompanied by increased inflammatory cell infiltration into the skin (Dillon et al., 2004). An intradermal injection of IL-31 is known to induce itch (scratching) in murine skin (Zhang et al. 2008, Cevikba 2013). Patients with atopic dermatitis (AD) have skin-homing CD45RO+ memory cutaneous lymphocyte-associated antigen (CLA)-positive T cells expressing IL-31 and Th2 cells were found almost exclusively in the dermis. Approximately 60% of Th2 cells were positive for IL-31, whereas no IL-31 mRNA was found in other immune or resident skin cells such as keratinocytes, endothelial cells, and fibroblasts. The only other source of IL-31 besides Th2 cells were mature dendritic cells, although they produced significantly lower levels compared to Th2 cells (approximately 100-fold) (Ferdac Cevikbas, J Clin Allergy 2013). Levels of IL-31 mRNA in skin lesions from AD patients are considerably higher than in lesions of healthy patients (Sonkoly et al. J Allergy Clin Immunol 2006; 117:411-7). An antibody against human IL-31 (Bristol-Myres Squibb) for the treatment of itch in AD human patients entered clinical testing in 2012 (www.ClinicalTrials.gov: NCT01614756) and a monoclonal anti-canine IL-31 antibody for the treatment of AD in dogs recently entered the market (Gonzales et al. Vet Dermatol 2013; 24:48-e12; Michels et al. Vet Dermatol 2016; 27:478-e129).

IL-31 induced pruritus is independent of mast cell or basophil degranulation or proteinase-activated receptor-2 (PAR-2)-mediated itch. It seems, thus, that IL-31-mediated pruritus is not directly associated with type I mechanisms, however, type I allergic events can further increase pruritus, as IL-4 and IL-13 mRNA expression have been correlated to IL-31 mRNA levels in human and canine AD lesions (Nei et al. J. Allergy Clin. Immunol. 2006; 118, 930-937). In line with that it was suggested that IL-31 might be promoting allergic inflammation (Chattopadhyay et al. J Biol Chem 2007; 282:3014-26; Wai et al. Immunology 2007; 122, 532-541).

The current treatments to address pruritic or allergic conditions and disorders of equine mammals, in particular horses, comprise, for example, glucocorticosteroids or other systemically administered steroids. Due to the disadvantages such as toxic side-effects of these glucocorticosteroids, in particular in long-term treatments, there is an unmet need for alternative treatment options for said conditions and disorders in equine mammals, and in particular horses.

SUMMARY OF THE INVENTION

Skin biopsies from horses of dermatitis affected skin lesions have surprisingly shown that equine IL-31 mRNA was expressed in skin lesions from sites with pruritus-accompanied dermatitis, whereas it was completely absent in healthy horse skin samples. This is the first time equine IL-31 was detected in pruritic skin lesions of horses, beside eosinophils typically present in said lesions, and thus it is the first time suggesting a major role of equine IL-31 in the pathology of allergic pruritus in horses. Moreover, it has been surprisingly found that administration of compositions of the present invention comprising equine Interleukin-31 antigens linked to a core particle, preferably to a virus-like particle, to horses leads not only to strong induction of auto-antibodies, but, furthermore, the compositions of the present invention are effective for the prevention and treatment of a condition or disorder selected from a pruritic condition or an allergic condition, of an equine mammal, preferably of a horse, and in particular, are effective for the prevention and treatment of pruritus and pruritus-associated dermatitis. The latter was evidenced by in-vivo studies conducted with pruritic allergic dermatitis affected Icelandic horses. The effectiveness of the inventive compositions are surprisingly independent of a possible allergic trigger causing said pruritus or pruritus-associated dermatitis, be it allergens from trees, grass, pollens, dust mites, insects or the like.

Thus, vaccination of horses affected by pruritus or pruritus-associated dermatitis caused by multiple allergens with inventive compositions comprising eIL-31 antigens linked to CMV-VLPs led not only to significant decrease in mean skin lesion scores but, in particular, led to a very strong decrease in mean pruritus scores as compared to said scores determined in the season before treatment with the inventive compositions. The same surprising results have been found when preferred combination vaccines in accordance with the present invention, namely compositions comprising eIL-31 antigens linked to CMV-VLPs and compositions comprising eIL-5 antigens linked to CMV-VLPs were used to treat horses affected by pruritus or pruritus-associated dermatitis caused by multiple allergens. Since many horses are typically not only allergic to one single allergen, but rather react against multiple allergens (also due to cross-reactivities of different allergens), an allergen independent therapy is highly desired to effectively resolve the common pruritic phenotype caused by said allergic conditions or disorders.

Therefore, in a first aspect, the present invention provides for a composition comprising: (a) a core particle with at least one first attachment site; and (b) at least one antigen with at least one second attachment site, wherein said at least one antigen is an equine Interleukin-31 antigen (eIL-31 antigen), wherein said eIL-31 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1; wherein (a) and (b) are linked through said at least one first and said at least one second attachment site via at least one non-peptide covalent bond; for use in a method of prevention or treatment of a condition or disorder selected from a pruritic condition or an allergic condition, of an equine mammal, preferably of a horse, wherein preferably an effective amount of said composition is administered to said equine mammal, preferably to said horse.

In a preferred embodiment, said condition or disorder is pruritus of an equine mammal, preferably of a horse. In a further preferred embodiment, said pruritus is pruritus associated with allergic dermatitis or pruritus associated with atopic dermatitis. In a further preferred embodiment, said pruritus is pruritus associated with allergic dermatitis. In a further preferred embodiment, said pruritus is pruritus associated with atopic dermatitis. In a further preferred embodiment, said condition or disorder is not the prevention or treatment of insect bite hypersensitivity (IBH) of an equine mammal, preferably of a horse. In a further preferred embodiment, said condition or disorder is the prevention or treatment of insect bite hypersensitivity (IBH) of an equine mammal, preferably of a horse.

In a further aspect, the present invention provides for a composition comprising: (a) a core particle with at least one first attachment site; and (b) at least one antigen with at least one second attachment site, wherein said at least one antigen is an equine Interleukin-31 antigen (eIL-31 antigen), wherein said eIL-31 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1; wherein (a) and (b) are linked through said at least one first and said at least one second attachment site via at least one non-peptide covalent bond; for use in a method of prevention or treatment of pruritus of an equine mammal, preferably of a horse, wherein preferably said pruritus is associated with a pruritic condition or an allergic condition, and wherein again further preferably said pruritic condition or said allergic condition is selected from atopic dermatitis, eczema, psoriasis, scleroderma, pruritus, allergic dermatitis, summer eczema (IBH), bacterial folliculitis, dermatophytosis, recurrent urticaria, heaves, inflammatory airway disease, recurrent airway obstruction, airway hyper-responsiveness, chronic obstruction pulmonary disease, and inflammatory processes resulting from autoimmunity, and wherein preferably said pruritic condition or said allergic condition is selected from atopic dermatitis, eczema, pruritus, allergic dermatitis and recurrent urticaria, and wherein preferably an effective amount of said composition is administered to said equine mammal, preferably to said horse. In a preferred embodiment, said pruritus is pruritus associated with allergic dermatitis or pruritus associated with atopic dermatitis. In a preferred embodiment, said condition or disorder is pruritus associated with allergic dermatitis. In another preferred embodiment, said condition or disorder is pruritus associated with atopic dermatitis. In a preferred embodiment, said condition or disorder is not the prevention or treatment of insect bite hypersensitivity (IBH) of an equine mammal, preferably of a horse. In a preferred embodiment, said condition or disorder is the prevention or treatment of insect bite hypersensitivity (IBH) of an equine mammal, preferably of a horse.

In an again a further aspect, the present invention provides for a composition comprising a first composition and a second composition, wherein said first composition comprises (a) a first core particle with at least one first attachment site; and (b) at least one first antigen with at least one second attachment site, wherein said at least one first antigen is an equine Interleukin-31 antigen (eIL-31 antigen), wherein said eIL-31 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1; and wherein (a) and (b) are linked through said at least one first and said at least one second attachment site via at least one non-peptide covalent bond; and wherein said second composition comprises (c) a second core particle with at least one first attachment site; and (d) at least one second antigen with at least one second attachment site, wherein said at least one second antigen is an equine Interleukin-5 antigen (eIL-5 antigen), wherein said eIL-5 antigen comprises, or preferably is, a protein with the amino sequence selected from SEQ ID NO:6 or a protein with an amino acid sequence of at least 90%, preferably of at least 92%, further preferably of at least 95%, and again further preferably of at least 98% amino acid sequence identity with SEQ ID NO:6, and wherein (c) and (d) are linked through said at least one first and said at least one second attachment site via at least one non-peptide covalent bond, and wherein optionally said first or said second composition further comprises an adjuvant. In a further aspect, the present invention provides for said inventive composition for use as a medicament.

In an again a further aspect, the present invention provides for a kit comprising a first composition and a second composition, wherein said first composition comprises (a) a first core particle with at least one first attachment site; and (b) at least one first antigen with at least one second attachment site, wherein said at least one first antigen is an equine Interleukin-31 antigen (eIL-31 antigen), wherein said eIL-31 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1; and wherein (a) and (b) are linked through said at least one first and said at least one second attachment site via at least one non-peptide covalent bond; and wherein said second composition comprises (c) a second core particle with at least one first attachment site; and (d) at least one second antigen with at least one second attachment site, wherein said at least one second antigen is an equine Interleukin-5 antigen (eIL-5 antigen), wherein said eIL-5 antigen comprises, or preferably is, a protein with the amino sequence selected from SEQ ID NO:6 or a protein with an amino acid sequence of at least 90%, preferably of at least 92%, further preferably of at least 95%, and again further preferably of at least 98% amino acid sequence identity with SEQ ID NO:6, and wherein (c) and (d) are linked through said at least one first and said at least one second attachment site via at least one non-peptide covalent bond, and wherein optionally said first or said composition further comprises an adjuvant. In a further aspect, the present invention provides for said inventive kit for use as a medicament.

In an again a further aspect, the present invention provides for a composition comprising a first composition and a second composition, wherein said first composition comprises (a) a first core particle with at least one first attachment site; and (b) at least one first antigen with at least one second attachment site, wherein said at least one first antigen is an equine Interleukin-31 antigen (eIL-31 antigen), wherein said eIL-31 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1; and wherein (a) and (b) are linked through said at least one first and said at least one second attachment site via at least one non-peptide covalent bond; and wherein said second composition comprises (c) a second core particle with at least one first attachment site; and (d) at least one second antigen with at least one second attachment site, wherein said at least one second antigen is an equine Interleukin-5 antigen (eIL-5 antigen), wherein said eIL-5 antigen comprises, or preferably is, a protein with the amino sequence selected from SEQ ID NO:6 or a protein with an amino acid sequence of at least 90%, preferably of at least 92%, further preferably of at least 95%, and again further preferably of at least 98% amino acid sequence identity with SEQ ID NO:6, and wherein (c) and (d) are linked through said at least one first and said at least one second attachment site via at least one non-peptide covalent bond; for use in a method of prevention or treatment of a condition or disorder selected from a pruritic condition or an allergic condition, of an equine mammal, preferably of a horse, wherein preferably an effective amount of said composition is administered to said equine mammal, preferably to said horse. Preferably, said pruritic condition or said allergic condition is selected from atopic dermatitis, eczema, psoriasis, scleroderma, pruritus, allergic dermatitis, summer eczema (IBH), bacterial folliculitis, dermatophytosis, recurrent urticaria, heaves, inflammatory airway disease, recurrent airway obstruction, airway hyper-responsiveness, chronic obstruction pulmonary disease, and inflammatory processes resulting from autoimmunity, and wherein preferably said pruritic condition or said allergic condition is selected from atopic dermatitis, eczema, pruritus, allergic dermatitis, summer eczema (IBH), bacterial folliculitis, dermatophytosis, and recurrent urticaria, and wherein preferably said pruritic condition or said allergic condition is selected from atopic dermatitis, eczema, pruritus, allergic dermatitis, summer eczema (IBH) and recurrent urticarial, and wherein further preferably said pruritic condition or said allergic condition is selected from atopic dermatitis, eczema, pruritus, allergic dermatitis and recurrent urticaria.

In an again a further aspect, the present invention provides for a composition comprising a first composition and a second composition, wherein said first composition comprises (a) a first core particle with at least one first attachment site; and (b) at least one first antigen with at least one second attachment site, wherein said at least one first antigen is an equine Interleukin-31 antigen (eIL-31 antigen), wherein said eIL-31 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1; and wherein (a) and (b) are linked through said at least one first and said at least one second attachment site via at least one non-peptide covalent bond; and wherein said second composition comprises (c) a second core particle with at least one first attachment site; and (d) at least one second antigen with at least one second attachment site, wherein said at least one second antigen is an equine Interleukin-5 antigen (eIL-5 antigen), wherein said eIL-5 antigen comprises, or preferably is, a protein with the amino sequence selected from SEQ ID NO:6 or a protein with an amino acid sequence of at least 90%, preferably of at least 92%, further preferably of at least 95%, and again further preferably of at least 98% amino acid sequence identity with SEQ ID NO:6, and wherein (c) and (d) are linked through said at least one first and said at least one second attachment site via at least one non-peptide covalent bond; for use in a method of prevention or treatment of pruritus of an equine mammal, preferably of a horse, wherein preferably said pruritus is associated with a pruritic condition or an allergic condition, and wherein again further preferably said pruritic condition or said allergic condition is selected from atopic dermatitis, eczema, psoriasis, scleroderma, pruritus, allergic dermatitis, summer eczema (IBH), bacterial folliculitis, dermatophytosis, recurrent urticaria, heaves, inflammatory airway disease, recurrent airway obstruction, airway hyper-responsiveness, chronic obstruction pulmonary disease, and inflammatory processes resulting from autoimmunity, and wherein preferably said pruritic condition or said allergic condition is selected from atopic dermatitis, eczema, pruritus, allergic dermatitis, summer eczema (IBH), bacterial folliculitis, dermatophytosis, and recurrent urticaria, and wherein preferably said pruritic condition or said allergic condition is selected from atopic dermatitis, eczema, pruritus, allergic dermatitis, summer eczema (IBH) and recurrent urticarial, and wherein further preferably said pruritic condition or said allergic condition is selected from atopic dermatitis, eczema, pruritus, allergic dermatitis and recurrent urticaria and wherein preferably an effective amount of said composition is administered to said equine mammal, preferably to said horse. In a preferred embodiment, said pruritus is pruritus associated with allergic dermatitis or pruritus associated with atopic dermatitis. In a preferred embodiment, said condition or disorder is pruritus of an equine mammal, preferably of a horse. In a further preferred embodiment, said pruritus is pruritus associated with allergic dermatitis or pruritus associated with atopic dermatitis. In a further preferred embodiment, said pruritus is pruritus associated with allergic dermatitis. In a further preferred embodiment, said pruritus is pruritus associated with atopic dermatitis. In a preferred embodiment, said condition or disorder is not the prevention or treatment of insect bite hypersensitivity (IBH) of an equine mammal, preferably of a horse. In a preferred embodiment, said condition or disorder is the prevention or treatment of insect bite hypersensitivity (IBH) of an equine mammal, preferably of a horse.

In an again a further aspect, the present invention provides for a kit comprising a first composition and a second composition, wherein said first composition comprises (a) a first core particle with at least one first attachment site; and (b) at least one first antigen with at least one second attachment site, wherein said at least one first antigen is an equine Interleukin-31 antigen (eIL-31 antigen), wherein said eIL-31 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1; and wherein (a) and (b) are linked through said at least one first and said at least one second attachment site via at least one non-peptide covalent bond; and wherein said second composition comprises (c) a second core particle with at least one first attachment site; and (d) at least one second antigen with at least one second attachment site, wherein said at least one second antigen is an equine Interleukin-5 antigen (eIL-5 antigen), wherein said eIL-5 antigen comprises, or preferably is, a protein with the amino sequence selected from SEQ ID NO:6 or a protein with an amino acid sequence of at least 90%, preferably of at least 92%, further preferably of at least 95%, and again further preferably of at least 98% amino acid sequence identity with SEQ ID NO:6, and wherein (c) and (d) are linked through said at least one first and said at least one second attachment site via at least one non-peptide covalent bond; for use in a method of prevention or treatment of pruritus of an equine mammal, preferably of a horse, wherein preferably said pruritus is associated with a pruritic condition or an allergic condition, and wherein again further preferably said pruritic condition or said allergic condition is selected from atopic dermatitis, eczema, psoriasis, scleroderma, pruritus, allergic dermatitis, summer eczema (IBH), bacterial folliculitis, dermatophytosis, recurrent urticaria, heaves, inflammatory airway disease, recurrent airway obstruction, airway hyper-responsiveness, chronic obstruction pulmonary disease, and inflammatory processes resulting from autoimmunity, and wherein preferably said pruritic condition or said allergic condition is selected from atopic dermatitis, eczema, pruritus, allergic dermatitis, summer eczema (IBH), bacterial folliculitis, dermatophytosis, and recurrent urticaria, and wherein preferably said pruritic condition or said allergic condition is selected from atopic dermatitis, eczema, pruritus, allergic dermatitis, summer eczema (IBH) and recurrent urticarial, and wherein further preferably said pruritic condition or said allergic condition is selected from atopic dermatitis, eczema, pruritus, allergic dermatitis and recurrent urticaria and wherein preferably an effective amount of said composition is administered to said equine mammal, preferably to said horse. In a preferred embodiment, said pruritus is pruritus associated with allergic dermatitis or pruritus associated with atopic dermatitis. In a preferred embodiment, said condition or disorder is pruritus of an equine mammal, preferably of a horse. In a further preferred embodiment, said pruritus is pruritus associated with allergic dermatitis or pruritus associated with atopic dermatitis. In a further preferred embodiment, said pruritus is pruritus associated with allergic dermatitis. In a further preferred embodiment, said pruritus is pruritus associated with atopic dermatitis. In a preferred embodiment, said condition or disorder is not the prevention or treatment of insect bite hypersensitivity (IBH) of an equine mammal, preferably of a horse. In a preferred embodiment, said condition or disorder is the prevention or treatment of insect bite hypersensitivity (IBH) of an equine mammal, preferably of a horse.

The kit of the present invention allows for separate administration of said first composition and said second composition to said equine mammal, preferably to said horse, wherein preferably said separate administration of said first composition and said second composition is an administration of said first composition and said second composition at different point in time, i.e. occur sequentially and not contemporaneously; and/or wherein said separate administration of said first composition and said second composition is an administration of said first composition and said second composition at different location of said equine mammal, preferably of said horse, such as at different lymph nodes; and/or wherein said separate administration of said first composition and said second composition is an administration of said first composition and said second composition with different amounts, typically different effective amounts, of said first composition and said second composition. Thus, typically and preferably, said inventive kit are used for combinatory treatment in accordance with the present invention.

In a further aspect, the present invention provides for a pharmaceutical composition comprising said first composition and said second composition, and a pharmaceutically acceptable carrier.

In a further aspect, the present invention provides for a pharmaceutical composition comprising said first composition and said second composition, and a pharmaceutically acceptable carrier; for use in a method of prevention or treatment of pruritus of an equine mammal, preferably of a horse, wherein preferably said pruritus is associated with a pruritic condition or an allergic condition.

In a further aspect, the present invention provides for a method of prevention or treatment of a condition or disorder selected from a pruritic condition or an allergic condition, of an equine mammal, preferably of a horse, wherein said method comprises administering the inventive composition or the inventive pharmaceutical composition to an equine mammal, preferably to a horse.

In a further aspect, the present invention provides for a method of prevention or treatment of pruritus of an equine mammal, preferably of a horse, wherein preferably said pruritus is associated with a pruritic condition or an allergic condition, wherein said method comprises administering the inventive composition or the inventive pharmaceutical composition to an equine mammal, preferably to a horse.

In another aspect, the present invention provides for the use of the inventive composition or said inventive pharmaceutical composition for the manufacture of a medicament for the prevention or treatment of a condition or disorder selected from a pruritic condition or an allergic condition, of an equine mammal, preferably of a horse, wherein typically and preferably an effective amount of said inventive composition or said inventive pharmaceutical composition is administered to an equine mammal, preferably to a horse.

In another aspect, the present invention provides for the use of the inventive composition or said inventive pharmaceutical composition for the manufacture of a medicament for the prevention or treatment of pruritus of an equine mammal, preferably of a horse, wherein preferably said pruritus is associated with a pruritic condition or an allergic condition, wherein typically and preferably an effective amount of said inventive composition or said inventive pharmaceutical composition is administered to an equine mammal, preferably to a horse.

Further aspects and embodiments of the present invention will become apparent as this description continues.

Samples from various stages of the inclusion body preparation and purification were applied to a 4-12% Bis-Tris Gel (NuPAGE, Novex, Invitrogen Life Technologies) and run under reducing conditions. Proteins were stained with Coomassie blue. Lane M, Size Marker (See Blue, prestained, NuPAGE, Novex, Invitrogen Life Technologies), lane 1, Lysate (sample A), lane 2, soluble fraction (sample B), lane 3, solubilized inclusion bodies (sample C), lane 4, eIL-31 monomer (eIL-31, m) eluate from Ni-NTA column (sample E).

Figure 2A:
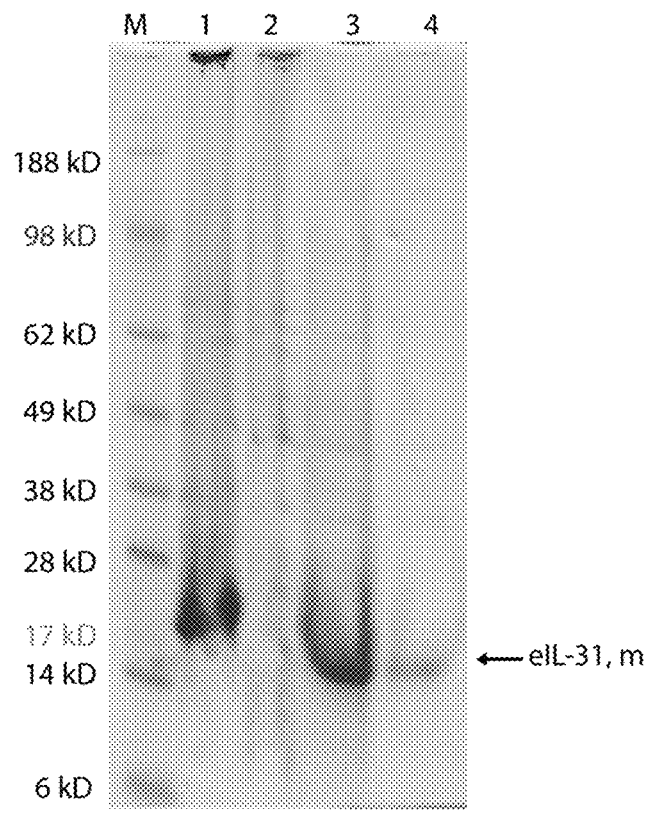
FIG. 2A: SDS-PAGE refolded recombinant eIL-31-C-His.
Figure 2B:
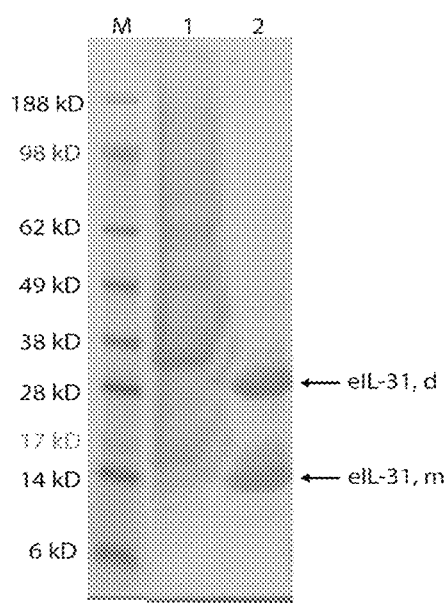

FIG. 2B: Correct structure of refolded recombinant eIL-31-C-His.

Protein was refolded and concentrated as described above. An aliquot was separated on a 4-12% Bis-Tris Gel (NuPAGE, Novex, Invitrogen Life Technologies) and run under native conditions (+SDS, no DTT, no heating). Proteins were stained with Coomassie blue. Lane M, Size Marker (See Blue, prestained, NuPAGE, Novex, Invitrogen Life Technologies), lane 1, pooled eluate from Ni-NTA column, lane 2, refolded eIL-31-C-His.

Figure 2C:
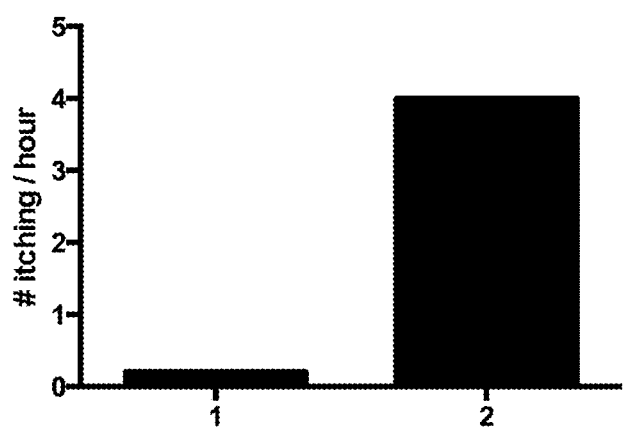

FIG. 2C: Biological activity of recombinant refolded equine eIL-31-C-His. Number of itching on injection site. Bar 1, eIL-5—C-His control, bar 2, eIL-31-C-His.

Figure 3A:
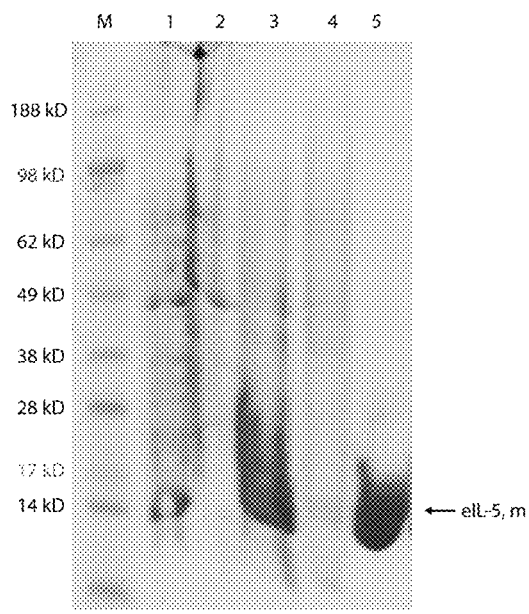

FIG. 3A: SDS-PAGE analysis of the purification of eIL-5—C-His with NiNTA. Samples from various stages of the inclusion body preparation and purification were applied to a 4-12% Bis-Tris Gel (NuPAGE, Novex, Invitrogen Life Technologies) and run under reducing conditions. Proteins were stained with Coomassie blue. Lane M, Size Marker (See Blue, pre-stained, NuPAGE, Novex, Invitrogen Life Technologies), lane 1, Lysate (sample A), lane 2, soluble fraction (sample B), lane 3, solubilized inclusion bodies (sample C), lane 4, flow through (unbound material, sample D), lane 5, pooled eIL-5 monomer (eIL-5, m) eluate from Ni-NTA column (sample E).

Figure 3B:
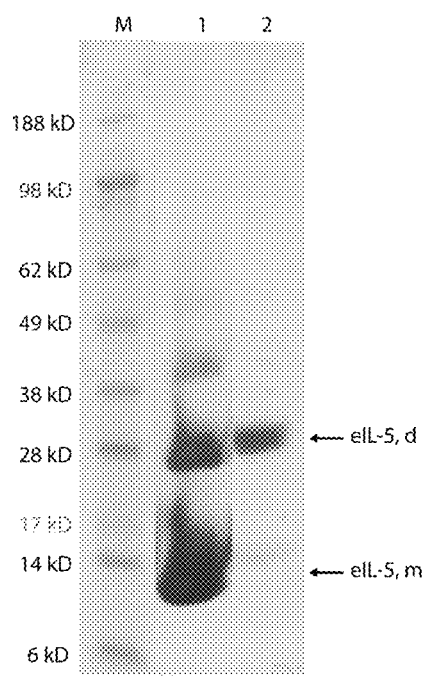

FIG. 3B: SDS-PAGE refolded recombinant eIL-5-C-His. Protein was refolded and concentrated as described above. An aliquot was separated on a 4-12% Bis-Tris Gel (NuPAGE, Novex, Invitrogen Life Technologies) and run under native conditions (+SDS, no DTT, no heating). Proteins were stained with Coomassie blue: eIL-5 monomer (eIL-5, m), eIL-5 dimer (eIL-5, d). Lane M, Size Marker (See Blue, pre-stained, NuPAGE, Novex, Invitrogen Life Technologies), lane 1, pooled denatured eluate from Ni-NTA column, lane 2, refolded and homodimer enriched eIL-5-C-His.

Figure 3C:
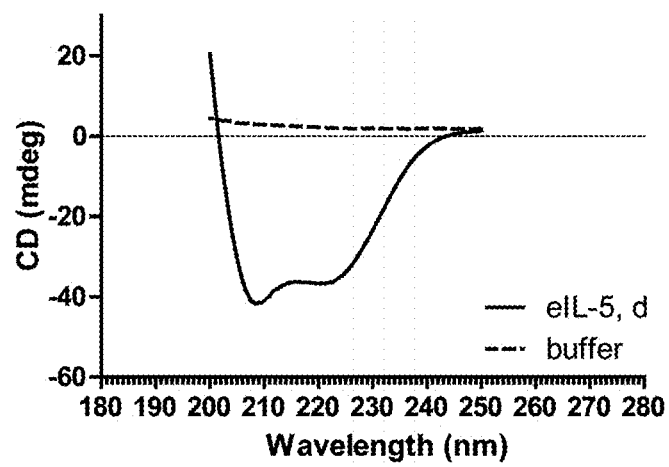

FIG. 3C: Correct structure of refolded recombinant eIL-5-C-His. Circular dichroism (CD) spectroscopy of refolded and homodimer enriched eIL-5-C-His in comparison to PBS buffer (dotted line). Secondary structure of IL-5—C-His reflecting α-helices and β-sheets measured by far-UV (ultraviolet) CD spectra.

Figure 3D:
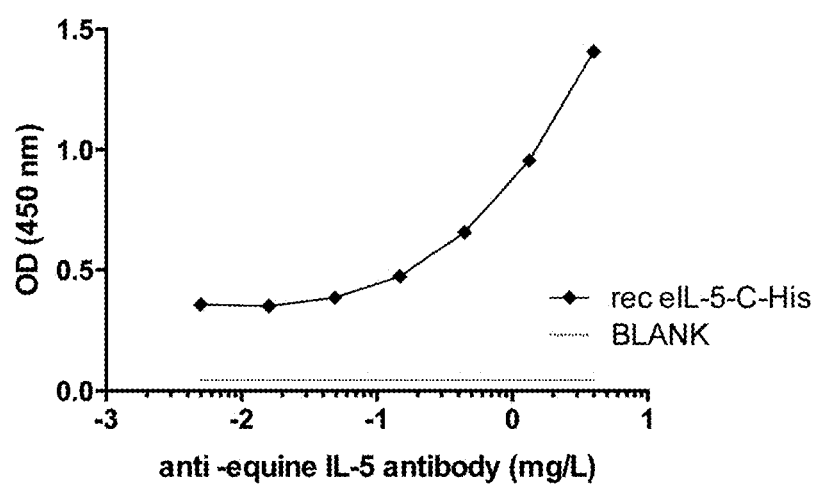

FIG. 3D: Correct structure of refolded recombinant eIL-5—C-His. Homodimer enriched eIL-5—C-His can be detected by a commercially available anti-eIL-S antibody. Anti-His antibody coated ELISA plates were incubated with recombinantly expressed and refolded homodimer enriched eIL-5 and detected by a commercially available anti-equine IL-5 antibody (R&D Systems, UK).

Figure 4A:
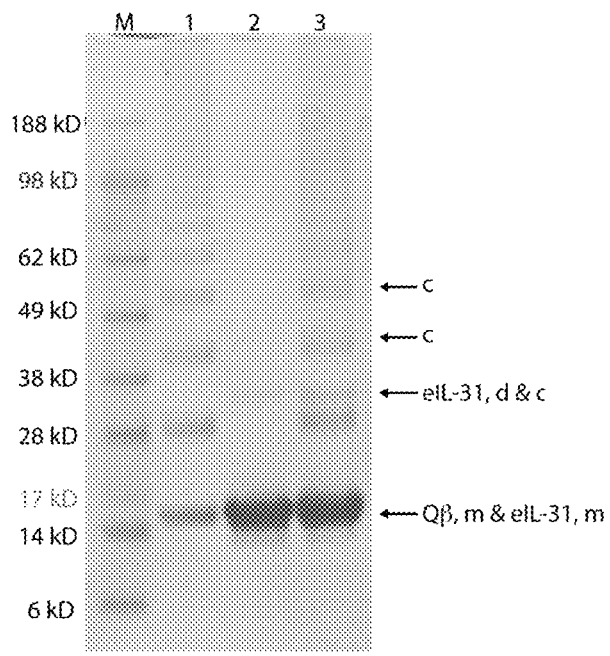

FIG. 4A: Analysis of coupling reaction of eIL-31-C-His-Qβ. By SDS-PAGE. Proteins were stained with Coomassie blue: eIL-31 monomer (eIL-31, m), eIL-31 dimer (eIL-31, d), Qβ monomer (Qβ, m) coupling (c). Lane M, Size Marker (See Blue, prestained, NuPAGE, Novex, Invitrogen Life Technologies), lane 1, Qβ-VLP after derivatization with the chemical crosslinker SMPH, lane 2, TCEP activated eIL-31-C-His, lane 3, eIL-31-C-His-Qβ coupling reaction.

Figure 4B:
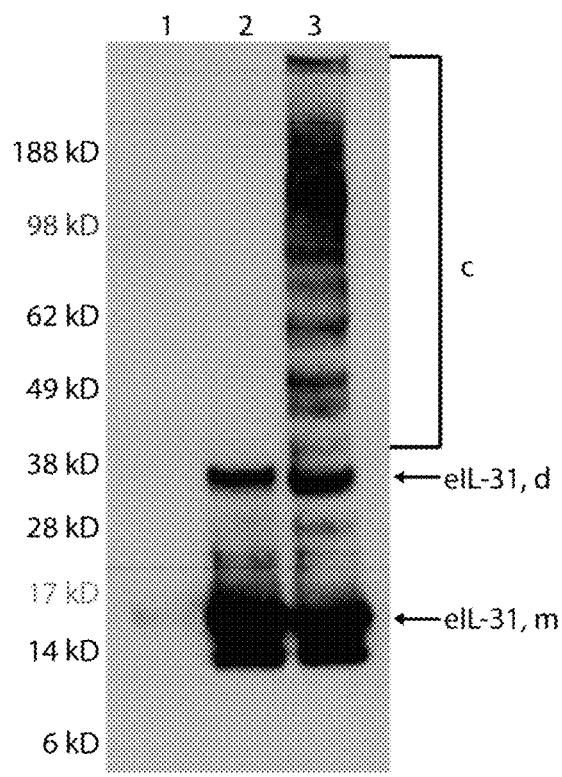

FIG. 4B: Analysis of coupling reaction of eIL-31-C-His-Qβ. By Western-blot. Stained with α-His antibody: eIL-31 monomer (eIL-31, m), eIL-31 dimer (eIL-31, d), coupling (c). Lane M, Size Marker (See Blue, prestained, NuPAGE, Novex, Invitrogen Life Technologies), lane 1, Qβ-VLP after derivatization with the chemical crosslinker SMPH, lane 2, TCEP activated eIL-31-C-His, lane 3, eIL-31-C-His-Qβ coupling reaction.

Figure 4C:
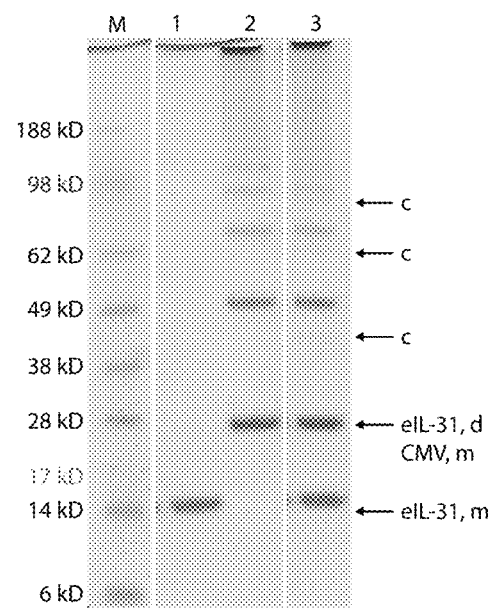

FIG. 4C: Analysis of coupling reaction of eIL-31-C-His-CMVtt830. By SDS-PAGE. Proteins were stained with Coomassie blue: eIL-31 monomer (eIL-31, m), CMVtt830 monomer (CMV, m), coupling (c). Lane M, Size Marker (See Blue, prestained, NuPAGE, Novex, Invitrogen Life Technologies), lane 1, TCEP activated eIL-31-C-His, lane 2, CMVtt830-VLP after derivatization with the chemical crosslinker SMPH, lane 3, eIL-31-C-His-CMVtt830 coupling reaction.

Figure 4D:
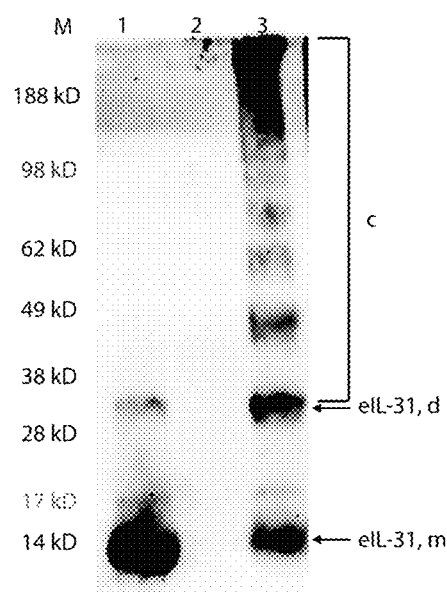

FIG. 4D: Analysis of coupling reaction of eIL-31-C-His-CMVtt830. By Western-blot. Stained with α-His antibody: eIL-31 monomer (eIL-31, m), eIL-31 dimer (eIL-31, d), coupling (c). Lane M, Size Marker (See Blue, prestained, NuPAGE, Novex, Invitrogen Life Technologies), lane 1, TCEP activated eIL-31-C-His, lane 2, CMVtt830-VLP after derivatization with the chemical crosslinker SMPH, lane 3, eIL-31-C-His-CMVtt830 coupling reaction.

Figure 5A:
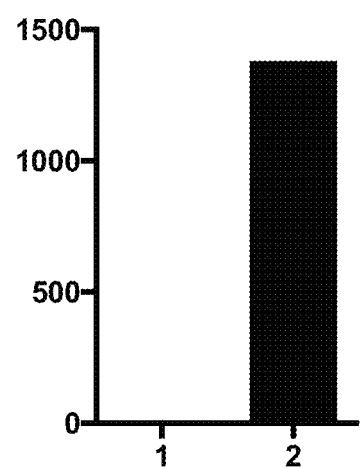

FIG. 5A: ELISA of Antibody titer in horses from sera. Pre-immune (1, day 0) and serum after $2^{nd}$ vaccination (2, day 41) with eIL-31-C-His-CMVtt830 vaccine of one horse was collected. Y-axis shows OD50 anti-IL-31 IgG antibody titer.

Figure 5B:
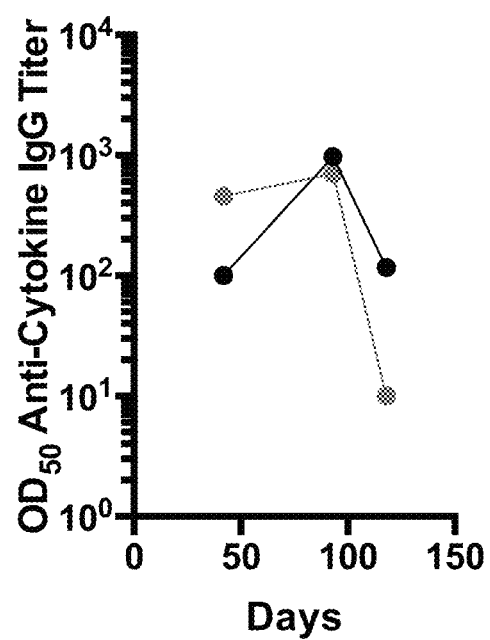

FIG. 5B: ELISA of Antibody titer in horses from sera. Pre-immune and serum after $2^{nd}$ vaccination (days 42, 93, and 118) with eIL-5-C-His-Qβ and eIL-31-C-His-Qβ vaccines of one horse was collected. Sera were analyzed for antibodies against eIL-5 and eIL-31. Horse has been immunized on days −62 and −40 by eIL-5-C-His-Qβ and on days 0 and 19 by eIL-31-C-His-Qβ. Data shows OD50 values for sera subtracted by pre-immune values. Anti-IL-5 antibody titer in black circles and anti-IL-31 antibody titer in grey circles.

Figure 5C:
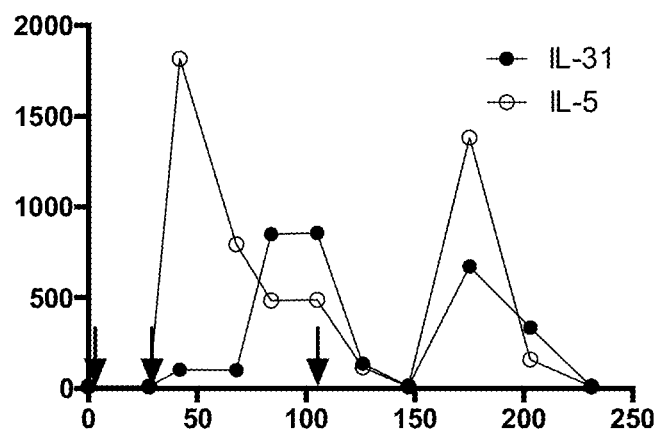

FIG. 5C: ELISA of Antibody titer in horses from sera. Pre-immune and serum after $2^{nd}$ vaccination (several days after day 28) with eIL-5—C-His-CMVtt830 and eIL-31-C-His-CMVtt830 vaccines of horse was collected. Sera were analyzed for antibodies against eIL-5 and eIL-31. Horse has been immunized on days 0, 28 and 105 by eIL-5—C-His-CMVtt830 and eIL-31-C-His-CMVtt830. Data shows OD50 values for sera subtracted by pre-immune values. Anti-eIL-S antibody titer in open circles and anti-eIL-31 antibody titer in filled circles. Y-axis shows OD50 anti-eIL-S/or anti-eIL-31 IgG antibody titer.

Figure 5D:
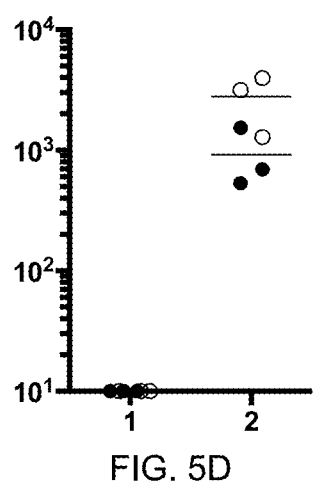

FIG. 5D: ELISA of Antibody titer in horses from sera. Pre-immune and serum after $2^{nd}$ vaccination (day 42) with eIL-31-C-His-CMVtt830 and eIL-31-C-His-CMVtt830 vaccines of horses that had been vaccinated with both vaccines at the same day but on different body sites. Sera were analyzed for antibodies against eIL-5 and eIL-31. Horses had been immunized on days 0 and 28 by eIL-5—C-His-CMVtt830 (left side) and eIL-31-C-His-CMVtt830 (right side). Data shows OD50 values for sera subtracted by pre-immune values. Anti-eIL-5 antibody titer in open circles and anti-eIL-31 antibody titer in filled circles. Y-axis shows OD50 anti-eIL-5/or anti-eIL-31 IgG antibody titer, x-axis, 1, pre-immune sera day 0, 2, post $2^{nd}$ vaccination day 42, n=3.

Figure 5E:
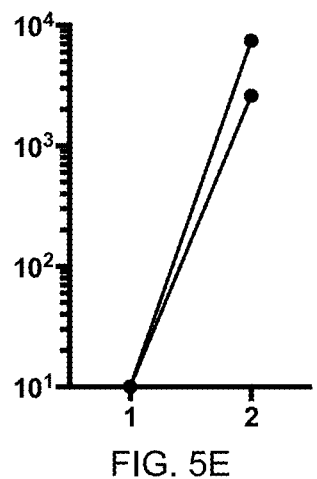

FIG. 5E: ELISA of Antibody titer in horses from sera. Pre-immune and serum after $2^{nd}$ vaccination (day 42) with eIL-31-C-His-CMVtt830 vaccine of that had been vaccinated in the previous year with eIL-5—C-His-CMVtt830. Sera were analyzed for antibodies against eIL-31. Horses had been immunized on days 0 and 28 by eIL-31-C-His-CMVtt830. Data shows OD50 values for sera subtracted by pre-immune values. Y-axis shows OD50 anti-IL-31 IgG antibody titer, x-axis, 1, pre-immune sera day 0, 2, post $2^{nd}$ vaccination day 42, n=2.

Figure 5F:
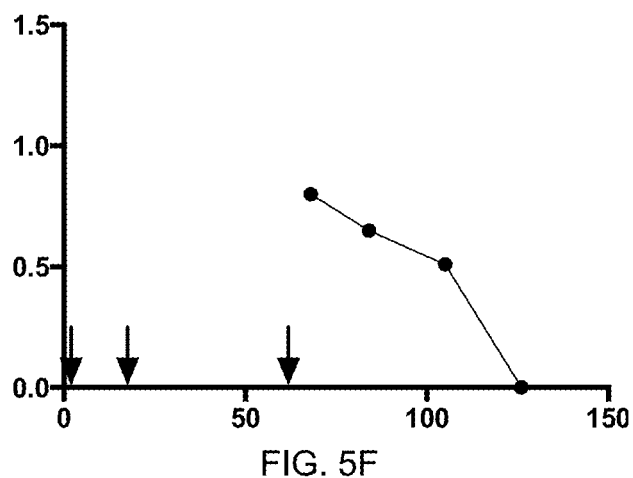

FIG. 5F: Reduction of eosinophil levels in blood (y-axis, in ×10E09 cells/L) upon vaccination using eIL-5-CMVtt830 and eIL-31-CMVtt830 combination. X-axis shows days, arrows indicate vaccine injections.

Figure 5G:
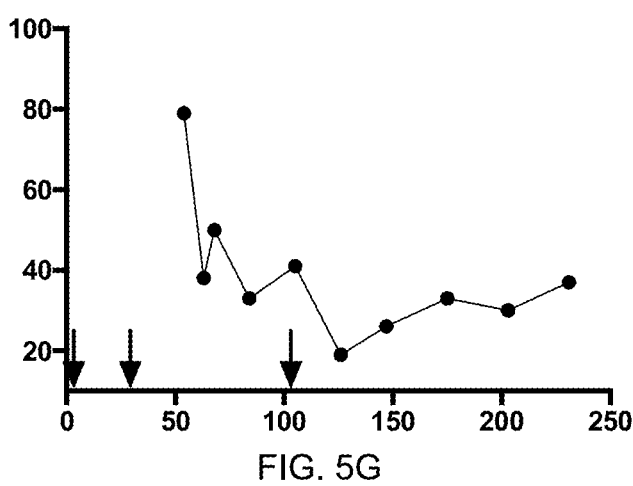

FIG. 5G: Reduction of skin lesion score (y-axis) course over season upon vaccination using eIL-5-CMVtt830 and eIL-31-CMVtt830 combination. X-axis shows days, arrows indicate vaccine injections.

Figure 5H:
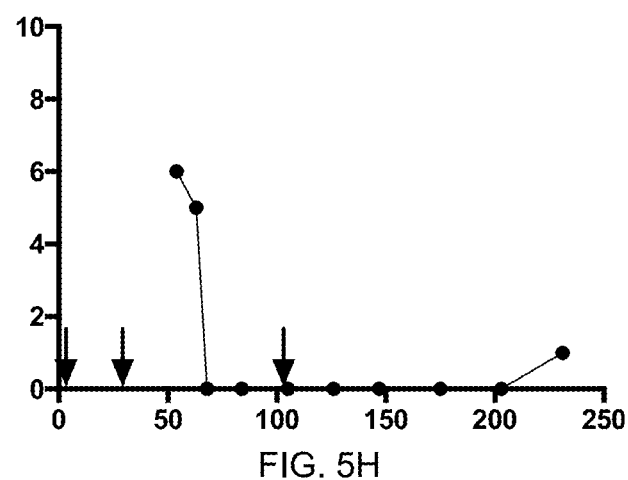

FIG. 5H: Reduction of pruritus score (y-axis) course over season upon vaccination using eIL-5-CMVtt830 and eIL-31-CMVtt830 combination. X-axis shows days, arrows indicate vaccine injections.

Figure 5I:
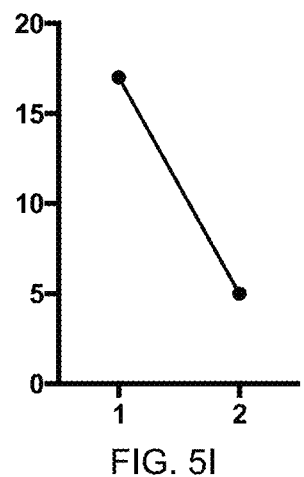

FIG. 5I: Mean pruritus score (y-axis) reduced in treatment season (2) by vaccination using eIL-5-CMVtt830 and eIL-31-CMVtt830 combination when compared to untreated previous season (1).

Figure 5J:
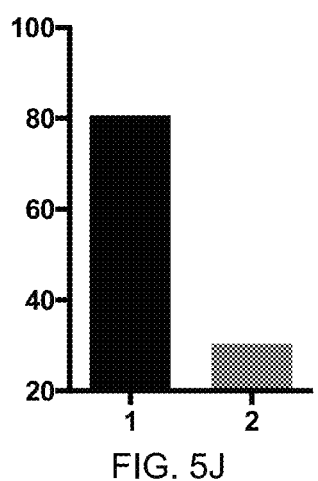

FIG. 5J: Mean skin lesion score (y-axis) reduced in treatment season (2) by vaccination using eIL-31-CMVtt830 when compared to untreated previous season (1).

Figure 5K:
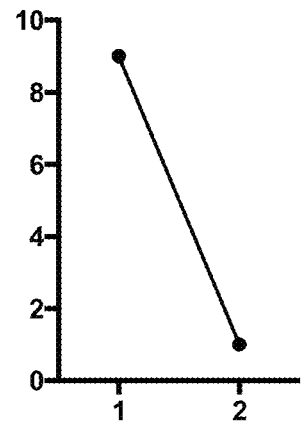

FIG. 5K: Mean pruritus score (y-axis) reduced in treatment season (2) by vaccination using eIL-31-CMVtt830 when compared to untreated previous season (1).

Figure 6A:
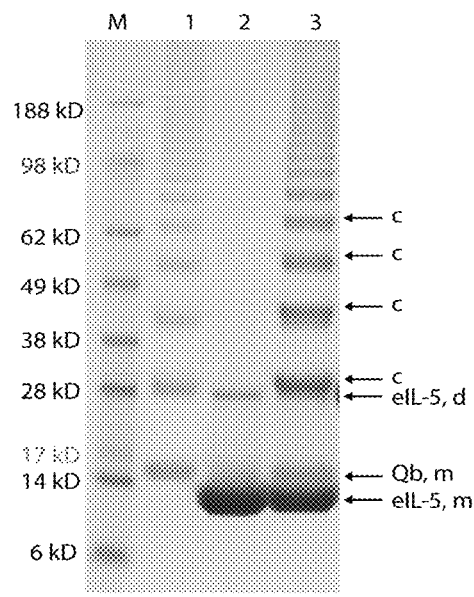

FIG. 6A: Analysis of coupling reaction of eIL-5-C-His-Qβ. By SDS-PAGE. Proteins were stained with Coomassie blue: eIL-5 monomer (eIL-5, m), eIL-5 dimer (eIL-5, d), Qβ monomer (Qβ, m) coupling (c). Lane M, Size Marker (See Blue, prestained, NuPAGE, Novex, Invitrogen Life Technologies), lane 1, Qβ-VLP after derivatization with the chemical crosslinker SMPH, lane 2, TCEP activated eIL-5-C-His, lane 3, eIL-5-C-His-Qβ coupling reaction.

Figure 6B:
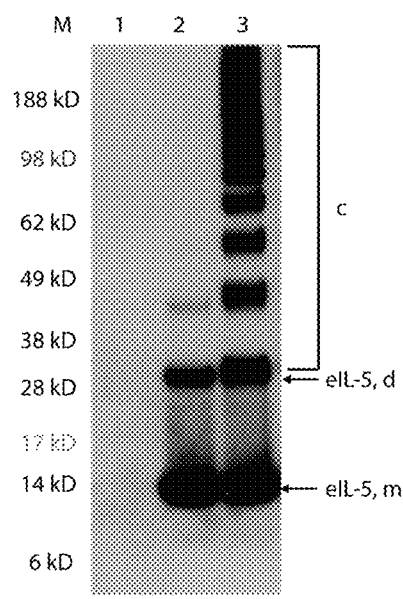

FIG. 6B: Analysis of coupling reaction of eIL-5-C-His-Qβ. By Western-blot. Stained with α-His antibody: eIL-5 monomer (eIL-5, m), eIL-5 dimer (eIL-5, d), coupling (c). Lane M, Size Marker (See Blue, prestained, NuPAGE, Novex, Invitrogen Life Technologies), lane 1, Qβ-VLP after derivatization with the chemical crosslinker SMPH, lane 2, TCEP activated eIL-5-C-His, lane 3, eIL-5-C-His-Qβ coupling reaction.

Figure 6C:
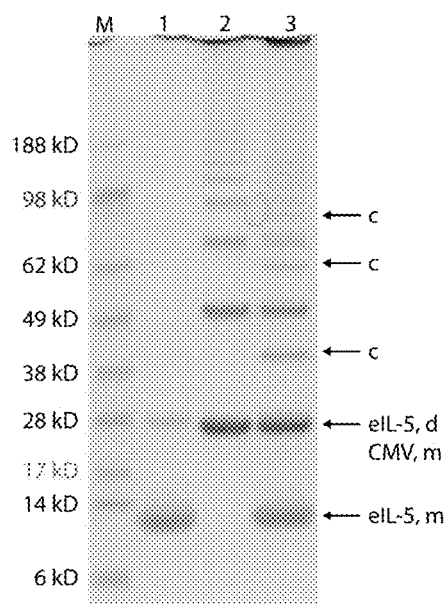

FIG. 6C: Analysis of coupling reaction of eIL-5-C-His-CMVtt830. By SDS-PAGE. Proteins were stained with Coomassie blue: eIL-5 monomer (eIL-5, m), eIL-5 dimer (eIL-5, d), CMV (CMV, m), coupling (c). Lane M, Size Marker (See Blue, prestained, NuPAGE, Novex, Invitrogen Life Technologies), lane 1, CMVtt830-VLP after derivatization with the chemical crosslinker SMPH, lane 2, TCEP activated eIL-5-C-His, lane 3, eIL-5-C-His-CMVtt830 coupling reaction.

Figure 6D:
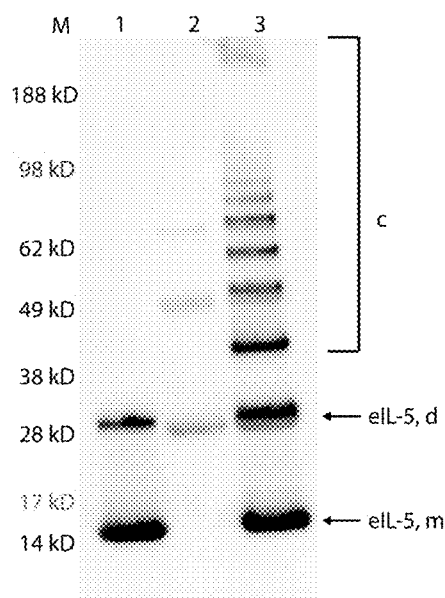

FIG. 6D: Analysis of coupling reaction of eIL-5-C-His-CMVtt830. By Western-blot. Stained with α-His antibody: eIL-5 monomer (eIL-5, m), eIL-5 dimer (eIL-5, d), coupling (c). Lane M, Size Marker (See Blue, prestained, NuPAGE, Novex, Invitrogen Life Technologies), lane 1, CMVtt830-VLP after derivatization with the chemical crosslinker SMPH, lane 2, TCEP activated eIL-5-C-His, lane 3, eIL-5-C-His-CMVtt830 coupling reaction.

Figure 7A:
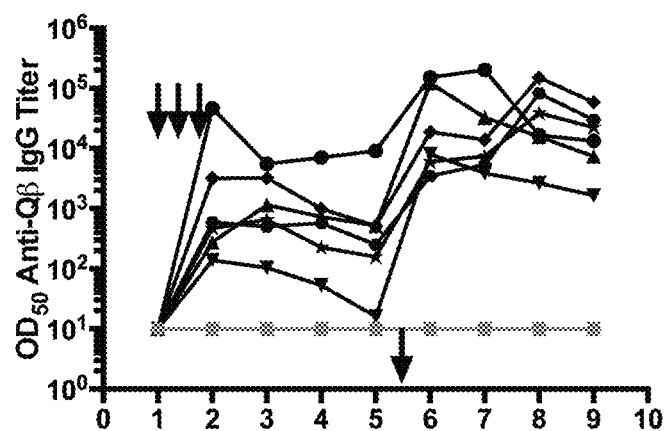

FIG. 7A: Efficient reduction of IBH disease parameters by eIL-5-C-His-Qβ in double-blind placebo controlled randomized study. Time course of antibody titer. Blood samples have been collected at several time points post injections (vaccine injections are indicated by arrows) and sera were analyzed for anti-Qβ IgG antibodies. Data timepoint 1 is 1 Jan. 2015, timepoint 2 is 20 Mar. 2015, timepoint 3 is 3 Apr. 2015, timepoint 4 is 30 Apr. 2015, timepoint 5 is 28 May 2015, timepoint 6 is 25 Jun. 2015, timepoint 7 is 30 Jul.

2015, timepoint 8 is 27 Aug. 2015, timepoint 9 is 30 Sep. 2015 of sera from vaccinated horses (black line) and placebo horses (grey line).

Figure 7B:
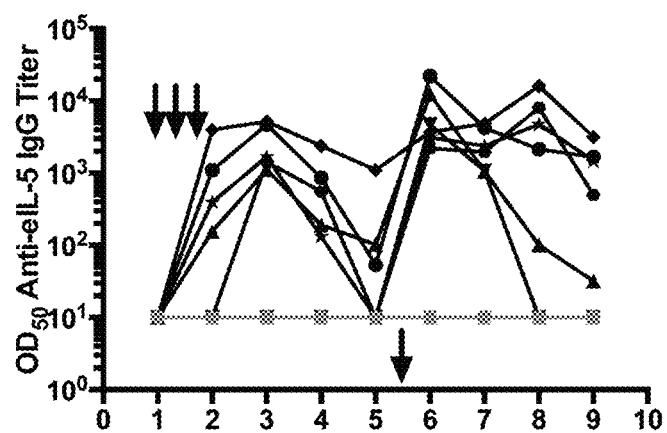

FIG. 7B: Efficient reduction of IBH disease parameters by eIL-5-C-His-Qβ in double-blind placebo controlled randomized study. Time course of antibody titer. Blood samples have been collected at several time points post injections (vaccine injections are indicated by arrows) and sera were analyzed for anti-eIL-5 IgG self-antibodies. Data timepoint 1 is 1 Jan. 2015, timepoint 2 is 20 Mar. 2015, timepoint 3 is 3 Apr. 2015, timepoint 4 is 30 Apr. 2015, timepoint 5 is 28 May 2015, timepoint 6 is 25 Jun. 2015, timepoint 7 is 30 Jul. 2015, timepoint 8 is 27 Aug. 2015, timepoint 9 is 30 Sep. 2015 of sera from vaccinated horses (black line) and placebo horses (grey line).

Figure 7C:
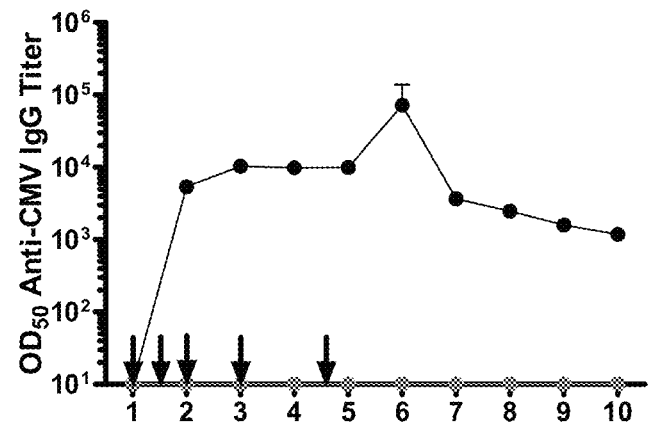

FIG. 7C: Efficient reduction of IBH disease parameters by eIL-5—C-His-CMVtt830 in double-blind placebo controlled randomized study. Time course of mean antibody titer (+/−SEM). Blood samples have been collected at several time points post injections (vaccine injections are indicated by arrows) and sera were analyzed for anti-CMV IgG antibodies. Data timepoint 1 is January 2016, timepoint 2 is beginning of March 2016, timepoint 3 is end of March 2016, timepoint 4 is April 2016, timepoint 5 is May 2016, timepoint 6 is June 2016, timepoint 7 is July 2016, timepoint 8 is August 2016, timepoint 9 is September 2016, timepoint 10 is October 2016 of sera from vaccinated horses (black line) and placebo horses (grey line).

Figure 7D:
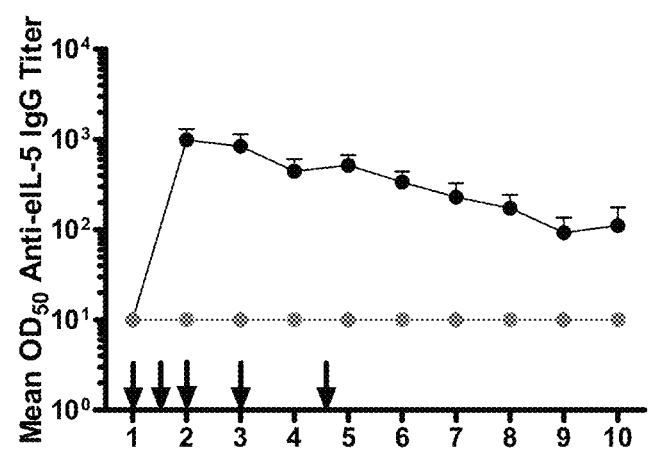

FIG. 7D: Efficient reduction of IBH disease parameters by eIL-5—C-His-CMVtt830 in double-blind placebo controlled randomized study. Time course of mean antibody titer (+/−SEM). Blood samples have been collected at several time points post injections (vaccine injections are indicated by arrows) and sera were analyzed for anti-eIL-S IgG self-antibodies. Data timepoint 1 is January 2016, timepoint 2 is beginning of March 2016, timepoint 3 is end of March 2016, timepoint 4 is April 2016, timepoint 5 is May 2016, timepoint 6 is June 2016, timepoint 7 is July 2016, timepoint 8 is August 2016, timepoint 9 is September 2016, timepoint 10 is October 2016 of sera from vaccinated horses (black line) and placebo horses (grey line).

Figure 7E:
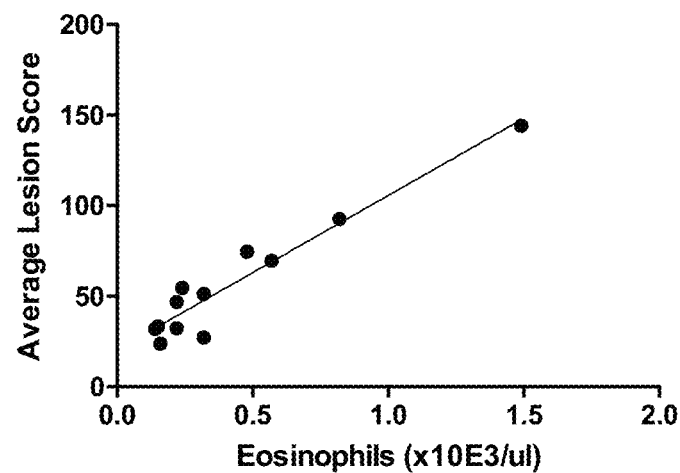

FIG. 7E: Correlation of disease symptoms to eosinophil levels in blood. Eosinophil levels of 12 sweet itch affected horses were measured in the blood and were blotted against disease symptom scoring of IBH lesions during the season. Correlation precision is shown by $R^2=0.9227$, $p<0.0001$, n=12.

Figure 7F:
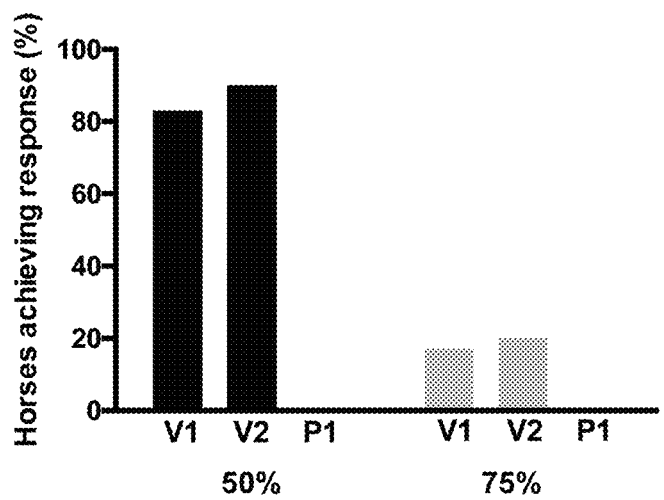

FIG. 7F: Efficient reduction of IBH disease parameters by eIL-5-C-His-Qβ in double-blind placebo controlled randomized study & follow-up study. Percentage of eIL-5-C-His-Qβvaccinated horses (V) and placebo horses (P) that achieve 50% (black bars) or 75% (grey bars) improvement in clinical score comparing treatment year to pre-evaluation year, respectively. V1 includes horses that received vaccine in the first treatment year (n=6 in double-blind placebo controlled randomized study) and V2 includes all horses that received vaccine, either twice (first and follow-up year) or once (follow-up year) in the first year treatment and the follow-up year (total: n=10; n=6 vaccination in first and follow-up year, n=4 vaccination in follow-up year). Graph include all horses, n=10, independent of antibody titer: ITT=intention to treat.

Figure 7G:
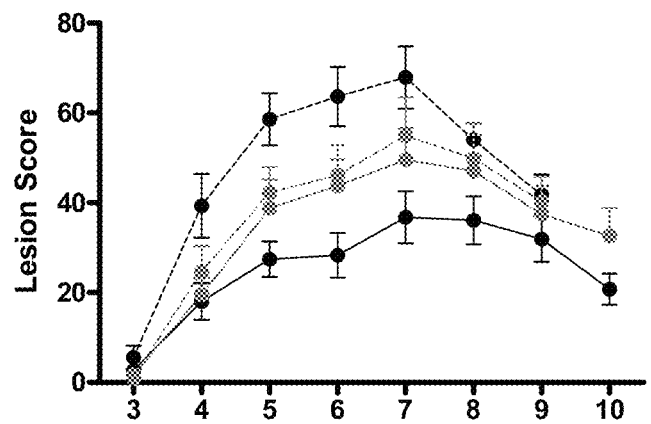

FIG. 7G: Efficient reduction of IBH disease parameters by eIL-5-C-His-CMVtt830 in double-blind placebo controlled randomized study. Time course of lesion score Lesion scores were evaluated at several time points during the pre-evaluation year (dotted line) and treatment year (continuous line) showing vaccinated horses in black lines and placebo horses in grey lines. Data timepoint 1 is January 2016, timepoint 2 is beginning of March 2016, timepoint 3 is end of March 2016, timepoint 4 is April 2016, timepoint 5 is May 2016, timepoint 6 is June 2016, timepoint 7 is July 2016, timepoint 8 is August 2016, timepoint 9 is September 2016, timepoint 10 is October 2016.

Figure 7H:
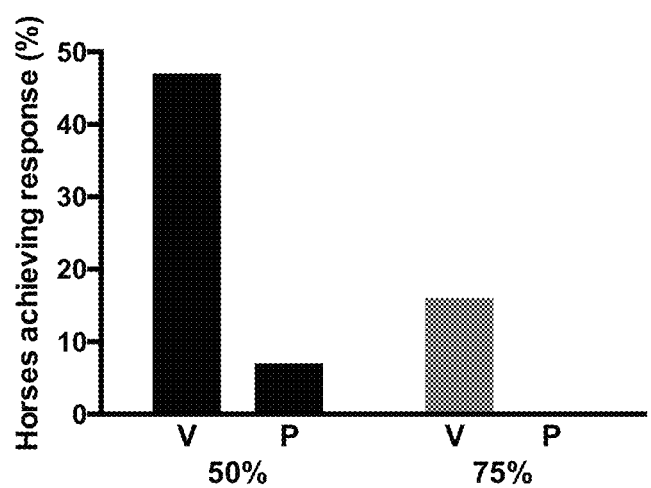

FIG. 7H: Efficient reduction of IBH disease parameters by eIL-5—C-His-CMVtt830 in double-blind placebo controlled randomized study. Percentage of eIL-5-CMVtt830 vaccinated horses (V) and placebo horses (P) that achieve 50% (black bars) or 75% (grey bars) improvement in clinical score comparing treatment year to pre-evaluation year, respectively. Graph include all horses, n=34, independent of antibody titer: ITT=intention to treat.

Figure 8A:
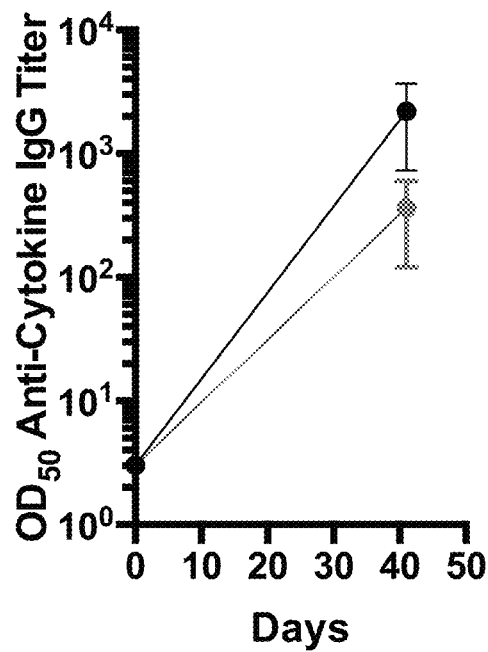

FIG. 8A: ELISA of Antibody titer in mice from sera. Pre-immune and serum post immune from day 41, after vaccination with either mIL-5-C-His-Qβ vaccine alone (black circles) or mIL-31-C-His-CMVtt830 vaccine alone (grey circle) of 10 mice each was collected. Sera were analyzed for antibodies against eIL-5 (black circle) and eIL-31 (grey circle). Mice have been immunized on days 0, 14, and 28. Data shows OD50 values for sera. Anti-IL-5 antibody titer of mIL-5-C-His-Qβ vaccinated mice in black circles and anti-IL-31 antibody titer of mIL-31-C-His-CMVtt830 vaccinated mice in grey circles.

Figure 8B:
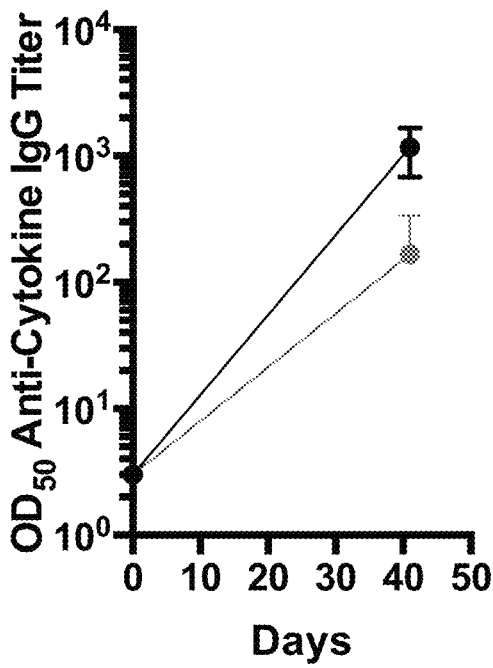

FIG. 8B: ELISA of Antibody titer in mice from sera. Pre-immune and serum post immune from day 41, after vaccination with mIL-5-C-His-Qβ/mIL-31-C-His-CMVtt830 combination vaccination 5 mice each was collected. Sera were analyzed for antibodies against eIL-5 (black circle) and eIL-31 (grey circle). Mice have been immunized on days 0, 14, and 28. Data shows OD50 values for sera. Anti-IL-5 antibody titer o in black circles and anti-IL-31 antibody titer in grey circles.

Figure 8C:
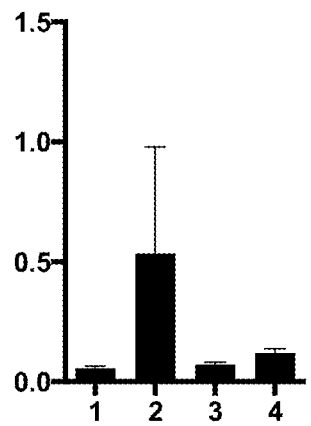

FIG. 8C: Murine IL-31 mRNA levels, shown as per mille expression of murine βactin housekeeping gene (y-axis) in ova allergic mice vaccinated with mIL-31-CMV and ova challenge (1), with CMV VLP and ova challenge (2), with mIL-5-Qβ & mIL-31-CMVtt830 combination and ova challenge (3), and with CMV VLP and PBS control challenge (4). Mean+SEM is shown, n=6.

Figure 8D:
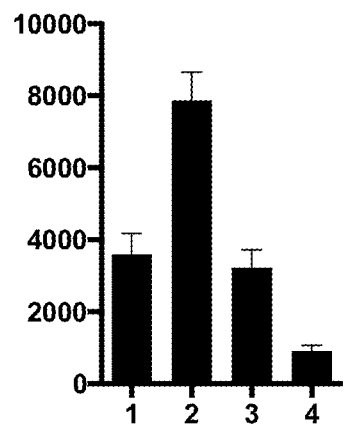

FIG. 8D: ELISA of anti-ova IgG Antibody titer in mice from sera. Pre-immune and serum at the endpoint of experiment (day 22 of allergic dermatitis model) in ova sensitized mice additionally vaccinated with mIL-31-CMV and ova challenge (1), with CMV VLP and ova challenge (2), with mIL-5-Qβ & mIL-31-CMVtt830 combination and ova challenge (3), and with CMV VLP and PBS control challenge (4). Data shows OD50 values for sera subtracted by pre-immune values, mean+SEM, n=6. Y-axis shows OD50 anti-ova IgG antibody titer.

Figure 8E:
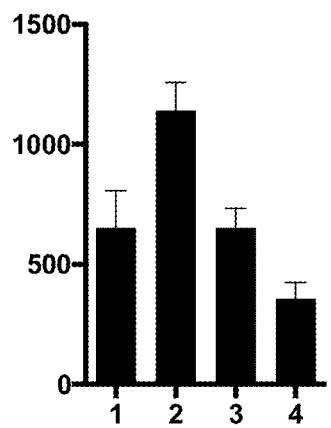

FIG. 8E: ELISA of anti-ova IgE Antibody titer in mice from sera. Pre-immune and serum at the endpoint of experiment (day 22 of allergic dermatitis model) in ova sensitized mice additionally vaccinated with mIL-31-CMV and ova challenge (1), with CMV VLP and ova challenge (2), with mIL-5-Qβ & mIL-31-CMVtt830 combination and ova challenge (3), and with CMV VLP and PBS control challenge (4). Data shows OD50 values for sera subtracted by pre-immune values, mean+SEM, n=6. Y-axis shows OD50 anti-ova IgE antibody titer.

Figure 8F:
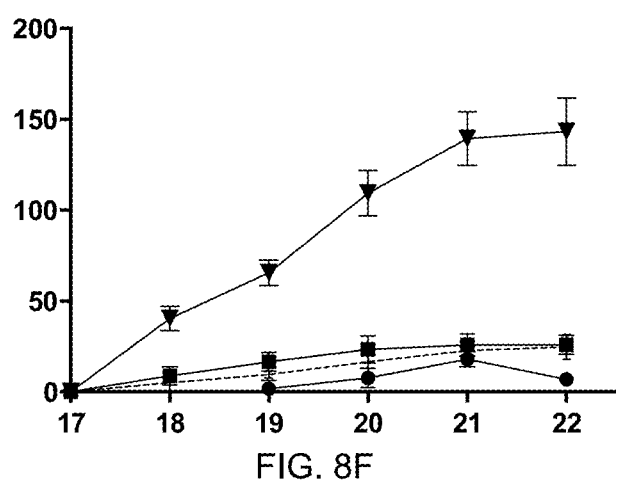

FIG. 8F: Percentage of increase of ear thickness (y-axis) upon ova challenge on the skin of the left ear shown on days 17, 18, 19, 20, 21, and 22 (x-axis). Group 1 vaccinated with mIL-31-C-His-CMVtt830 alone and ova challenge (filled circle); group 2 vaccinated against CMVtt830 VLP and ova challenge (triangle); group 3 vaccinated with mIL-5C-His-Qβ & mIL-31-C-His-CMVtt830 combination and ova challenge (square); and group 4 vaccinated with CMVtt830 VLP and PBS control challenge (dotted line). Mean+/−SEM, n=6 mice.

DETAILED DESCRIPTION OF THE INVENTION

Unless defined otherwise, all technical and scientific terms used herein have the same meanings as commonly understood by one of ordinary skill in the art to which this invention belongs.

Virus-like particle (VLP): The term "virus-like particle (VLP)" as used herein, refers to a non-replicative or non-infectious, preferably a non-replicative and non-infectious virus particle, or refers to a non-replicative or non-infectious, preferably a non-replicative and non-infectious structure resembling a virus particle, preferably a capsid of a virus. The term "non-replicative", as used herein, refers to being incapable of replicating the genome comprised by the VLP. The term "non-infectious", as used herein, refers to being incapable of entering the host cell. A virus-like particle in accordance with the invention is non-replicative and non-infectious since it lacks all or part of the viral genome or genome function. A virus-like particle in accordance with the invention may contain nucleic acid distinct from their genome. Recombinantly produced virus-like particles typically contain host cell derived RNA. A typical and preferred embodiment of a virus-like particle in accordance with the present invention is a viral capsid composed of polypeptides of the invention. A virus-like particle is typically a macromolecular assembly composed of viral coat protein which typically comprises 60, 120, 180, 240, 300, 360, or more than 360 protein subunits per virus-like particle. Typically and preferably, the interactions of these subunits lead to the formation of viral capsid or viral-capsid like structure with an inherent repetitive organization. One feature of a virus-like particle is its highly ordered and repetitive arrangement of its subunits.

Virus-like particle of an RNA bacteriophage: As used herein, the term "virus-like particle of an RNA bacteriophage" refers to a virus-like particle comprising, or preferably consisting essentially of or consisting of coat proteins, mutants or fragments thereof, of an RNA bacteriophage. In addition, virus-like particle of an RNA bacteriophage resembling the structure of an RNA bacteriophage, being non replicative and/or non-infectious, and lacking at least the gene or genes encoding for the replication machinery of the RNA bacteriophage, and typically also lacking the gene or genes encoding the protein or proteins responsible for viral attachment to or entry into the host. Also included are virus-like particles of RNA bacteriophages, in which the aforementioned gene or genes are still present but inactive, and, therefore, also leading to non-replicative and/or non-infectious virus-like particles of an RNA bacteriophage. Preferred VLPs derived from RNA bacteriophages exhibit icosahedral symmetry and consist of 180 subunits (monomers). Preferred methods to render a virus-like particle of an RNA bacteriophage non replicative and/or non-infectious is by physical, chemical inactivation, such as UV irradiation, formaldehyde treatment, typically and preferably by genetic manipulation.

Virus-like particle of CMV: The terms "virus-like particle of CMV" or CMV VLPs refer to a virus-like particle comprising, or preferably consisting essentially of, or preferably consisting of at least one CMV polypeptide. Preferably, a virus-like particle of CMV comprises said CMV polypeptide as the major, and even more preferably as the sole protein component of the capsid structure. Typically and preferably, virus-like particles of CMV resemble the structure of the capsid of CMV. Virus-like particles of CMV are non-replicative and/or non-infectious, and lack at least the gene or genes encoding for the replication machinery of the CMV, and typically also lack the gene or genes encoding the protein or proteins responsible for viral attachment to or entry into the host. This definition includes also virus-like particles in which the aforementioned gene or genes are still present but inactive. Preferred methods to render a virus-like particle of CMV non replicative and/or non-infectious is by physical or chemical inactivation, such as UV irradiation, formaldehyde treatment. Preferably, VLPs of CMV lack the gene or genes encoding for the replication machinery of the CMV, and also lack the gene or genes encoding the protein or proteins responsible for viral attachment to or entry into the host. Again more preferably, non-replicative and/or non-infectious virus-like particles are obtained by recombinant gene technology. Recombinantly produced virus-like particles of CMV according to the invention typically and preferably do not comprise the viral genome. Virus-like particles comprising more than one species of polypeptides, often referred to as mosaic VLPs are also encompassed by the invention. Thus, in one embodiment, the virus-like particle according to the invention comprises at least two different species of polypeptides, wherein at least one of said species of polypeptides is a CMV polypeptide. Preferably, a VLP of CMV is a macromolecular assembly composed of CMV coat protein which typically comprises 180 coat protein subunits per VLP. Typically and preferably, a VLP of CMV as used herein, comprises, essentially consists of, or alternatively consists of, at least one CMV polypeptide comprising or preferably consisting of (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said amino acid sequence to be mutated show a sequence identity of at least 90%, preferably of at least 95%, further preferably of at least 98% and again more preferably of at least 99%.

Antigen: As used herein, the term "antigen" refers to a molecule capable of being bound by an antibody or a T-cell receptor (TCR) if presented by MHC molecules. The term "antigen", as used herein, also refers to T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and/or is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. If not indicated otherwise, the term "antigen" as used herein does not refer to the core particle or virus-like particle contained in the inventive compositions, immunogenic or vaccine compositions and/or pharmaceutical compositions.

Coat protein: The term "coat protein" refers to a viral protein, preferably to a subunit of a natural capsid of a virus, preferably of an RNA bacteriophage or a plant virus, which is capable of being incorporated into a virus capsid or a VLP. The term coat protein encompasses naturally occurring coat protein as well as recombinantly expressed coat protein. Further encompassed are mutants and fragments of coat protein, wherein said mutants and fragments retains the capability of forming a VLP.

Polypeptide: The term "polypeptide" as used herein refers to a polymer composed of amino acid monomers which are linearly linked by peptide bonds (also known as amide bonds). The term polypeptide refers to a consecutive chain of amino acids and does not refer to a specific length of the product. Thus, peptides, and proteins are included within the definition of polypeptide.

Cucumber Mosaic Virus (CMV) polypeptide: The term "cucumber mosaic virus (CMV) polypeptide" as used herein refers to a polypeptide comprising or preferably consisting of: (i) an amino acid sequence of a coat protein of cucumber mosaic virus (CMV), or (ii) a mutated amino acid sequence, wherein the amino acid sequence to be mutated is an amino acid sequence of a coat protein of CMV, and wherein said mutated amino acid sequence and said amino acid sequence to be mutated, i.e. said coat protein of CMV, show a sequence identity of at least 90%, preferably of at least 95%, further preferably of at least 98% and again more preferably of at least 99%. Typically and preferably, the CMV polypeptide is capable of forming a virus-like particle of CMV upon expression by self-assembly.

Coat protein (CP) of cucumber mosaic virus (CMV): The term "coat protein (CP) of cucumber mosaic virus (CMV)", as used herein, refers to a coat protein of the cucumber mosaic virus which occurs in nature. Due to extremely wide host range of the cucumber mosaic virus, a lot of different strains and isolates of CMV are known and the sequences of the coat proteins of said strains and isolates have been determined and are, thus, known to the skilled person in the art as well. The sequences of said coat proteins (CPs) of CMV are described in and retrievable from the known databases such as Genbank, www.dpvweb.net, or www.ncbi.nlm.nih.gov/protein/. Examples are described in EP Application No. 14189897.3. Further examples of CMV coat proteins are provided in SEQ ID NOs 15-17. It is noteworthy that these strains and isolates have highly similar coat protein sequences at different protein domains, including the N-terminus of the coat protein. In particular, 98.1% of all completely sequenced CMV isolates share more than 85% sequence identity within the first 28 amino acids of their coat protein sequence, and still 79.5% of all completely sequenced CMV isolates share more than 90% sequence identity within the first 28 amino acids of their coat protein sequence.

Typically and preferably, the coat protein of CMV used for the present invention is capable of forming a virus-like particle of CMV upon expression by self-assembly. Preferably, the coat protein of CMV used for the present invention is capable of forming a virus-like particle of CMV upon expression by self-assembly in E. coli.

Modified virus-like particle (VLP) of cucumber mosaic virus (CMV): The term "modified virus-like particle (VLP) of cucumber mosaic virus (CMV)" as used herein, refers to a VLP of CMV which is a modified one in such as it comprises, or preferably consists essentially of, or preferably consists of at least one modified CMV polypeptide, wherein said modified CMV polypeptide comprises, or preferably consists of, a CMV polypeptide, and a T helper cell epitope. Typically and preferably, said T helper cell epitope (i) is fused to the N-terminus of said CMV polypeptide, (ii) is fused to the C-terminus of said CMV polypeptide, (iii) replaces a region of consecutive amino acids of said CMV polypeptide, wherein the sequence identity between said replaced region of consecutive amino acids of said CMV polypeptide and the T helper cell epitope is at least 15%, preferably at least 20%, or (iv) replaces a N-terminal region of said CMV polypeptide, and wherein said replaced N-terminal region of said CMV polypeptide consists of 5 to 15 consecutive amino acids. Preferably, said T helper cell epitope replaces a N-terminal region of said CMV polypeptide, and wherein said replaced N-terminal region of said CMV polypeptide consists of 5 to 15 consecutive amino acids, preferably of 9 to 14 consecutive amino acids, more preferably of 11 to 13 consecutive amino acids, and most preferably of 11, 12 or 13 consecutive amino acids. Preferably said modified VLP of CMV of the present invention is a recombinant modified VLP of CMV.

Modified CMV polypeptide: The term "modified CMV polypeptide" as used herein refers to a CMV polypeptide modified in such as defined herein, that said modified CMV polypeptide comprises, or preferably consists of, a CMV polypeptide, and a T helper cell epitope. Typically, the modified CMV polypeptide is capable of forming a virus-like particle of CMV upon expression by self-assembly. Preferably, the modified CMV polypeptide is a recombinant modified CMV polypeptide and is capable of forming a virus-like particle of CMV upon expression by self-assembly in E. coli.

N-terminal region of the CMV polypeptide: The term "N-terminal region of the CMV polypeptide" as used herein, refers either to the N-terminus of said CMV polypeptide, and in particular to the N-terminus of a coat protein of CMV, or to the region of the N-terminus of said CMV polypeptide or said coat protein of CMV but starting with the second amino acid of the N-terminus of said CMV polypeptide or said coat protein of CMV if said CMV polypeptide or said coat protein comprises a N-terminal methionine residue. Preferably, in case said CMV polypeptide or said coat protein comprises a N-terminal methionine residue, from a practical point of view, the start-codon encoding methionine will usually be deleted and added to the N-terminus of the Th cell epitope. Further preferably, one, two or three additional amino acids, preferably one amino acid, may be optionally inserted between the stating methionine and the Th cell epitope for cloning purposes. The term "N-terminal region of the mutated amino acid sequence of a CMV polypeptide or a CMV coat protein" as used herein, refers either to the N-terminus of said mutated amino acid sequence of said CMV polypeptide or said coat protein of CMV, or to the region of the N-terminus of said mutated amino acid sequence of said CMV polypeptide or said coat protein of CMV but starting with the second amino acid of the N-terminus of said mutated amino acid sequence of said CMV polypeptide or said coat protein of CMV if said mutated amino acid sequence comprises a N-terminal methionine residue. Preferably, in case said CMV polypeptide or said coat protein comprises a N-terminal methionine residue, from a practical point of view, the start-codon encoding methionine will usually be deleted and added to the N-terminus of the Th cell epitope. Further preferably, one, two or three additional amino acids, preferably one amino acid, may be optionally inserted between the stating methionine and the Th cell epitope for cloning purposes.

Recombinant polypeptide: In the context of the invention the term "recombinant polypeptide" refers to a polypeptide which is obtained by a process which comprises at least one step of recombinant DNA technology. Typically and preferably, a recombinant polypeptide is produced in a prokaryotic expression system. It is apparent for the artisan that recombinantly produced polypeptides which are expressed in a prokaryotic expression system such as *E. coli* may comprise an N-terminal methionine residue. The N-terminal methionine residue is typically cleaved off the recombinant polypeptide in the expression host during the maturation of the recombinant polypeptide. However, the cleavage of the N-terminal methionine may be incomplete. Thus, a preparation of a recombinant polypeptide may comprise a mixture of otherwise identical polypeptides with and without an N-terminal methionine residue. Typically and preferably, a preparation of a recombinant polypeptide comprises less than 10%, more preferably less than 5%, and still more preferably less than 1% recombinant polypeptide with an N-terminal methionine residue.

Recombinant CMV polypeptide: The term "recombinant CMV polypeptide" refers to a CMV polypeptide as defined above which is obtained by a process which comprises at least one step of recombinant DNA technology. Typically and preferably a preparation of a recombinant CMV polypeptide comprises less than 10%, more preferably less than 5%, and still more preferably less than 1% recombinant CMV polypeptide with an N-terminal methionine residue. Consequently, a recombinant virus-like particle of the invention may comprise otherwise identical recombinant polypeptides with and without an N-terminal methionine residue.

Recombinant modified CMV polypeptide: The term "recombinant modified CMV polypeptide" refers to a modified CMV polypeptide as defined above which is obtained by a process which comprises at least one step of recombinant DNA technology. Typically and preferably a preparation of a recombinant modified CMV polypeptide comprises less than 10%, more preferably less than 5%, and still more preferably less than 1% recombinant modified CMV polypeptide with an N-terminal methionine residue. Consequently, a recombinant virus-like particle of the invention may comprise otherwise identical recombinant polypeptides with and without an N-terminal methionine residue.

Recombinant virus-like particle: In the context of the invention the term "recombinant virus-like particle" refers to a virus-like particle (VLP) which is obtained by a process which comprises at least one step of recombinant DNA technology. Typically and preferably a recombinant VLP is obtained by expression of a recombinant viral coat protein in host, preferably in a bacterial cell. Typically and preferably, a recombinant virus-like particle comprises at least one recombinant polypeptide, preferably a recombinant CMV polypeptide or recombinant modified CMV polypeptide. Most preferably, a recombinant virus-like particle is composed of or consists of recombinant CMV polypeptides or recombinant modified CMV polypeptides. As a consequence, if in the context of the present invention the definition of inventive recombinant VLPs are effected with reference to specific amino acid sequences comprising a N-terminal methionine residue the scope of these inventive recombinant VLPs encompass the VLPs formed by said specific amino acid sequences without said N-terminal methionine residue but as well, even though typically in a minor amount as indicated herein, the VLPs formed by said specific amino acid sequences with said N-terminal methionine. Furthermore, it is within the scope of the present invention that if the definition of inventive recombinant VLPs are effected with reference to specific amino acid sequences comprising a N-terminal methionine residue VLPs are encompassed comprising both amino acid sequences comprising still said N-terminal methionine residue and amino acid sequences lacking the N-terminal methionine residue.

Mutated amino acid sequence: The term "mutated amino acid sequence" refers to an amino acid sequence which is obtained by introducing a defined set of mutations into an amino acid sequence to be mutated. In the context of the invention, said amino acid sequence to be mutated typically and preferably is an amino acid sequence of a coat protein of CMV. Thus, a mutated amino acid sequence differs from an amino acid sequence of a coat protein of CMV in at least one amino acid residue, wherein said mutated amino acid sequence and said amino acid sequence to be mutated show a sequence identity of at least 90%. Typically and preferably said mutated amino acid sequence and said amino acid sequence to be mutated show a sequence identity of at least 91%, 92%, 93% 94%, 95%, 96%, 97%, 98%, or 99%. Preferably, said mutated amino acid sequence and said sequence to be mutated differ in at most 11, 10, 9, 8, 7, 6, 4, 3, 2, or 1 amino acid residues, wherein further preferably said difference is selected from insertion, deletion and amino acid exchange. Preferably, the mutated amino acid sequence differs from an amino acid sequence of a coat protein of CMV in least one amino acid, wherein preferably said difference is an amino acid exchange.

Position corresponding to residues . . . : The position on an amino acid sequence, which is corresponding to given residues of another amino acid sequence can be identified by sequence alignment, typically and preferably by using the BLASTP algorithm, most preferably using the standard settings. Typical and preferred standard settings are: expect threshold: 10; word size: 3; max matches in a query range: 0; matrix: BLOSUM62; gap costs: existence 11, extension 1; compositional adjustments: conditional compositional score matrix adjustment.

Sequence identity: The sequence identity of two given amino acid sequences is determined based on an alignment of both sequences. Algorithms for the determination of sequence identity are available to the artisan. Preferably, the sequence identity of two amino acid sequences is determined using publicly available computer homology programs such as the "BLAST" program (blast.ncbi.nlm.nih.gov/Blast.cgi) or the "CLUSTALW" (genome.jp/tools/clustalw/), and hereby preferably by the "BLAST" program provided on the NCBI homepage at blast.ncbi.nlm.nih.gov/Blast.cgi, using the default settings provided therein. Typical and preferred standard settings are: expect threshold: 10; word size: 3; max matches in a query range: 0; matrix: BLOSUM62; gap costs: existence 11, extension 1; compositional adjustments: conditional compositional score matrix adjustment.

Amino acid exchange: The term amino acid exchange refers to the exchange of a given amino acid residue in an amino acid sequence by any other amino acid residue having a different chemical structure, preferably by another proteinogenic amino acid residue. Thus, in contrast to insertion or deletion of an amino acid, the amino acid exchange does not change the total number of amino acids of said amino acid sequence. Very preferred in the context of the invention is the exchange of an amino acid residue of said amino acid sequence to be mutated by a lysine residue or by a cysteine residue.

Epitope: The term epitope refers to continuous or discontinuous portions of an antigen, preferably a polypeptide, wherein said portions can be specifically bound by an antibody or by a T-cell receptor within the context of an MHC molecule. With respect to antibodies, specific binding excludes non-specific binding but does not necessarily exclude cross-reactivity. An epitope typically comprise 5-20 amino acids in a spatial conformation which is unique to the antigenic site.

T helper (Th) cell epitope: The term "T helper (Th) cell epitope" as used herein refers to an epitope that is capable of recognition by a helper Th cell. In another preferred embodiment, said T helper cell epitope is a universal T helper cell epitope.

Universal Th cell epitope: The term "universal Th cell epitope" as used herein refers to a Th cell epitope that is capable of binding to at least one, preferably more than one MHC class II molecules. The simplest way to determine whether a peptide sequence is a universal Th cell epitope is to measure the ability of the peptide to bind to individual MHC class II molecules. This may be measured by the ability of the peptide to compete with the binding of a known Th cell epitope peptide to the MHC class II molecule. A representative selection of HLA-DR molecules are described in e.g. Alexander J, et al., Immunity (1994) 1:751-761. Affinities of Th cell epitopes for MHC class II molecules should be at least $10^{-5}$M. An alternative, more tedious but also more relevant way to determine the "universality" of a Th cell epitope is the demonstration that a larger fraction of people (>30%) generate a measurable T cell response upon immunization and boosting one months later with a protein containing the Th cell epitope formulated in IFA. A representative collection of MHC class II molecules present in different individuals is given in Panina-Bordignon P, et al., Eur J Immunol (1989) 19:2237-2242. As a consequence, the term "universal Th cell epitope" as used herein preferably refers to a Th cell epitope that generates a measurable T cell response upon immunization and boosting (one months later with a protein containing the Th cell epitope formulated in IFA) in more than 30% of a selected group of individuals as described in Panina-Bordignon P, et al., Eur J Immunol (1989) 19:2237-2242. Moreover, and again further preferred, the term "universal Th cell epitope" as used herein preferably refers to a Th cell epitope that is capable of binding to at least one, preferably to at least two, and even more preferably to at least three DR alleles selected from of DR1, DR2w2b, DR3, DR4w4, DR4w14, DR5, DR7, DR52a, DRw53, DR2w2a; and preferably selected from DR1, DR2w2b, DR4w4, DR4w14, DR5, DR7, DRw53, DR2w2a, with an affinity at least 500 nM (as described in Alexander J, et al., Immunity (1994) 1:751-761 and references cited herein); a preferred binding assay to evaluate said affinities is the one described by Sette A, et al., J Immunol (1989) 142:35-40. In an even again more preferable manner, the term "universal Th cell epitope" as used herein refers to a Th cell epitope that is capable of binding to at least one, preferably to at least two, and even more preferably to at least three DR alleles selected from DR1, DR2w2b, DR4w4, DR4w14, DR5, DR7, DRw53, DR2w2a, with an affinity at least 500 nM (as described in Alexander J, et al., Immunity (1994) 1:751-761 and references cited herein); a preferred binding assay to evaluate said affinities is the one described by Sette A, et al., J Immunol (1989) 142:35-40.

Universal Th cell epitopes are described, and known to the skilled person in the art, such as by Alexander J, et al., Immunity (1994) 1:751-761, Panina-Bordignon P, et al., Eur J Immunol (1989) 19:2237-2242, Calvo-Calle J M, et al., J Immunol (1997) 159:1362-1373, and Valmori D, et al., J Immunol (1992) 149:717-721.

Adjuvant: The term "adjuvant" as used herein refers to non-specific stimulators of the immune response or substances that allow generation of a depot in the host which when combined with the vaccine and pharmaceutical composition, respectively, of the present invention may provide for an even more enhanced immune response. Preferred adjuvants are complete and incomplete Freund's adjuvant, aluminum containing adjuvant, preferably aluminum hydroxide, and modified muramyldipeptide. Further preferred adjuvants are mineral gels such as aluminum hydroxide, surface active substances such as lyso lecithin, pluronic polyols, polyanions, peptides, oil emulsions, keyhole limpet hemocyanins, dinitrophenol, and human adjuvants such as BCG (bacille Calmette Guerin) and *Corynebacterium parvum*. Such adjuvants are also well known in the art. Further adjuvants that can be administered with the compositions of the invention include, but are not limited to, Monophosphoryl lipid immunomodulator, AdjuVax 100a, QS-21, QS-18, CRL1005, Aluminum salts (Alum), MF-59, OM-174, OM-197, OM-294, and Virosomal adjuvant technology. The adjuvants may also comprise mixtures of these substances. Virus-like particles have been generally described as an adjuvant. However, the term "adjuvant", as used within the context of this application, refers to an adjuvant not being the inventive virus-like particle. Rather "adjuvant" relates to an additional, distinct component of the inventive compositions, vaccines or pharmaceutical compositions.

The term "allergic condition" is defined herein as a disorder or disease caused by an interaction between the immune system and a substance foreign to the body. This foreign substance is termed "an allergen". Common allergens include aeroallergens, such as pollens, dust, molds, dust mite proteins, injected saliva from insect bites, etc. Examples of allergic conditions include, but are not limited to, the following: allergic dermatitis, summer eczema, recurrent urticaria, pruritus, heaves, inflammatory airway disease, recurrent airway obstruction, airway hyper-responsiveness, chronic obstructive pulmonary disease, and inflammatory processes resulting from autoimmunity, such as Irritable bowel syndrome (IBS).

The term "pruritic condition" is defined herein as a disease or disorder characterized by an intense itching sensation that produces the urge to rub or scratch the skin to obtain relief Examples of pruritic conditions include, but are not limited to the following: atopic dermatitis, eczema, psoriasis, scleroderma, pruritus, allergic dermatitis, bacterial folliculitis, dermatophytosis, and recurrent urticaria.

Effective amount: As used herein, the term "effective amount" refers to an amount of an active ingredient, typically and preferably a composition in accordance with the present invention, sufficient to effect beneficial or desired results when administered to an equine mammal, preferably to a horse. An effective amount can be administered in one or more administrations, applications or dosages. An effective amount of the composition, or alternatively the pharmaceutical composition, would be the amount that achieves this selected result, and such an amount could be determined as a matter of routine by a person skilled in the art. Preferably, the term "effective amount", as used herein, refers to an amount that produces an objectively measured change in one or more parameter associated with the prevention or treatment of a condition or disorder selected from a pruritic condition or an allergic condition, of an equine mammal, preferably of a horse. Again further preferably, said one or more parameter associated with the prevention or treatment of a condition or disorder selected from a pruritic condition or an allergic condition is the level or severity grade of skin lesions or the level of pruritus. Again further preferably, said reduction of said level or severity grade of skin lesions is determined by a symptom lesion scoring test and said reduction of said level of pruritus is determined by a pruritus scoring test. The effective amount can vary depending upon the particular equine mammal, preferably the horse, and condition being treated, the weight and age of the equine mammal, preferably the horse, the severity of the disease condition, the particular composition chosen, the dosing regimen to be followed, timing of administration, the manner of administration and the like, all of which can readily be determined by one of ordinary skill in the art without necessitating undue experimentation.

Combinatory treatment: As used herein, the term "combinatory treatment" or "combinatory vaccination" as interchangeably used herein, refers to a treatment in accordance with the present invention in which at least two, typically and preferably exactly two, different inventive compositions are used and wherein said different inventive compositions are applied as separate entities and not as one combined, typically and preferably, pharmaceutical, composition comprising said at least two different inventive compositions. The use of said at least two, typically and preferably exactly two, different inventive compositions as separate entities does not exclude, however, the application, typically and preferably administration, of said at least two, typically and preferably exactly two, different inventive compositions at the same time and/or at the same place, typically and preferably at the same administration and injection site.

Combination treatment: As used herein, the term "combination treatment" or "combination vaccination" as interchangeably used herein, refers to a treatment in accordance with the present invention in which at least two, typically and preferably exactly two, different inventive compositions are used and wherein said different inventive compositions are applied as one entity, typically and preferably, comprised and combined in and as one pharmaceutical, composition comprising said at least two different inventive compositions in accordance with the present invention.

Treatment: As used herein, the terms "treatment", "treat", "treated" or "treating" refer to prophylaxis and/or therapy. In one embodiment, the terms "treatment", "treat", "treated" or "treating" refer to a therapeutic treatment. In another embodiment, the terms "treatment", "treat", "treated" or "treating" refer to a prophylactic treatment. Typically and preferably, equine mammals, preferably horses, in need of treatment include those already with the disorder as well as those in which the disorder is to be prevented. Thus, preferably, the terms "treatment", "treat", "treated" or "treating" of a disease, condition or disorder in accordance with the present invention, includes preventing or protecting against the disease, condition or disorder (that is, causing the symptoms not to develop); inhibiting the disease, condition or disorder (i.e., arresting or suppressing the development of symptoms; and/or relieving the disease, condition or disorder (i.e., causing the regression of symptoms). As will be appreciated, it is not always possible to distinguish between "preventing" and "suppressing" a disease, condition or disorder since the ultimate inductive event or events may be unknown or latent. Accordingly, the term "prophylaxis" will be understood to constitute a type of "treatment" that encompasses both "preventing" and "suppressing." The term "treatment" thus includes "prophylaxis".

The term "prophylaxis" as used herein refers to means of preventing or delaying the onset of disease or condition and/or symptoms attributed to the disease or condition.

Attachment Site, First: As used herein, the phrase "first attachment site" refers to an element which is naturally occurring with the virus-like particle or which is artificially added to the virus-like particle, and to which the second attachment site may be linked. The first attachment site preferably is a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the first attachment site is the amino group of an amino acid residue, preferably of a lysine residue. The first attachment site is typically located on the surface, and preferably on the outer surface of the VLP. Multiple first attachment sites are present on the surface, preferably on the outer surface of the VLP, typically in a repetitive configuration. In a preferred embodiment the first attachment site is associated with the VLP, through at least one covalent bond, preferably through at least one peptide bond. In a further preferred embodiment the first attachment site is naturally occurring with the VLP. Alternatively, in a preferred embodiment the first attachment site is artificially added to the VLP. In a very preferred embodiment said first attachment site is the amino group of a lysine residue of the amino acid sequence of said VLP polypeptide.

Attachment Site, Second: As used herein, the phrase "second attachment site" refers to an element which is naturally occurring with or which is artificially added to the antigen and to which the first attachment site may be linked. The second attachment site of the antigen preferably is a protein, a polypeptide, a peptide, an amino acid, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the second attachment site is a sulfhydryl group, preferably the sulfhydryl group of the amino acid cysteine most preferably the sulfhydryl group of a cysteine residue. The term "antigen with at least one second attachment site" refers, therefore, to a construct comprising the antigen and at least one second attachment site. However, in particular for a second attachment site, which is not naturally occurring within the antigen, such a construct typically and preferably further comprises a "linker". In another preferred embodiment the second attachment site is associated with the antigen through at least one covalent bond, preferably through at least one peptide bond. In a further embodiment, the second attachment site is naturally occurring within the antigen. In another further preferred embodiment, the second attachment site is artificially added to the antigen through a linker, wherein said linker comprises or alternatively consists of a cysteine. Preferably, the linker is fused to the antigen by a peptide bond.

Linked: The terms "linked" or "linkage" as used herein, refer to all possible ways, preferably chemical interactions, by which the at least one first attachment site and the at least one second attachment site are joined together. Chemical interactions include covalent and non-covalent interactions. Typical examples for non-covalent interactions are ionic interactions, hydrophobic interactions or hydrogen bonds, whereas covalent interactions are based, by way of example, on covalent bonds such as ester, ether, phosphoester, carbon-phosphorus bonds, carbon-sulfur bonds such as thioether, or imide bonds. In certain preferred embodiments the first attachment site and the second attachment site are linked through at least one covalent bond, preferably through at least one non-peptide bond, and even more preferably through exclusively non-peptide bond(s). The term "linked" as used herein, however, shall not only refer to a direct linkage of the at least one first attachment site and the at least one second attachment site but also, alternatively and preferably, an indirect linkage of the at least one first attachment site and the at least one second attachment site through intermediate molecule(s), and hereby typically and preferably by using at least one, preferably one, heterobifunctional cross-linker. In other preferred embodiments the first attachment site and the second attachment site are linked through at least one covalent bond, preferably through at least one peptide bond, and even more preferably through exclusively peptide bond(s).

Linker: A "linker", as used herein, either associates the second attachment site with the antigen or already comprises, essentially consists of, or consists of the second attachment site. Preferably, a "linker", as used herein, already comprises the second attachment site, typically and preferably—but not necessarily—as one amino acid residue, preferably as a cysteine residue. A preferred linkers are an amino acid linkers, i.e. linkers containing at least one amino acid residue. The term amino acid linker does not imply that such a linker consists exclusively of amino acid residues. However, a linker consisting exclusively of amino acid residues is a preferred embodiment of the invention. The amino acid residues of the linker are, preferably, composed of naturally occurring amino acids or unnatural amino acids known in the art, all-L or all-D or mixtures thereof. Further preferred embodiments of a linker in accordance with this invention are molecules comprising a sulfhydryl group or a cysteine residue and such molecules are, therefore, also encompassed within this invention. Association of the linker with the antigen is preferably by way of at least one covalent bond, more preferably by way of at least one peptide bond.

Equine mammal: An "equine mammal", as used herein, is a mammal included in the family Equidae including horses, ponys, asses (donkeys), and zebras. Preferably, the term "equine mammal", as used herein, refers to a horse, a pony, an ass (a donkey), and a zebra. Again more preferably, the term "equine mammal", as used herein, refers to a horse.

Several aspects of the present invention are disclosed herein; the embodiments and preferred embodiments, respectively, mentioned further herein are applicable for each and any aspect of the present invention disclosed herein, even though not explicitly mentioned.

We have now surprisingly found in skin biopsies from horses of dermatitis affected skin lesions that equine IL-31 mRNA was expressed in skin lesions from sites with pruritus-accompanied dermatitis, whereas it was completely absent in healthy horse skin samples. Thus, the compositions of the present invention which induce strong auto-antibody titers are effective for the prevention and treatment of a condition or disorder selected from a pruritic condition or an allergic condition, of an equine mammal, preferably of a horse, and in particular, are effective for the prevention and treatment of pruritus and pruritus-associated dermatitis. The effectiveness of the inventive compositions are independent of a possible allergic trigger be it allergens from trees, grass, pollens, molds, fungi, dust mites, dusts, danders, feed (provender) mites, insects or components in the food.

Thus, vaccination of horses affected by pruritus or pruritus-associated dermatitis caused by multiple allergens with inventive compositions comprising eIL-31 antigens linked to CMV-VLPs led not only to significant decrease in mean skin lesion scores but, in particular, led to a very strong decrease in mean pruritus scores as compared to said scores determined in the season before treatment with the inventive compositions. The same surprising results have been found when combination vaccines in accordance with the present invention, namely compositions comprising eIL-31 antigens linked to CMV-VLPs and compositions comprising eIL-5 antigens linked to CMV-VLPs were used to treat horses affected by pruritus or pruritus-associated dermatitis caused by multiple allergens.

Thus, in a first aspect, the present invention provides for a composition comprising: (a) a core particle with at least one first attachment site; and (b) at least one antigen with at least one second attachment site, wherein said at least one antigen is an equine Interleukin-31 antigen (eIL-31 antigen), wherein said eIL-31 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1; wherein (a) and (b) are linked through said at least one first and said at least one second attachment site via at least one non-peptide covalent bond; for use in a method of prevention or treatment of a condition or disorder selected from a pruritic condition or an allergic condition, of an equine mammal, preferably of a horse, wherein preferably an effective amount of said composition is administered to said equine mammal, preferably to said horse. In a preferred embodiment, said condition or disorder is pruritus of an equine mammal, preferably of a horse. In a further preferred embodiment, said pruritus is pruritus associated with allergic dermatitis or pruritus associated with atopic dermatitis. In a further preferred embodiment, said pruritus is pruritus associated with allergic dermatitis. In a further preferred embodiment, said pruritus is pruritus associated with atopic dermatitis. In a further preferred embodiment, said condition or disorder is not the prevention or treatment of insect bite hypersensitivity (IBH) of an equine mammal, preferably of a horse. In a further preferred embodiment, said condition or disorder is the prevention or treatment of insect bite hypersensitivity (IBH) of an equine mammal, preferably of a horse.

In a further aspect, the present invention provides for a composition comprising a first composition and a second composition, wherein said first composition comprises (a) a first core particle with at least one first attachment site; and (b) at least one first antigen with at least one second attachment site, wherein said at least one first antigen is an equine Interleukin-31 antigen (eIL-31 antigen), wherein said eIL-31 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1; and wherein (a) and (b) are linked through said at least one first and said at least one second attachment site via at least one non-peptide covalent bond; and wherein said second composition comprises (c) a second core particle with at least one first attachment site; and (d) at least one second antigen with at least one second attachment site, wherein said at least one second antigen is an equine Interleukin-5 antigen (eIL-5 antigen), wherein said eIL-5 antigen comprises, or preferably is, a protein with the amino sequence selected from SEQ ID NO:6 or a protein with an amino acid sequence of at least 90%, preferably of at least 92%, further preferably of at least 95%, and again further preferably of at least 98% amino acid sequence identity with SEQ ID NO:6, and wherein (c) and (d) are linked through said at least one first and said at least one second attachment site via at least one non-peptide covalent bond, and wherein optionally said composition further comprises an adjuvant. In a further aspect, the present invention provides for said inventive composition for use as a medicament.

The present invention, thus, provides for inventive compositions for use in all pruritic conditions or all allergic conditions independent of the allergic trigger. Moreover, the compositions are, thus, used for the methods in accordance with the present invention either alone or as add-on combinatory or combination treatment.

In a preferred embodiment, said eIL-31 antigen comprises, or preferably is, a protein with the amino sequence selected from SEQ ID NO:1, SEQ ID NO:2, SEQ ID NO:3, SEQ ID NO:4, SEQ ID NO:5. In a further preferred embodiment, said eIL-31 antigen comprises, or preferably is, a protein with the amino sequence selected from SEQ ID NO:1 and SEQ ID NO:2. In a further preferred embodiment, said eIL-31 antigen comprises, or preferably is, a protein with the amino sequence of SEQ ID NO:1. In a further preferred embodiment, said eIL-31 antigen comprises, or preferably is, a protein with the amino sequence of SEQ ID NO:2. In a further preferred embodiment, said eIL-31 antigen comprises, or preferably is, a protein with the amino sequence of SEQ ID NO:3. In a further preferred embodiment, said eIL-31 antigen comprises, or preferably is, a protein with the amino sequence of SEQ ID NO:4. In a further preferred embodiment, said eIL-31 antigen comprises, or preferably is, a protein with the amino sequence of SEQ ID NO:5.

In another preferred embodiment, said condition or disorder is the prevention or treatment of insect bite hypersensitivity (IBH) of an equine mammal, preferably of a horse.

In a preferred embodiment, said composition further comprises (c) a second core particle with at least one first attachment site; and (d) at least one second antigen with at least one second attachment site, wherein said at least one second antigen is an equine Interleukin-5 antigen (eIL-5 antigen), wherein said eIL-5 antigen comprises, or preferably is, a protein with at least 90%, preferably of at least 92%, further preferably of at least 95%, and again further preferably of at least 98% amino acid sequence identity with SEQ ID NO:6; wherein (c) and (d) are linked through said at least one first and said at least one second attachment site via at least one non-peptide covalent bond.

In another preferred embodiment, said eIL-5 antigen comprises, or preferably is, a protein with the amino sequence selected from SEQ ID NO:6, SEQ ID NO:7, SEQ ID NO:8, SEQ ID NO:9 and SEQ ID NO:10. In a further preferred embodiment, said eIL-5 antigen comprises, or preferably is, a protein with the amino sequence selected from SEQ ID NO:6, and SEQ ID NO:7. In a further preferred embodiment, said eIL-5 antigen comprises, or preferably is, a protein with the amino sequence selected from SEQ ID NO:8, SEQ ID NO:9 and SEQ ID NO:10. In a further preferred embodiment, said eIL-5 antigen comprises, or preferably is, a protein with the amino sequence of SEQ ID NO:6, In a further preferred embodiment, said eIL-5 antigen comprises, or preferably is, a protein with the amino sequence of SEQ ID NO:7. In a further preferred embodiment, said eIL-5 antigen comprises, or preferably is, a protein with the amino sequence of SEQ ID NO: 8. In a further preferred embodiment, said eIL-5 antigen comprises, or preferably is, a protein with the amino sequence of SEQ ID NO:9. In a further preferred embodiment, said eIL-5 antigen comprises, or preferably is, a protein with the amino sequence of SEQ ID NO:10.

In a further preferred embodiment, said core particle or said first core particle, respectively, which is linked to said at least one eIL-31 antigen in accordance with the present invention is the same as, if present in the inventive composition, said second core particle which is linked to said at least one eIL-5 antigen.

In a further preferred embodiment, said core particle or said first core particle, respectively, which is linked to said at least one eIL-31 antigen in accordance with the present invention is different from, if present in the inventive composition, said second core particle which is linked to said at least one eIL-5 antigen.

In the following, if embodiments of said "core particle" are defined and solely referred to as embodiments of said "core particle" it should refer either to said core particle or said first core particle or said second core particle. Typically and preferably it should refer to said core particle or said first core particle, respectively.

In a further preferred embodiment, said core particle is a virus-like particle (VLP), preferably a recombinant VLP. In again a further preferred embodiment, said VLP is derived from a plant virus or a bacteriophage, and wherein preferably said bacteriophage is a RNA bacteriophage.

Thus, in a further preferred embodiment, said core particle is a virus-like particle (VLP), and wherein said VLP is derived from a RNA bacteriophage.

Further preferred is a recombinant VLP of an RNA bacteriophage as core particle of the present invention. In a further preferred embodiment, said VLP comprises, consists essentially of, or alternatively consists of, recombinant coat proteins of an RNA bacteriophage, and wherein preferably said VLP comprises, consists essentially of, or alternatively consists of, recombinant coat proteins of RNA bacteriophage Qβ or of RNA bacteriophage AP205, and wherein further preferably said VLP comprises, consists essentially of, or alternatively consists of, recombinant coat proteins of RNA bacteriophage Qβ.

In a further preferred embodiment, said VLP comprises, consists essentially of, or alternatively consists of, recombinant coat proteins comprising or preferably consisting of an amino acid sequence selected from (a) SEQ ID NO:24; (b) a mixture of SEQ ID NO:24 and SEQ ID NO:25; or (c) SEQ ID NO:26. In a very further preferred embodiment, said VLP is a VLP of RNA bacteriophage Qβ. In a further preferred embodiment, said VLP comprises, consists essentially of, or alternatively consists of, recombinant coat proteins of RNA bacteriophage Qβ. Again in a further preferred embodiment, said VLP comprises, consists essentially of, or alternatively consists of, recombinant coat proteins comprising or preferably consisting of SEQ ID NO:24.

In another preferred embodiment, said core particle is a virus-like particle (VLP) wherein said VLP is a VLP of RNA bacteriophage Qβ, and said VLP comprises, consists essentially of, or alternatively consists of, recombinant coat proteins of RNA bacteriophage Qβ, and wherein said recombinant coat proteins comprising or preferably consisting of SEQ ID NO:24.

In one embodiment, said VLP is not a VLP of an RNA bacteriophage, preferably said VLP is not a recombinant VLP of an RNA bacteriophage. In one embodiment, said virus-like particle is not a virus-like particle of an RNA-bacteriophage Qβ.

In a further preferred embodiment, said core particle is a virus-like particle (VLP), and wherein said VLP is derived from a plant virus. In another preferred embodiment, said VLP is a recombinant VLP, and wherein preferably said recombinant VLP is derived from a plant virus. In another preferred embodiment, said VLP is a VLP of cucumber mosaic virus (CMV).

In a preferred embodiment, said VLP is a modified VLP comprising, essentially consisting of, or alternatively consisting of, at least one modified VLP polypeptide, wherein said modified VLP polypeptide comprises, or preferably consists of, (a) a VLP polypeptide, and (b) a T helper cell epitope, wherein said VLP polypeptide comprises, or preferably consists of, (i) an amino acid sequence of a coat protein of a virus, preferably an amino acid sequence of a coat protein of a plant virus; or (ii) a mutated amino acid sequence, wherein the amino acid sequence to be mutated is an amino acid sequence of said coat protein of a virus, and wherein said mutated amino acid sequence and said coat protein of a virus show a sequence identity of at least 90%, preferably of at least 95%, further preferably of at least 98% and again more preferably of at least 99%.

In a preferred embodiment, said VLP is a modified VLP of cucumber mosaic virus (CMV), wherein said modified VLP of CMV comprises, essentially consists of, or alternatively consists of, at least one modified CMV polypeptide, wherein said modified CMV polypeptide comprises, or preferably consists of, (a) a CMV polypeptide, and (b) a T helper cell epitope; and wherein said CMV polypeptide comprises, or preferably consists of, (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%.

In a preferred embodiment, said CMV polypeptide comprises, preferably consists of, an amino acid sequence of a coat protein of CMV. In another preferred embodiment, said CMV polypeptide comprises, preferably consists of a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%. Typically and preferably, said mutated amino acid sequence and said amino acid sequence to be mutated differ in least one and in at most 11, 10, 9, 8, 7, 6, 5, 4, 3, or 2 amino acid residues, and wherein preferably these differences are selected from (i) insertion, (ii) deletion, (iii) amino acid exchange, and (iv) any combination of (i) to (iii).

In another preferred embodiment, said CMV polypeptide comprises, or preferably consists of, (i) (a) an amino acid sequence of a coat protein of CMV, wherein said amino acid sequence comprises, or preferably consists of, SEQ ID NO:15 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:15; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 95%, preferably of at least 98%, and more preferably of at least 99%.

In another preferred embodiment, said CMV polypeptide comprises, or preferably consists of, (a) an amino acid sequence of a coat protein of CMV, wherein said amino acid sequence comprises, or preferably consists of, SEQ ID NO:15 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:15.

In another preferred embodiment, said CMV polypeptide comprises, or preferably consists of, (i) (a) an amino acid sequence of a coat protein of CMV, wherein said amino acid sequence comprises SEQ ID NO:27, or (b) an amino acid sequence of a coat protein of CMV comprising an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:27; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 95%, preferably of at least 98%, and more preferably of at least 99%.

In a further preferred embodiment, said CMV polypeptide comprises, or preferably consists of, (a) an amino acid sequence of a coat protein of CMV, wherein said amino acid sequence comprises SEQ ID NO:27, or (b) an amino acid sequence of a coat protein of CMV comprising an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:27.

In another preferred embodiment, said CMV polypeptide comprises, or preferably consists of, (i) (a) an amino acid sequence of a coat protein of CMV, wherein said amino acid sequence comprises, or preferably consists of, SEQ ID NO:15 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:15; and wherein said amino sequence as defined in (a) or (b) comprises SEQ ID NO:27; or wherein said amino sequence as defined in (a) or (b) comprises an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:27; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 98% preferably of at least 99%.

In another preferred embodiment, said CMV polypeptide comprises, or preferably consists of, (a) an amino acid sequence of a coat protein of CMV, wherein said amino acid sequence comprises, or preferably consists of, SEQ ID NO:15 or (b) an amino acid sequence having a sequence identity of at least 90% of SEQ ID NO:15; and wherein said amino sequence as defined in (a) or (b) in this claim comprises SEQ ID NO:27; or wherein said amino sequence as defined in (a) or (b) in this claim comprises an amino acid sequence region, wherein said amino acid sequence region has a sequence identity of at least 90% with SEQ ID NO:27.

In another preferred embodiment, said T helper cell epitope replaces a N-terminal region of said CMV polypeptide. In another preferred embodiment the number of amino acids of said N-terminal region replaced is equal to or lower than the number of amino acids of which said T helper cell epitope consists.

In a further very preferred embodiment, said T helper cell epitope replaces a N-terminal region of said CMV polypeptide, and wherein the number of amino acids of said N-terminal region replaced is equal to or lower than the number of amino acids of which said T helper cell epitope consists. Typically and preferably, said replaced N-terminal region of said CMV polypeptide consists of 5 to 15 consecutive amino acids, preferably of 9 to 14 consecutive amino acids, more preferably of 11 to 13 consecutive amino acids.

In a further very preferred embodiment, said N-terminal region of said CMV polypeptide corresponds to amino acids 2-12 of SEQ ID NO:15.

In another very preferred embodiment, said T helper cell epitope is a universal T helper cell epitope. In another preferred embodiment, said T helper cell epitope consists of at most 20 amino acids.

In a very preferred embodiment, said Th cell epitope is a PADRE sequence. In a further very referred embodiment, said Th cell epitope comprises, preferably consists of, the amino acid sequence of SEQ ID NO:19. In another very preferred embodiment, said Th cell epitope is a PADRE sequence, and wherein said Th cell epitope comprises, preferably consists of, the amino acid sequence of SEQ ID NO:19.

In another preferred embodiment, said T helper cell epitope is derived from a human vaccine. In a very preferred embodiment, said Th cell epitope is derived from tetanus toxin. In a further very referred embodiment, said Th cell epitope has, preferably consists of, the amino acid sequence of SEQ ID NO:18. In another very preferred embodiment, said Th cell epitope is derived from tetanus toxin, and wherein said Th cell epitope has, preferably consists of, the amino acid sequence of SEQ ID NO:18.

In a very preferred embodiment, said Th cell epitope is a PADRE sequence, and wherein said Th cell epitope comprises, preferably consists of, the amino acid sequence of SEQ ID NO:19; or wherein said Th cell epitope is derived from tetanus toxin, and wherein said Th cell epitope has, preferably consists of, the amino acid sequence of SEQ ID NO:18.

In a very preferred embodiment, said CMV polypeptide comprises, or preferably consists of, an amino acid sequence of a coat protein of CMV, wherein said amino acid sequence comprises, or preferably consists of, SEQ ID NO:15 or an amino acid sequence having a sequence identity of at least 95% of SEQ ID NO:15; and wherein said amino sequence comprises SEQ ID NO:27, and wherein said T helper cell epitope replaces the N-terminal region of said CMV polypeptide, and wherein said replaced N-terminal region of said CMV polypeptide consists of 11 to 13 consecutive amino acids, preferably of 11 consecutive amino acids, and wherein further preferably said N-terminal region of said CMV polypeptide corresponds to amino acids 2-12 of SEQ ID NO:15.

In another very preferred embodiment, said modified CMV polypeptide comprises, preferably consists of, an amino acid sequence of SEQ ID NO:20. In another very preferred embodiment, said modified CMV polypeptide comprises, preferably consists of, an amino acid sequence of SEQ ID NO:21.

In a very preferred embodiment, said first attachment site and said second attachment site are linked via at least one covalent non-peptide-bond. In another very preferred embodiment, said first attachment site comprises, or preferably is, an amino group, preferably an amino group of a lysine. In a further very preferred embodiment, said second attachment site comprises, or preferably is, a sulfhydryl group, preferably a sulfhydryl group of a cysteine.

In a very preferred embodiment, the at least one first attachment site is an amino group, preferably an amino group of a lysine residue and the at least one second attachment site is a sulfhydryl group, preferably a sulfhydryl group of a cysteine residue or a sufhydryl group that has been chemically attached to the at least one antigen of the invention. In a further preferred embodiment only one of said second attachment sites associates with said first attachment site through at least one non-peptide covalent bond leading to a single and uniform type of binding of said antigen to said modified virus-like particle, wherein said only one second attachment site that associates with said first attachment site is a sulfhydryl group, and wherein said antigen and said modified virus-like particle interact through said association to form an ordered and repetitive antigen array.

In one preferred embodiment of the invention, the antigen is linked to the modified VLP by way of chemical cross-linking, typically and preferably by using a heterobifunctional cross-linker. In preferred embodiments, the hetero-bifunctional cross-linker contains a functional group which can react with the preferred first attachment sites, preferably with the amino group, more preferably with the amino groups of lysine residue(s) of the modified VLP, and a further functional group which can react with the preferred second attachment site, i.e. a sulfhydryl group, preferably of cysteine(s) residue inherent of, or artificially added to the antigen, and optionally also made available for reaction by reduction. Several hetero-bifunctional cross-linkers are known to the art. These include the preferred cross-linkers SMPH (Pierce), Sulfo-MBS, Sulfo-EMCS, Sulfo-GMBS, Sulfo-SIAB, Sulfo-SMPB, Sulfo-SMCC, Sulfo-KMUS SVSB, SIA, and other cross-linkers available for example from the Pierce Chemical Company, and having one functional group reactive towards amino groups and one functional group reactive towards sulfhydryl groups. The above mentioned cross-linkers all lead to formation of an amide bond after reaction with the amino group and a thioether linkage with the sulfhydryl groups. Another class of cross-linkers suitable in the practice of the invention is characterized by the introduction of a disulfide linkage between the antigen and the modified VLP upon coupling. Preferred cross-linkers belonging to this class include, for example, SPDP and Sulfo-LC-SPDP (Pierce).

Linking of the antigen to the modified VLP by using a hetero-bifunctional cross-linker according to the preferred methods described above, allows coupling of the antigen to the modified VLP in an oriented fashion. Other methods of linking the antigen to the modified VLP include methods wherein the antigen is cross-linked to the modified VLP, using the carbodiimide EDC, and NHS. The antigen may also be first thiolated through reaction, for example with SATA, SATP or iminothiolane. The antigen, after deprotection if required, may then be coupled to the modified VLP as follows. After separation of the excess thiolation reagent, the antigen is reacted with the modified VLP, previously activated with a hetero-bifunctional cross-linker comprising a cysteine reactive moiety, and therefore displaying at least one or several functional groups reactive towards cysteine residues, to which the thiolated antigen can react, such as described above. Optionally, low amounts of a reducing agent are included in the reaction mixture. In further methods, the antigen is attached to the modified VLP, using a homo-bifunctional cross-linker such as glutaraldehyde, DSG, BM[PEO]4, BS3, (Pierce) or other known homo-bifunctional cross-linkers with functional groups reactive towards amine groups or carboxyl groups of the modified VLP.

In very preferred embodiments of the invention, the antigen is linked via a cysteine residue, having been added to either the N-terminus or the C-terminus of, or a natural cysteine residue within the antigen, to lysine residues of the modified virus-like particle. In a preferred embodiment, the composition of the invention further comprises a linker, wherein said linker associates said antigen with said second attachment site, and wherein preferably said linker comprises or alternatively consists of said second attachment site.

In a further very preferred embodiment of the invention, said core particle is a virus-like particle (VLP), preferably a recombinant VLP and said eIL-31 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1. In again a very preferred embodiment of the invention, said eIL-31 antigen comprises, or preferably is, a protein with the amino sequence selected from SEQ ID NO:1 or a protein with an amino acid sequence of at least 95%, and preferably of at least 98% amino acid sequence identity with SEQ ID NO:1. In again a very preferred embodiment of the invention, said modified CMV polypeptide comprises, preferably consists of, an amino acid sequence of SEQ ID NO:20 and said eIL-31 antigen comprises, or preferably is, protein with the amino sequence selected from SEQ ID NO:1, SEQ ID NO:2, SEQ ID NO:3, SEQ ID NO:4, SEQ ID NO:5. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:1. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:2.

In a further very preferred embodiment of the invention, said core particle is a modified VLP, preferably a recombinant modified VLP, in accordance with the present invention and said eIL-31 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1. In again a very preferred embodiment of the invention, said eIL-31 antigen comprises, or preferably is, a protein with the amino sequence selected from SEQ ID NO:1 or a protein with an amino acid sequence of at least 95%, and preferably of at least 98% amino acid sequence identity with SEQ ID NO:1. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence selected from SEQ ID NO:1, SEQ ID NO:2, SEQ ID NO:3, SEQ ID NO:4, SEQ ID NO:5. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence selected from SEQ ID NO:1 and SEQ ID NO:2. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:1. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:2. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:3. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:4. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:5.

In a further very preferred embodiment of the invention, said core particle is a VLP, preferably a recombinant VLP, wherein said VLP is a modified VLP of cucumber mosaic virus (CMV), wherein said modified VLP of CMV comprises, essentially consists of, or alternatively consists of, at least one modified CMV polypeptide, wherein said modified CMV polypeptide comprises, or preferably consists of (a) a CMV polypeptide, and (b) a T helper cell epitope; and wherein said CMV polypeptide comprises, or preferably consists of, (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%, and wherein said eIL-31 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1. In again a very preferred embodiment of the invention, said eIL-31 antigen comprises, or preferably is, a protein with the amino sequence selected from SEQ ID NO:1 or a protein with an amino acid sequence of at least 95%, and preferably of at least 98% amino acid sequence identity with SEQ ID NO:1. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence selected from SEQ ID NO:1, SEQ ID NO:2, SEQ ID NO:3, SEQ ID NO:4, SEQ ID NO:5. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence selected from SEQ ID NO:1 and SEQ ID NO:2. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:1. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:2. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:3. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:4. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:5.

In a further very preferred embodiment of the invention, said core particle is a VLP, preferably a recombinant VLP, wherein said VLP is a modified VLP of cucumber mosaic virus (CMV), wherein said modified VLP of CMV comprises, essentially consists of, or alternatively consists of, at least one modified CMV polypeptide, and wherein said modified CMV polypeptide comprises, preferably consists of, an amino acid sequence of SEQ ID NO:20 and said eIL-31 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1. In again a very preferred embodiment of the invention, said eIL-31 antigen comprises, or preferably is, a protein with the amino sequence selected from SEQ ID NO:1 or a protein with an amino acid sequence of at least 95%, and preferably of at least 98% amino acid sequence identity with SEQ ID NO:1. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence selected from SEQ ID NO:1, SEQ ID NO:2, SEQ ID NO:3, SEQ ID NO:4, SEQ ID NO:5. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence selected from SEQ ID NO:1 and SEQ ID NO:2. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:1. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:2. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:3. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:4. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:5.

In a further very preferred embodiment of the invention, said core particle is a VLP, preferably a recombinant VLP, wherein said VLP is a modified VLP of cucumber mosaic virus (CMV), wherein said modified VLP of CMV comprises, essentially consists of, or alternatively consists of, at least one modified CMV polypeptide, and wherein said modified CMV polypeptide comprises, preferably consists of, an amino acid sequence of SEQ ID NO:21 and said eIL-31 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1. In again a very preferred embodiment of the invention, said modified CMV polypeptide comprises, preferably consists of, an amino acid sequence of SEQ ID NO:21 and said eIL-31 antigen comprises, or preferably is, a protein with the amino sequence selected from SEQ ID NO:1 and SEQ ID NO:2. In again a very preferred embodiment of the invention, said modified CMV polypeptide comprises, preferably consists of, an amino acid sequence of SEQ ID NO:21 and said eIL-31 antigen comprises, or preferably is, a protein with the amino sequence of SEQ ID NO:1. In again a very preferred embodiment of the invention, said modified CMV polypeptide comprises, preferably consists of, an amino acid sequence of SEQ ID NO:21 and said eIL-31 antigen comprises, or preferably is, a protein with the amino sequence of SEQ ID NO:2. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:3. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:4. In again a very preferred embodiment of the invention, said modified CMV polypeptide comprises, preferably consists of, an amino acid sequence of SEQ ID NO:20 and said eIL-31 antigen comprises, or preferably is, a protein with the amino sequence of SEQ ID NO:5.

In a further very preferred embodiment of the invention, said second core particle is a virus-like particle (VLP), preferably a recombinant VLP and said eIL-5 antigen comprises, or preferably is, a protein with the amino sequence selected from SEQ ID NO:6 or a protein with an amino acid sequence of at least 90%, preferably of at least 92%, further preferably of at least 95%, and again further preferably of at least 98% amino acid sequence identity with SEQ ID NO:6. In again a preferred embodiment of the invention, said eIL-5 antigen comprises, or preferably is, a protein with the amino sequence selected from SEQ ID NO:6 or a protein with an amino acid sequence of at least 95%, and preferably of at least 98% amino acid sequence identity with SEQ ID NO:6. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence selected from SEQ ID NO:6, SEQ ID NO:7, SEQ ID NO:8, SEQ ID NO:9 and SEQ ID NO:10. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence selected from SEQ ID NO:7, SEQ ID NO:8, SEQ ID NO:9 and SEQ ID NO:10. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:6. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:7. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:8. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:9. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:10.

In a further very preferred embodiment of the invention, said second core particle is a modified VLP, preferably a recombinant modified VLP, in accordance with the present invention and said eIL-5 antigen comprises, or preferably is, a protein with the amino sequence selected from SEQ ID NO:6 or a protein with an amino acid sequence of at least 90%, preferably of at least 92%, further preferably of at least 95%, and again further preferably of at least 98% amino acid sequence identity with SEQ ID NO:6. In again a very preferred embodiment of the invention, said eIL-5 antigen comprises, or preferably is, a protein with the amino sequence selected from SEQ ID NO:6 or a protein with an amino acid sequence of at least 95%, and preferably of at least 98% amino acid sequence identity with SEQ ID NO:6. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence selected from SEQ ID NO:6, SEQ ID NO:7, SEQ ID NO:8, SEQ ID NO:9 and SEQ ID NO:10. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence selected from SEQ ID NO:7, SEQ ID NO:8, SEQ ID NO:9 and SEQ ID NO:10. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:6. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:7. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:8. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:9. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:10.

In a further very preferred embodiment of the invention, said second core particle is a VLP, preferably a recombinant VLP, wherein said VLP is a modified VLP of cucumber mosaic virus (CMV), wherein said modified VLP of CMV comprises, essentially consists of, or alternatively consists of, at least one modified CMV polypeptide, wherein said modified CMV polypeptide comprises, or preferably consists of (a) a CMV polypeptide, and (b) a T helper cell epitope; and wherein said CMV polypeptide comprises, or preferably consists of, (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%, and wherein said eIL-5 antigen comprises, or preferably is, a protein with the amino sequence selected from SEQ ID NO:6 or a protein with an amino acid sequence of at least 90%, preferably of at least 92%, further preferably of at least 95%, and again further preferably of at least 98% amino acid sequence identity with SEQ ID NO:6. In again a very preferred embodiment of the invention, said eIL-5 antigen comprises, or preferably is, a protein with the amino sequence selected from SEQ ID NO:6 or a protein with an amino acid sequence of at least 95%, and preferably of at least 98% amino acid sequence identity with SEQ ID NO:6. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence selected from SEQ ID NO:6, SEQ ID NO:7, SEQ ID NO:8, SEQ ID NO:9 and SEQ ID NO:10. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence selected from SEQ ID NO:7, SEQ ID NO:8, SEQ ID NO:9 and SEQ ID NO:10. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:6. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:7. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:8. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:9. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:10.

In a further very preferred embodiment of the invention, said second core particle is a VLP, preferably a recombinant VLP, wherein said VLP is a modified VLP of cucumber mosaic virus (CMV), wherein said modified VLP of CMV comprises, essentially consists of, or alternatively consists of, at least one modified CMV polypeptide, and wherein said modified CMV polypeptide comprises, preferably consists of, an amino acid sequence of SEQ ID NO:20 and said eIL-5 antigen comprises, or preferably is, a protein with the amino sequence selected from SEQ ID NO:6 or a protein with an amino acid sequence of at least 90%, preferably of at least 92%, further preferably of at least 95%, and again further preferably of at least 98% amino acid sequence identity with SEQ ID NO:6. In again a very preferred embodiment of the invention, said eIL-5 antigen comprises, or preferably is, a protein with the amino sequence selected from SEQ ID NO:6 or a protein with an amino acid sequence of at least 95%, and preferably of at least 98% amino acid sequence identity with SEQ ID NO:6. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence selected from SEQ ID NO:6, SEQ ID NO:7, SEQ ID NO:8, SEQ ID NO:9 and SEQ ID NO:10. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence selected from SEQ ID NO:7, SEQ ID NO:8, SEQ ID NO:9 and SEQ ID NO:10. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:6. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:7. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:8. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:9. In again a very preferred embodiment of the invention, said modified CMV polypeptide comprises, preferably consists of, an amino acid sequence of SEQ ID NO:20 and said eIL-5 antigen comprises, or preferably is, a protein with the amino sequence of SEQ ID NO:10.

In a preferred embodiment, said pruritic condition or said allergic condition is selected from atopic dermatitis, eczema, psoriasis, scleroderma, pruritus, allergic dermatitis, summer eczema (IBH), bacterial folliculitis, dermatophytosis, recurrent urticaria, heaves, inflammatory airway disease, recurrent airway obstruction, airway hyper-responsiveness, chronic obstruction pulmonary disease, and inflammatory processes resulting from autoimmunity.

In a further preferred embodiment, said pruritic condition is selected from atopic dermatitis, eczema, psoriasis, scleroderma, pruritus, allergic dermatitis, summer eczema (IBH), bacterial folliculitis, dermatophytosis, and recurrent urticaria; and wherein said allergic condition is selected from allergic dermatitis, summer eczema (IBH), recurrent urticaria, pruritus, heaves, inflammatory airway disease, recurrent airway obstruction, airway hyper-responsiveness, chronic obstruction pulmonary disease, and inflammatory processes resulting from autoimmunity.

In again a further preferred embodiment, said pruritic condition or said allergic condition is selected from atopic dermatitis, eczema, psoriasis, scleroderma, pruritus, allergic dermatitis, bacterial folliculitis, dermatophytosis, recurrent urticaria, heaves, inflammatory airway disease, recurrent airway obstruction, airway hyper-responsiveness, chronic obstruction pulmonary disease, and inflammatory processes resulting from autoimmunity.

In again a further preferred embodiment, said pruritic condition is selected from atopic dermatitis, eczema, psoriasis, scleroderma, pruritus, allergic dermatitis, bacterial folliculitis, dermatophytosis, and recurrent urticaria; and wherein said allergic condition is selected from allergic dermatitis, recurrent urticaria, pruritus, heaves, inflammatory airway disease, recurrent airway obstruction, airway hyper-responsiveness, chronic obstruction pulmonary disease, and inflammatory processes resulting from autoimmunity.

In again a further preferred embodiment, said pruritic condition or said allergic condition is selected from atopic dermatitis, eczema, psoriasis, scleroderma, pruritus, allergic dermatitis, summer eczema (IBH), bacterial folliculitis, dermatophytosis, and recurrent urticaria.

In again a further preferred embodiment, said pruritic condition or said allergic condition is selected from atopic dermatitis, eczema, psoriasis, scleroderma, pruritus, allergic dermatitis, summer eczema (IBH) and recurrent urticaria.

In a preferred embodiment, said pruritic condition is selected from atopic dermatitis, eczema, psoriasis, scleroderma, pruritus, allergic dermatitis, summer eczema (IBH), bacterial folliculitis, dermatophytosis, and recurrent urticaria; and wherein said allergic condition is selected from allergic dermatitis, summer eczema (IBH), recurrent urticaria and pruritus.

In a preferred embodiment, said pruritic condition is selected from atopic dermatitis, eczema, psoriasis, scleroderma, pruritus, allergic dermatitis, summer eczema (IBH) and recurrent urticaria; and wherein said allergic condition is selected from allergic dermatitis, summer eczema (IBH), recurrent urticaria and pruritus.

In a further preferred embodiment, said pruritic condition or said allergic condition is selected from atopic dermatitis, eczema, psoriasis, scleroderma, pruritus, allergic dermatitis, bacterial folliculitis, dermatophytosis, and recurrent urticaria.

In a further preferred embodiment, said pruritic condition is selected from atopic dermatitis, eczema, psoriasis, scleroderma, pruritus, allergic dermatitis, bacterial folliculitis, dermatophytosis, and recurrent urticaria; and wherein said allergic condition is selected from allergic dermatitis, recurrent urticaria and pruritus.

In a further preferred embodiment, said pruritic condition or said allergic condition is selected from atopic dermatitis, eczema, pruritus, allergic dermatitis, bacterial folliculitis, dermatophytosis, and recurrent urticaria.

In a further preferred embodiment, said pruritic condition or said allergic condition is selected from atopic dermatitis, eczema, pruritus, allergic dermatitis and recurrent urticaria.

In a further preferred embodiment, said pruritic condition is selected from atopic dermatitis, eczema, pruritus, allergic dermatitis, bacterial folliculitis, dermatophytosis, and recurrent urticaria; and wherein said allergic condition is selected from allergic dermatitis, recurrent urticaria and pruritus.

In a further preferred embodiment, said pruritic condition or said allergic condition is selected from atopic dermatitis, pruritus, allergic dermatitis, bacterial folliculitis, dermatophytosis, and recurrent urticaria.

In a further preferred embodiment, said pruritic condition or said allergic condition is selected from atopic dermatitis, pruritus, allergic dermatitis and recurrent urticaria.

In a further preferred embodiment, said pruritic condition is selected from atopic dermatitis, pruritus, allergic dermatitis, bacterial folliculitis, dermatophytosis, and recurrent urticaria; and wherein said allergic condition is selected from allergic dermatitis, recurrent urticaria and pruritus.

In a further preferred embodiment, said pruritic condition is selected from atopic dermatitis, pruritus, allergic dermatitis and recurrent urticaria; and wherein said allergic condition is selected from allergic dermatitis, recurrent urticaria and pruritus.

In a further preferred embodiment, said pruritic condition or said allergic condition is atopic dermatitis. In a further preferred embodiment, said pruritic condition or said allergic condition is pruritus. In a further preferred embodiment, said pruritic condition or said allergic condition is allergic dermatitis. In a further preferred embodiment, said pruritic condition or said allergic condition is recurrent urticaria.

In again a further preferred embodiment, said pruritic condition or said allergic condition is selected from atopic dermatitis, eczema, psoriasis, scleroderma, pruritus, allergic dermatitis, summer eczema (IBH), bacterial folliculitis, dermatophytosis, recurrent urticaria, heaves, inflammatory airway disease, recurrent airway obstruction, airway hyperresponsiveness, chronic obstruction pulmonary disease, and inflammatory processes resulting from autoimmunity, and wherein preferably said pruritic condition or said allergic condition is selected from atopic dermatitis, eczema, pruritus, allergic dermatitis, bacterial folliculitis, dermatophytosis, and recurrent urticaria.

In again a further preferred embodiment, said administration of said composition reduces at least one parameter or symptom associated with said pruritic condition or said allergic condition as compared to said at least one parameter or symptom associated with said pruritic condition or said allergic condition before said administration, and wherein preferably said at least one parameter or symptom associated with said pruritic condition or said allergic condition is the level or severity grade of skin lesions or the level of pruritus, and wherein further preferably said reduction of said level or severity grade of skin lesions is determined by a symptom lesion scoring test and said reduction of said level of pruritus is determined by a pruritus scoring test, wherein further preferably said reduction of said level of pruritus is determined by the reduction of scratching at least one location of the body of said equine mammal, preferably of said horse, and wherein typically and preferably said symptom lesion scoring test and said pruritus scoring test is effected as described in Example 7 and Example 8.

In a further preferred embodiment, said administration of said composition reduces at least one parameter or symptom associated with said pruritic condition or said allergic condition as compared to said at least one parameter or symptom associated with said pruritic condition or said allergic condition before said administration, wherein said at least one parameter or symptom associated with said pruritic condition or said allergic condition is the level or severity grade of skin lesions and the level of pruritus, and wherein preferably said reduction of said level or severity grade of skin lesions is determined by a symptom lesion scoring test and said reduction of said level of pruritus is determined by a pruritus scoring test, wherein further preferably said reduction of said level of pruritus is determined by the reduction of scratching at least one location of the body of said equine mammal, preferably of said horse, and wherein typically and preferably said symptom lesion scoring test and said pruritus scoring test is effected as described in Example 7 and Example 8.

EXAMPLES

Preferred core particle used in the present invention are virus-like particles (VLPs), in particular recombinant VLPs. In one preferred embodiment, the VLP is VLP of RNA bacteriophage Qβ, wherein VLP of RNA bacteriophage Qβ comprises, preferably consists of, recombinant coat proteins comprising, preferably consisting of, SEQ ID NO:24. Such preferred virus-like particles of RNA bacteriophages, in particular of RNA bacteriophage Qβ, are disclosed in WO 02/056905, the disclosure of which is herewith incorporated by reference in its entirety. In particular Example 18 of WO 02/056905 contains a detailed description of the preparation of VLP particles of RNA bacteriophage Qβ. For the present specific examples, VLPs of RNA bacteriophage Qβ consisting of recombinant coat proteins of SEQ ID NO:24 have been used. In another preferred embodiment, the VLP is a VLP of cucumber mosaic virus (CMV), in particular, a modified VLP of CMV, wherein T helper cell epitopes replace N-terminal regions of the CMV polypeptide. In a very preferred embodiment, the VLP is CMVtt830 comprising modified CMV polypeptides of SEQ ID NO:20 or CMV-Npadr comprising modified CMV polypeptides of SEQ ID NO:21, preferably CMVtt830 comprising modified CMV polypeptides of SEQ ID NO:20, as described herein and as disclosed in WO 2016/062720. In particular Examples 1 to 6 of WO 2016/062720 contain a detailed description of the preparation of VLP particles of modified CMV polypeptides of SEQ ID NO:20 and SEQ ID NO:21.

Example 1

Sampling of Skin Punch Biopsies from Horses of Dermatitis Affected Skin Lesions and Healthy Skin, RNA Isolation and eIL-31 Specific PCR A. Sampling of Skin Punch Biopsies from Horses of Dermatitis Affected Skin Lesions and Healthy Skin Two and six mm punch biopsies from lesions and healthy skin were and are taken from horses affected by pruritic and allergic dermatitis conditions.

B. RNA Isolation and cDNA Transcription of Skin Biopsies

Skin biopsies were stored in RNAlater® solution (Qiagen) at 4° C. and total RNA was isolated using RNAqueous®-Micro Kit (Invitrogen) including DNase I treatment and inactivation. RNA was transcribed into cDNA using Reverse Transcription System (Promega) and eIL-31 mRNA level and housekeeping βactin gene were amplified by PCR and quantified by qPCR.

C. Equine IL-31 & βActin PCR and qPCR

PCR:

Amplification of eIL-31 eβactin in skin biopsies using the gene-specific primers for eIL-31 (forward primer: AACAAAGAGAAGGGAGTGC—SEQ ID NO:11; reverse primer: GCTGAGCTGTTGATGTTGC—SEQ ID NO:12) and eβactin (forward primer: CCAGCACGATGAAGAT-CAAG—SEQ ID NO:13; reverse primer: GTGGACAAT-GAGGCCAGAAT—SEQ ID NO:14). The PCR was done using Q5 Hot Start Polymerase (NEB) with cycles 30" 98° C., 35×[10" 98° C., 20" 60° C., 30" 72° C.], 2' 72° C.

qPCR:

Amplification of eIL-31 eβactin in skin biopsies using the gene-specific primers for eIL-31 (forward primer: AACAAAGAGAAGGGAGTGC—SEQ ID NO:11; reverse primer: GCTGAGCTGTTGATGTTGC—SEQ ID NO:12) and eβactin (forward primer: CCAGCACGATGAAGAT-CAAG—SEQ ID NO:13; reverse primer: GTGGACAAT-GAGGCCAGAAT—SEQ ID NO:14). The PCR was done using FastStart Universal SYBR Green Master (Roche).

Figure 1A:
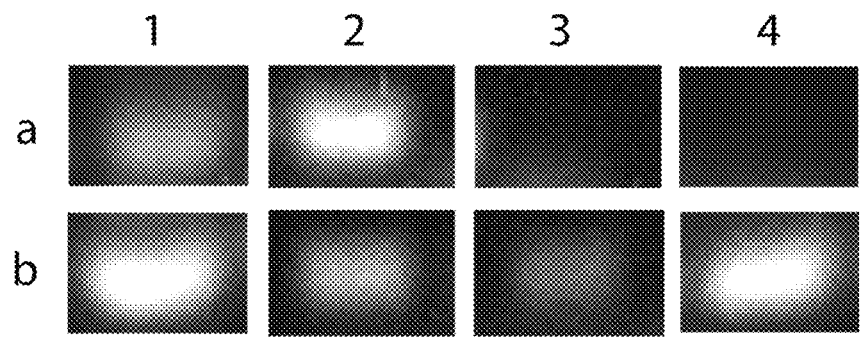
FIG. 1A: Skin punch biopsies from two different Icelandic horses affected by pruritic and allergic dermatitis conditions; two biopsies per horse, one from a lesion with dermatitis/urticaria, one from a healthy skin part. Total RNA isolation followed by PCR using specific primer for equine IL-31 (eIL-31) and equine beta-actin (eβactin). Lane 1 dermatitis lesion horse 1, lane 2, dermatitis and urticaria lesion horse 2, lane 3, healthy skin horse 1, lane 4, healthy skin horse 2. Row a, eIL-31 mRNA, row b, eβactin mRNA.

Equine IL-31 mRNA was found to be expressed in skin lesions from sites with pruritus-accompanied allergic dermatitis in horses (FIG. 1A, row a, lane 1 & 2), whereas it was absent in healthy horse skin samples (FIG. 1A, row a, lane 3 & 4). Control mRNA βactin was amplified in all samples (FIG. 1A, row b, lane 1-4). Typically, in skin lesions of horses affected with (allergic) dermatitis, high contents of eosinophils in basically all skin layers are present. The latter is in contrast to skin lesions in humans or other domesticated mammals such as in a dog, where eosinophils are not involved in skin pathology. Thus, the significant expression of equine IL-31 mRNA in skin lesions from sites with pruritus-accompanied allergic dermatitis in horses strongly suggest the involvement of equine IL-31 in pruritus-accompanied allergic dermatitis.

Figure 1B:
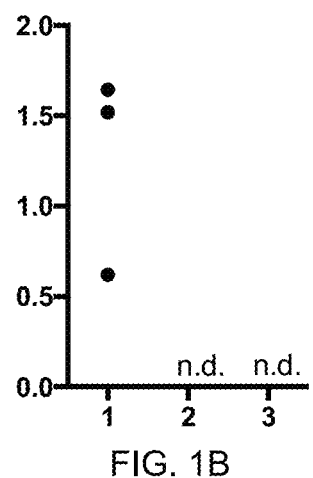
FIG. 1B: eIL-31 mRNA levels, shown as per mille expression of eβactin housekeeping gene, of skin biopsies taken from itchy lesion sites (1), matched healthy skin from the same horses (2), and healthy skin from healthy horses (3), n=3, n.d.: not detectable.

Expression of equine IL-31 mRNA in relation to housekeeping gene βactin from skin biopsies showed that only the samples extracted from itchy skin lesions did express equine IL-31 mRNA, whereas eIL-31 was not detectable in matched healthy skin samples from the same horses and also was absent in healthy skin from horses that did not suffer from itching (FIG. 1B).

Example 2

In-Vitro Stimulation of T Cells by PBMCs Isolated from Allergic Horses

A. In-Vitro Stimulation Assay

Quantification of equine IL-31 levels in Th cell subsets in blood of allergic dermatitis affected versus healthy horses by in vitro stimulation assays. Blood from IBH affected or healthy horses was taken and PBMCs were isolated by Ficoll.

Antigen uptake was done using allergen extract and/or recombinant allergens, respectively, and Concanavalin A (Con A) as positive control. Negative control was medium only. PBMCs were cultured in the presence of stimulant for 24 and 48 hours.

Alternatively, equine monocytes are isolated by magnetic separation (MACS technology, Miltenyi Biotec GmbH, Bergisch-Gladbach, Germany) according to standard protocols by the manufacturer, using a monoclonal anti-equine CD14 antibody (clone 105) and secondary goat anti-mouse coated micro beads. Cells is then separated on a LS column (Miltenyi Biotec) and differentiation into MoDC induced by culturing $CD14^+$ monocytes for three days in the presence of recombinant equine IL-4 and GM-CSF as described in (Moyo et al., 2013). For maturation, dendritic cells are exposed overnight to a maturation cocktail comprising 1 μg/ml LPS (Sigma-Aldrich St. Louis Mo., USA), 1 μg/ml prostaglandin $E_2$ (Enzo Life Sciences, Exeter, UK), 20 ng/ml equine tumor necrosis factor-α, 10 ng/ml equine IL-1β, 20 ng/ml equine IL-6 and 100 ng/ml equine IFN-γ (all R&D Systems, Abingdon, UK) according to Moyo et al (2013). Antigen uptake is done using allergen extract and/or recombinant allergens, respectively, and tetanus toxoid peptide as positive control. T cells is co-cultured for 24 hours with the antigen-loaded APCs.

B. RNA Isolation and cDNA Transcription of PBMC Cells

Total RNA was isolated from PBMC cells using Nucleo-Spin® RNA XS Kit (Macherrey-Nagel) including DNase I treatment and inactivation. RNA was transcribed into cDNA using Reverse Transcription System (Promega) and eIL-31 mRNA level and housekeeping βactin gene copy numbers were quantified by qPCR.

C. Equine IL-31 RNA Quantification

Equine IL-31 levels produced by Th2 cells were quantified on mRNA level from cell extracts by qPCR.

qPCR:

Amplification of eIL-31 eβactin in skin biopsies using the gene-specific primers for eIL-31 (forward primer: AACAAAGAGAAGGGAGTGC—SEQ ID NO:11; reverse primer: GCTGAGCTGTTGATGTTGC—SEQ ID NO:12) and eβactin (forward primer: CCAGCACGATGAAGAT-CAAG—SEQ ID NO:13; reverse primer: GTGGACAAT-GAGGCCAGAAT—SEQ ID NO:14). The PCR was done using FastStart Universal SYBR Green Master (Roche).

Figure 1C:
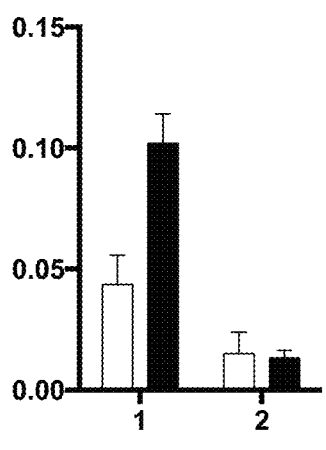
FIG. 1C: In vitro eIL-31 expression of *Culicoides nubeculosus* (Cul n) or *Culicoides obsoletus* (Cul o) allergen stimulated peripheral blood mononuclear cells (PBMCs) from IBH-affected horses (1) and healthy horses (2). Percentage of eIL-31 expression levels relative to eβactin levels is shown.

Expression of eIL-31 mRNA relative to housekeeping gene eβactin upon *Culicoides* allergen stimulated PBMCs from IBH-affected horses and healthy non-IBH horses (FIG. 1C). IL-31 expression is increased in IBH-affected horses upon allergen stimulation over medium stimulation, whereas medium and allergen stimulation is comparable in healthy horses.

Intracellular Cytokine Staining of IL-31 by Flow Cytometry

Intracellular equine IL-31 levels within Th2 cells are quantified on protein level by flow cytometry.

Example 3

Cloning, Expression and Purification of Equine IL-31 (eIL-31)

A. Cloning of eIL-31-C-His and Expression as Inclusion Bodies in *E. coli*

The DNA sequence encoding for mature eIL-31 (SEQ ID: NO. 1) were generated by gene-synthesis.

In addition a linker (GGC) was added C-terminally. This insert was flanked by 5' NdeI and 3' XhoI and was integrated into pET 42b (+), containing a hexa His-tag (to facilitate purification) and stop codon in frame. The construct was termed pET42b-eIL-31 (SEQ ID NO:22). Fidelity of the cloning procedure was confirmed by DNA sequencing. The construct pET42b-eIL-31 (SEQ ID NO:22) was transformed into *E. coli* strain BL21-DE3. The recombinant protein expressed in *E. coli* is termed eIL-31-C-His (SEQ ID NO:2).

A larger scale expression of eIL-31-C-His from clone pET42b-eIL31-C-His in BL21-DE3 cells was performed. For this purpose, clonal BL21-DE3 cells harboring pET42b-eIL31-C-His were grown over night in 180 ml of LB containing 50 mg/L Kanamycin. Inoculate with this culture 10 L LB containing 50 mg/L Kanamycin. The culture was grown to an optical density, $OD_{600\ nm}$, of 0.7 and expression induced for 4 hours by adding 10 ml of a 1.0 M stock of Isopropyl β-D-Thiogalactopyranoside (IPTG). Recombinant eIL-31-C-His was expressed in an insoluble form and located in the inclusion body fraction of induced cells. Expression of eIL-31-C-His was confirmed in the flowing manner. The culture was taken 4 hours after induction and centrifuged for 10 min at 4200×g at 4° C. The pellet was resuspended with resuspension buffer (100 mM Tris/HCl pH 8.0 at 4° C., 1 mM EDTA) (3 ml/g of cells) using an ultraturex (800 rpm). Resuspended cells were collected in Falcon tubes and shock freeze in liquid nitrogen and stored at −20° C. overnight. Resuspended cells were unfrozen at room temperature and open cells by a cell-cracker or dounce homogenizer and sonicator (50 µl sample for gel analysis: sample A=lysate, 50 µl). 0.5 volumes of cold triton buffer (60 mM EDTA, 1.5 M NaCl, adjust to pH 7.0 with NaOH then add 6% (v/v) Triton-X-100) were added and stirred for 30 min at 4° C. Thereafter, lysate was centrifuged for 30 min at 48000×g and 4° C. (50 µl sample for gel analysis: sample B=soluble fraction, 50 ml). Inclusion bodies were resuspend in washing buffer (100 mM Tris/HCl pH 8.0 at 4° C., 20 mM EDTA) with ultraturrax and centrifuged for 10 min at 48000×g and 4° C. This washing step was repeated four times to remove triton-x 100 and finally inclusion bodies were stored at −20° C. Inclusion bodies were unfrozen at room temperature and were solubilized by resuspension in solubilization buffer (6 M GdmCl, 20 mM Immidazol, 100 mM Tris-HCl pH 8 at room temperature) (20 ml/g of inclusion bodies) using ultraturex and stirring 1-2 h at room temperature. Solubilized inclusion bodies were ultra-centrifuged for 30 min at 15° C. at 100000×g on average (50 µl sample for gel analysis: sample C=solubilized IBs 50 µl).

B. Purification and Refolding of eIL-31-C-His

The protein was purified via the His-tag by Ni-NTA resin (Ni-NTA Sepharose 6 Fast Flow, Amersham, CatNo 17-5318-01 or Ni-NTA Sepharose SUperflow, Quiagen, CatNo 1018142) column with solubilization buffer as binding buffer A and elution by buffer B (6 M GdmCl, 100 mM NaH$_2$PO$_4$, 10 mM TrisHCl, pH 4.5) (50 µl sample for gel analysis: sample D=flow thru NiNTA; 50 µl, sample E=peak NiNTA 50 µl). Purification was analyzed by SDS-PAGE. The fractions from the elution step containing eIL-31-C-His were pooled and dialyzed against 6 M GdmCl, 100 mM NaH$_2$PO$_4$, 10 mM Tris, pH 8.0 for 2 h at room temperature using a 8 kDa cut-off membrane.

Insoluble eIL-31-C-His was extracted from detergent washed inclusion bodies with 6M guanidine hydrochloride. Different washing steps were analyzed by SDS-PAGE (FIG. 2A):

lysate (FIG. 2A, lane 1), soluble fraction (FIG. 2A, lane 2), solubilized inclusion bodies (FIG. 2A, lane 3). The solubilized protein was purified by metal chelate affinity chromatography and analyzed by SDS-PAGE (FIG. 2A, lane 4, pooled fractions eluate). Recombinant eIL-31-C-His was found to be highly enriched by this procedure. The native protein was assessed by SDS-PAGE performed under non-reducing conditions (FIG. 2B, lane 1) and mainly monomeric protein was found. The denatured protein was subjected to a refolding procedure as described below and optionally further purified by size exclusion chromatography.

In order to refold eIL-31-C-His, the protein was dialyzed sequentially by the following buffers: buffer 1 (2 M Urea, 50 mM NaH$_2$PO$_4$, 5 mM Glutathione reduced, 0.5 mM Gluthatione oxidized, 0.5 M Arginine, 10% Glycerol), buffer 2 (50 mM NaH$_2$PO$_4$, 5 mM Glutathione reduced, 0.5 mM Gluthatione oxidized, 0.5 M Arginine, 10% Glycerol), buffer 3a (50 mM NaH$_2$PO$_4$, 0.5 M Arginine, 10% Glycerol), buffer 3b (50 mM NaH$_2$PO$_4$, 10% Glycerol), buffer 4 (PBS). Optionally refolded protein was concentrated by Centrifugal Filters (Amicon, Ultrafree-15 Millipore, 10 kDa cut-off) and purified on a HiLoad 26/600 Superdex 75 prep grade (GE Healthcare, CatNo 28-9893-34) with PBS buffer. Eluted fractions were pooled and analyzed by a non-reducing SDS-PAGE (with SDS, no DTT, no heating of samples). Protein concentration was measured by UV-VIS or Bradford assay.

The ability of purified recombinant eIL-31-C-His to form dimers after refolding was assessed by SDS-PAGE performed under non-reducing conditions (FIG. 2B, lane 2). As judged by the molecular mass of approximately 33 kDa, eIL-31-C-His was demonstrated to partially exist in dimeric structure.

C. Biological Activity of Recombinant Refolded Equine eIL-31-C-His eIL-31-C-His was injected subcutaneously into the neck of a horse. Itch was defined as ≥5 seconds itching at the injection site (neck). The number of scratching/itching per hour was counted for 5 hours in total starting 1 hour post injection. Itching after injection with eIL-31-C-His was compared with injection of eIL-5-C-His control. An increased number of itching was recorded for eIL-31-C-His than for the control (FIG. 2C).

Example 4

Cloning, Expression and Purification of Equine Interleukin-5 (eIL-5)

A. Cloning of eIL-5—C-His and Expression as Inclusion Bodies in *E. coli*

The DNA sequence encoding for mature eIL-5 (mature Interleukin-5, *Equus caballus*; UniProt 002699) were generated by gene-synthesis. SEQ ID NO:6.

In addition a linker (GGC) was added C-terminally. This insert was flanked by 5' NdeI and 3' XhoI and was integrated into pET 42b (+), containing a hexa His-tag (to facilitate purification) and stop codon in frame. The construct was termed pET42b-eIL-5 (SEQ ID NO:23). Fidelity of the cloning procedure was confirmed by DNA sequencing. The construct pET42b-eIL-5 (SEQ ID NO:23) was transformed into E. coli strain BL21-DE3. The recombinant protein expressed in E. coli is termed eIL-5-C-His (SEQ ID NO:7). Analogously, SEQ ID NO:8, SEQ ID NO:9 and SEQ ID NO:10 have been prepared, all comprising a cysteine residue comprising linker and (except SEQ ID NO:10) a His-tag, with SEQ ID NO:8, SEQ ID NO:9 and SEQ ID NO:10 comprising a linker (GGC) and (except SEQ ID NO:10) a His-tag C-terminally. SEQ ID NO:7, SEQ ID NO:8 and SEQ ID NO:9, in particular SEQ ID NO:7 and SEQ ID NO:8 are interchangeably termed herein as "eIL-5-C-His". Furthermore, when it is referred to eIL-5-C-His within this example section and the described figures, one of these eIL-5-C-His recombinant proteins have been used, in various examples even more than one or all been used in repeated experiments. Very preferred used eIL-5-C-His are SEQ ID NO:7 and SEQ ID NO:8. A larger scale expression of eIL-5-C-His from clone pET42b-eIL5-C-His in BL21-DE3 cells was performed. For this purpose, clonal BL21-DE3 cells harboring pET42b-eIL-5-C-His were grown over night in 180 ml of LB containing 50 mg/L Kanamycin. Inoculate with this culture 10 L LB containing 50 mg/L Kanamycin. The culture was grown to an optical density, OD600 nm, of 0.7 and expression induced for 4 hours by adding 10 ml of a 1.0 M stock of Isopropyl β-D-Thiogalactopyranoside (IPTG). Recombinant eIL-5-C-His was expressed in an insoluble form and located in the inclusion body fraction of induced cells. Expression of eIL-5-C-His was confirmed in the flowing manner. The culture was taken 4 hours after induction and centrifuged for 10 min at 4200×g at 4° C. The pellet was resuspended with resuspension buffer (100 mM Tris/HCl pH 8.0 at 4° C., 1 mM EDTA) (3 ml/g of cells) using an ultraturex (800 rpm). Resuspended cells were collected in Falcon tubes and shock freeze in liquid nitrogen and stored at −20° C. overnight. Resuspended cells were unfrozen at room temperature and open cells by a cell-cracker or dounce homogenizer and sonicator (50 µl sample for gel analysis: sample A=lysate, 50 µl). 0.5 volumes of cold triton buffer (60 mM EDTA, 1.5 M NaCl, adjust to pH 7.0 with NaOH then add 6% (v/v) Triton-X-100) were added and stirred for 30 min at 4° C. Thereafter, lysate was centrifuged for 30 min at 48000×g and 4° C. (50 µl sample for gel analysis: sample B=soluble fraction, 50 ml). Inclusion bodies were resuspended in washing buffer (100 mM Tris/HCl pH 8.0 at 4° C., 20 mM EDTA) with ultraturrax and centrifuged for 10 min at 48000×g and 4° C. This washing step was repeated four times to remove triton-x 100 and finally inclusion bodies were stored at −20° C. Inclusion bodies were unfrozen at room temperature and were solubilized by resuspension in solubilization buffer (6 M GdmCl, 20 mM Immidazol, 100 mM Tris-HCl pH 8 at room temperature) (20 ml/g of inclusion bodies) using ultraturex and stirring 1-2 h at room temperature. Solubilized inclusion bodies were ultra-centrifuged for 30 min at 15° C. at 100000×g on average (50 µl sample for gel analysis: sample C=solubilized IBs 500.

B. Purification and Refolding of eIL-5-C-His

The protein was purified via the His-tag by Ni-NTA resin (Ni-NTA Sepharose 6 Fast Flow, Amersham, CatNo 17-5318-01 or Ni-NTA Sepharose SUperflow, Quiagen, CatNo 1018142) column with solubilization buffer as binding buffer A and elution by buffer B (6 M GdmCl, 100 mM NaH$_2$PO$_4$, 10 mM TrisHCl, pH 4.5) (50 µl sample for gel analysis: sample D=flow thru NiNTA; 50 µl, sample E=peak NiNTA 50 µl). Purification was analyzed by SDS-PAGE. The fractions from the elution step containing eIL-5-C-His were pooled and dialyzed against 6 M GdmCl, 100 mM NaH$_2$PO$_4$, 10 mM Tris, pH 8.0 for 2 h at room temperature using a 10 kDa cut-off membrane.

Insoluble eIL-5-C-His was extracted from detergent washed inclusion bodies with 6M guanidine hydrochloride. Different washing steps were analyzed by SDS-PAGE (FIG. 1): lysate (FIG. 3A, lane 1), soluble fraction (FIG. 3A, lane 2), solubilized inclusion bodies (FIG. 3A, lane 3). The solubilized protein was purified by metal chelate affinity chromatography and analyzed by SDS-PAGE (FIG. 3A, lane 4, flow through, lane 5, pooled fractions eluate). Recombinant eIL-5-C-His was found to be highly enriched by this procedure. The native protein was assessed by SDS-PAGE (FIG. 3B) performed under non-reducing conditions (with SDS, no DTT, no heating of samples) (FIG. 3B, lane 1) and mainly monomeric protein was found. The denatured protein was subjected to a refolding procedure as described below and optionally further purified by size exclusion chromatography.

In order to refold eIL-5—C-His, the protein was dialyzed sequentially by the following buffers: buffer 1 (2 M Urea, 50 mM NaH$_2$PO$_4$, 5 mM Glutathione reduced, 0.5 mM Gluthatione oxidized, 0.5 M Arginine, 10% Glycerol), buffer 2 (50 mM NaH$_2$PO$_4$, 5 mM Glutathione reduced, 0.5 mM Gluthatione oxidized, 0.5 M Arginine, 10% Glycerol), buffer 3 (50 mM NaH$_2$PO$_4$, 10% Glycerol), buffer 4 (PBS). Optionally refolded protein was concentrated by Centrifugal Filters (Amicon, Ultrafree-15 Millipore, 10 kDa cut-off) and purified on a HiLoad 26/600 Superdex 75 prep grade (GE Healthcare, CatNo 28-9893-34) with PBS buffer. Eluted fractions were pooled and analyzed by a non-reducing SDS-PAGE. Protein concentration was measured by UV-VIS or Bradford assay.

Since biologically active native IL-5 is a disulfide-linked homodimer, the ability of purified recombinant eIL-5—C-His to form dimers after refolding was assessed by SDS-PAGE performed under non-reducing conditions (FIG. 3B, lane 2). As judged by the molecular mass of approximately 28 kDa, eIL-5—C-His was demonstrated to be dimeric in nature indicating conservation of the native tertiary structure.

C. Structure of Recombinant Homodimer Enriched eIL-5—C-His

CD spectroscopy by far-UV showing α-helices and β-sheets was measured in order to confirm correct secondary structure (FIG. 3C).

Mass spectrometry (MALDI/MS/MS of digested eIL-5—C-His followed by HPLC) was performed in order to confirm besides secondary also the primary, tertiary and quaternary structure of the protein. Typically IL-5 monomers are linked as homodimers by two intermolecular disulfide bridges leading to a head to tail position of the two monomers.

The ability of a commercially available antibody binding to the recombinant eIL-5—C-His was tested by ELISA (FIG. 3D). Maxisorp 96 well ELISA plates (Nunc) were coated over night with 50 µl of anti-His antibody at 0.5 mg/L. Plates were washed 3 times with PBS-Tween 0.1% (v/v) (PBST) then blocked with Superblock (Thermo Scientific) for 1 h at 37° C. Plates were washed twice with PBST and purified recombinant eIL-5—C-His (10 mg/L) was added and incubated for 1 h. Then plates were washed 3 times with PBST and anti eIL-5 antibody (Equine IL-5 affinity purified polyclonal antibody, R&D Systems, UK, CatNo AF2470) was titrated down from 4 µg/ml in 1/3 dilutions and incubated at room temperature for 2 h. The plates were subsequently washed 3 times with PBST and incubated with a secondary anti-goat IgG conjugated with HRP (dilution 1:2000) at room temperature for 30 min. The plates were again washed 3 times with PBS and 50 µl/well developing solution (TMB) were added. After 2 minutes of reaction at room temperature the ELISA was stopped with 25 µl per well 5% $H_2SO_4$. Absorbance was measured at 450 nm on a Tecan M200 spectrophotometer (Tecan, Austria).

The proper refolding of recombinant eIL-5—C-His was measured by circular dichroism (CD) spectroscopy and in majority α helices but also β sheets could be found as expected (FIG. 3C). The linkage of two monomers by two intermolecular disulfide bridges was further confirmed by MALDI/MS/MS. MSMS fractions of mass 2505, 2633, and 2761 m/z show the typical disulfide fragment pattern 32/2/32. Two monomers are linked via 2 disulfide bridges as Cys44 is linked to Cys 86 intermolecularly (spectra not shown). Furthermore, refolded equine IL-5—C-His was detectable by a commercially available anti-equine IL-5 antibody in an ELISA (FIG. 3D).

Example 5

Coupling of eIL-31 Antigen to VLP, Immunization of Horses and Demonstration of Efficacy in Horses with Pruritus Induced Dermatitis A. Coupling Equine IL-31-C-His to VLP of Qβ

Qβ VLP comprising coat proteins of SEQ ID NO:24 were produced as described in WO 02/056905 and reacted with a 7.5 fold molar excess of the heterobifunctional cross-linker succinimidyl-6(β-maleimidopropionamido)hexanoate (SMPH) (Pierce). Unreacted crosslinker was removed by passage over a PD-10 desalting column (GE Healthcare). The recombinant, purified and refolded eIL-31-C-His was reduced for 1 h with an equimolar excess amount of tri(2-carboxyethyl)phosphine hydrochloride (TCEP) in PBS pH 8.0 to reduce the cysteine residue contained in the linker. The reduced eIL-31-C-His was then mixed with the derivatized Qβ VLPs at a molar ratio of Qβ monomer to eIL-31-C-His protein of 1:1 and co-incubated for 4 hours at 22° C. to allow cross-linking. The reaction was dialysed 12 hours against PBS pH 7.4 using a 300 kDa cut-off dialysis membrane or free uncoupled eIL-31-C-His was removed by either size exclusion chromatography or tangential flow filtration using 100 kDa MWCO.

Analysis: Coomassie staining of SDS-PAGE (FIG. 4A). Qβ, eIL-31-C-His and eIL-31-C-His-Qβ VLP were separated by SDS-PAGE. Subsequently gel was stained with Coomassie-Blue (0.025% Coommassie Brilliant BlueR-250, 40% methanol, 10% acetic acid) and de-stained with destainer (40% methanol, 10% acetic acid).

Western blot staining with anti-His antibody (FIG. 4B). Qβ, eIL-31-C-His and eIL-31-C-His-Qβ VLP were separated by SDS-PAGE and electroblotted onto a nitrocellulose membrane. The membrane was blocked for 1 h with 5% (w/v) BSA powder in PBST, then incubated with 10 ml of 1:800 diluted anti-His antibody (Penta-His Antibody, BSA-free, mouse monoclonal IgG1, CatNo. 34660) in 1% BSA (w/v) powder in PBST. The membrane was washed with PBST for 15 minutes and then incubated for 1 h with 10 ml 1% (w/v) BSA in PBST anti-mouse IgG antibody conjugated with horse radish peroxidase (HRP) at a dilution of 1:10,000. The membrane was washed for 15 minutes in PBS and developed with ECL (Amersham Pharmacia, Sweden) and exposed to Photographic film.

The covalent chemical coupling of eIL-31-C-His to virus-like particle Qβ was assessed by SDS-PAGE and Western blot analyses. Coomassie blue stained gels of the coupling reaction demonstrated the appearance of bands with molecular weights corresponding to those predicted for equine IL-31-C-His covalently linked to Qβ (FIG. 4A). Furthermore, Western blot analyses showed co-localization of these bands when stained with anti-His antibody (FIG. 4B).

B. Coupling of eIL31-C-His to CMVtt830 VLP

CMVtt830 VLP were produced as described above and were reacted with a 10 fold molar excess of the heterobifunctional cross-linker succinimidyl-6(β-maleimidopropionamido)-hexanoate (SMPH) (Pierce). Unreacted crosslinker was removed by passage over a PD-10 desalting column (GE Healthcare). The recombinant, purified and refolded eIL-31-C-His was reduced for 1 h with an equimolar excess amount of tri(2-carboxyethyl)phosphine hydrochloride (TCEP) in 20 mM $Na_2PO_4$/2 mM EDTA, pH 7.5 to reduce the cysteine residue contained in the linker. The reduced eIL-31-C-His was then mixed with the derivatized CMVtt830 VLPs at a molar ratio of VLP monomer to eIL-31-C-His protein of 1:1 and co-incubated for 4 hours at 22° C. to allow cross-linking. The reaction was dialysed 12 hours against 20 mM $Na_2PO_4$/2 mM EDTA, pH 7.5 using a 300 kDa cut-off dialysis membrane or free uncoupled eIL-31-C-His was removed by either size exclusion chromatography or tangential flow filtration using 100 kDa MWCO.

Analysis: Coomassie staining of SDS-PAGE (FIG. 4C): eIL-31-C-His, CMVtt830, and eIL31-C-His-CMVtt830 VLP were separated by SDS-PAGE. Subsequently gel was stained with Coomassie-Blue (0.025% Coomassie Brilliant BlueR-250, 40% methanol, 10% acetic acid) and de-stained with destainer (40% methanol, 10% acetic acid).

Western blot staining with anti-His antibody (FIG. 4D): eIL-31-C-His, CMVtt830, and eIL31-C-His-CMVtt830 VLP were separated by SDS-PAGE and electroblotted onto a nitrocellulose membrane. The membrane was blocked for 1 h with 5% (w/v) BSA powder in PBST, then incubated with 10 ml of 1:1000 diluted anti-His antibody (monoclonal anti-His Tag antibody HRPO conjugate, Novagen CatNo. 71840) in 1% BSA (w/v) powder in PBST. The membrane was washed with PBST for 15 minutes and then developed with ECL (Amersham Pharmacia, Sweden) and exposed to Photographic film.

The covalent chemical coupling of eIL31-C-His to CMVtt830 VLP was assessed by SDS-PAGE and Western blot analyses. Coomassie blue stained gels of the coupling reaction demonstrated the appearance of bands with molecular weights corresponding to those predicted for equine IL31-C-His covalently linked to CMV-tt830, respectively (FIG. 4C). Furthermore, Western blot analyses showed co-localization of these bands when stained with anti-His antibody (FIG. 4D).

C. Immunization Protocol

Horses with eIL-31-C-His-VLP Treatment and Vaccination, Respectively, Alone.

In order to generate self-reactive antibodies to equine IL-31, horse was injected subcutaneously on day 0, 28, and 101 with 300 µg of eIL-31-C-His-CMVtt830 in 1,000 µl of PBS. Horses were bled prior to immunization and at least on day 41 of the immunization protocol and various additional time points post day 41. Sera were analyzed by ELISA (FIG. 5A).

Horses with eIL-5—C-His-VLP/eIL-31-C-His-VLP Combinatory Treatments and Vaccinations (Separate Injections), Respectively.

In order to generate self-reactive antibodies to equine IL-5 and equine IL-31, horse was injected subcutaneously on day −62 and −40 and with eIL5-C-His-Qβ vaccine in 1,000 µl of PBS and on day 0 and 19 with 300 µg of eIL-31-C-His-Qβ vaccine in 1,000 µl of PBS. Horse was bled prior to immunization and on day 42 or on day 93 and 118. Sera were analyzed by ELISA (FIG. 5B).

Horses with eIL-5-C-His-VLP/eIL-31-C-His-VLP Combination Treatments and Vaccinations, Respectively.

In order to generate self-reactive antibodies to equine IL-5 and equine IL-31, horse was injected subcutaneously on days 0, 28, 105 with 300 µg of each eIL-5-C-His-CMVtt830 and eIL-31-C-His-CMVtt830 in a total of 2,000 µl of 20 mM $Na_2PO_4$/2 mM EDTA, pH 7.5. Hors was bled prior to immunization and at least on day 42 and 84, of the immunization protocol and various additional time points post day 84. Sera are analyzed by ELISA (FIG. 5C).

Horses with eIL-5—C-His-VLP/eIL-31-C-His-VLP Combinatory Treatments and Vaccinations (Separate Injections, Same Day but Targeting Different Lymph Nodes), Respectively.

In order to generate self-reactive antibodies to equine IL-5 and equine IL-31, horse was injected subcutaneously on days 0 and 28 with 300 µg of each eIL-5—C-His-CMVtt830 on the left body site and eIL-31-C-His-CMVtt830 on the right body site, each in 1,000 µl of 20 mM $Na_2PO_4$/2 mM EDTA, pH 7.5. Horses were bled prior to immunization and at least on day 42 of the immunization protocol and various additional time points post day 42. Sera were analyzed by ELISA (FIG. 5D).

Horses with eIL-31-C-His-VLP Treatments and Vaccinations Post Previous eIL-5—C-His-VLP Treatments and Vaccination, Respectively.

In order to generate self-reactive antibodies to equine IL-31 post prior eIL-5—C-His-CMVtt830 vaccination, horses were injected subcutaneously on days 0 and 28 with 300 µg of eIL-31-C-His-CMVtt830 in 1,000 µl of 20 mM $Na_2PO_4$/2 mM EDTA, pH 7.5. Horses were bled prior to immunization and at least on day 42 of the immunization protocol and various additional time points post day 42. Sera were analyzed by ELISA (FIG. 5E).

D. Sera Analysis by ELISA:

Horses with eIL-31-C-His-VLP Treatment and Vaccination, Respectively, Alone:

Maxisorp 96 well ELISA plates (Nunc) were coated over night with 50 µl purified eIL-31-C-His (5 µg/ml). Plates were washed 3 times with PBST blocked with 5% BSA/PBST (Thermo Scientific) for 2 hour at room temperature. Then plates were washed 3 times with PBST and three-fold dilutions of horse sera was added in Superblock and incubated at room temperature for 2 h. The plates were subsequently washed 3 times with PBST and incubated with anti-equine IgG conjugated with HRP (dilution 1:2000) at room temperature for 30 min. The plates were again washed 4 times with PBS and 50 µl/well developing solution (TMB) was added. After approximately 2 minutes of reaction at room temperature the ELISA was stopped with 25 µl per well 5% $H_2SO_4$. Absorbance was measured at 450 nm on a Tecan M200 spectrophotometer or Tecan Spark (Tecan, Austria).

Preimmune sera and post immunization day 41 sera from horse vaccinated with eIL-31-C-His-CMVtt830 alone was collected and analyzed by ELISA. Horse sera was blotted as delta $OD_{50}$ ($\Delta OD_{50}$) values, which were calculated from OD450 values for each dilution subtracted by corresponding naïve serum dilution. The result of vaccination in horses shows that immunological tolerance towards the self-antigens IL-31 was overcome (FIG. 5A). Half maximal titer at peak of response were above 1:1,000.

Horses with eIL-5-C-His-VLP/eIL-31-C-His-VLP Combinatory Treatment and Vaccination, Respectively:

Maxisorp 96 well ELISA plates (Nunc) were coated over night with 50 µl purified eIL-5-C-His (5 µg/ml) or eIL-31-C-His (5 µg/ml). Plates were washed 3 times with PBST blocked with 5% BSA/PBST (Thermo Scientific) for 2 hour at room temperature. Then plates were washed 3 times with PBST and three-fold dilutions of antigen pre-absorbed horse sera (for eIL-31-C-His ELISA: pre-absorption with eIL-5-C-His antigen (5 µg/ml); for eIL-5-C-His ELISA: pre-absorption with eIL-31-C-His antigen (5 µg/ml); pre-incubation 30 min at room temperature) were added in Superblock and incubated at room temperature for 2 h. The plates were subsequently washed 3 times with PBST and incubated with anti-equine IgG conjugated with HRP (dilution 1:2000) at room temperature for 30 min. The plates were again washed 4 times with PBS and 50 µl/well developing solution (TMB) are added. After approximately 2 minutes of reaction at room temperature the ELISA was stopped with 25 µl per well 5% $H_2SO_4$. Absorbance was measured at 450 nm on a Tecan M200 spectrophotometer or Tecan Spark (Tecan, Austria).

Preimmune sera and post immunization day 42, 93 or 118 sera, respectively, from a horse vaccinated with eIL-5-C-His-Qβ/eIL-31-C-His-Qβ was collected and analyzed by ELISA. Horse sera were blotted as delta $OD_{50}$ ($\Delta OD_{50}$) values, which were calculated from OD450 values for each dilution subtracted by corresponding naïve serum dilution. The result of vaccination in horses shows that immunological tolerance towards the self-antigens IL-5 and IL-31 was overcome (FIG. 5B). Half maximal titer at peak of response were approximately 1:1,000.

Horses with eIL-5-C-His-VLP/eIL-31-C-His-VLP Combination Treatment and Vaccination, Respectively:

Maxisorp 96 well ELISA plates (Nunc) were coated over night with 50 µl purified eIL-5—C-His (5 µg/ml) or eIL-31-C-His (5 µg/ml). Plates were washed 3 times with PBST blocked with 5% BSA/PBST (Thermo Scientific) for 2 hours at room temperature. Then plates were washed 3 times with PBST and three-fold dilutions of antigen pre-absorbed horse sera (for eIL-31-C-His ELISA: pre-absorption with eIL-5—C-His antigen (5 µg/ml); for eIL-5—C-His ELISA: pre-absorption with eIL-31-C-His antigen (5 µg/ml); pre-incubation 30 min at room temperature) were added in Superblock and incubated at room temperature for 2 h. The plates were subsequently washed 3 times with PBST and incubated with anti-equine IgG conjugated with HRP (dilution 1:2000) at room temperature for 30 min. The plates were again washed 4 times with PBS and 50 µl/well developing solution (TMB) was added. After approximately 2 minutes of reaction at room temperature the ELISA was stopped with 25 µl per well 5% $H_2SO_4$. Absorbance was measured at 450 nm on a Tecan M200 spectrophotometer or Tecan Spark (Tecan, Austria).

Preimmune sera and post immunization day 42, 84, and later sera, respectively, from horses vaccinated with eIL-5-C-His-CMVtt830/eIL-31-C-His-CMVtt830 was collected and analyzed by ELISA. Horse sera were blotted as delta $OD_{50}$ ($\Delta OD_{50}$) values, which were calculated from OD450 values for each dilution subtracted by corresponding naïve serum dilution. The result of vaccination in horses shows that immunological tolerance towards the self-antigens IL-5 and IL-31 was overcome (FIG. 5C). Half maximal titer at peak of both, anti-IL-5 and anti-IL-31, responses were approximately 1:1,000.

Horses with eIL-5—C-His-VLP/eIL-31-C-His-VLP Combinatory Treatment and Vaccination (with Separate Injections, Same Day but Targeting Different Lymph Nodes), Respectively:

Maxisorp 96 well ELISA plates (Nunc) were coated over night with 50 μl purified eIL-5—C-His (5 μg/ml) or eIL-31-C-His (5 μg/ml). Plates were washed 3 times with PBST blocked with 5% BSA/PBST (Thermo Scientific) for 2 hours at room temperature. Then plates were washed 3 times with PBST and three-fold dilutions of antigen pre-absorbed horse sera (for eIL-31-C-His ELISA: pre-absorption with eIL-5—C-His antigen (5 μg/ml); for eIL-5—C-His ELISA: pre-absorption with eIL-31-C-His antigen (5 μg/ml); pre-incubation 30 min at room temperature) were added in Superblock and incubated at room temperature for 2 h. The plates were subsequently washed 3 times with PBST and incubated with anti-equine IgG conjugated with HRP (dilution 1:2000) at room temperature for 30 min. The plates were again washed 4 times with PBS and 50 μl/well developing solution (TMB) was added. After approximately 2 minutes of reaction at room temperature the ELISA was stopped with 25 μl per well 5% $H_2SO_4$. Absorbance was measured at 450 nm on a Tecan M200 spectrophotometer or Tecan Spark (Tecan, Austria).

Preimmune sera and post immunization day 42 from three horses vaccinated with eIL-5-C-His-CMVtt830/eIL-31-C-His-CMVtt830 was collected and analyzed by ELISA. eIL-5-C-His-CMVtt830/eIL-31-C-His-CMVtt830 vaccinations have been injected separately. The vaccines were injected on different body sites in order to target separate lymph nodes. Antibody titers were assessed upon two vaccinations and effects of vaccination on dermatitis disease symptoms, pruritus and blood eosinophilia are recorded. Horse sera were blotted as delta $OD_{50}$ ($\Delta OD_{50}$) values, which were calculated from OD450 values for each dilution subtracted by corresponding naïve serum dilution. The result of vaccination in horses (n=3) shows that immunological tolerance towards the self-antigens eIL-5 and eIL-31 was overcome (FIG. 5D). Mean half maximal titers on day 42 of anti-eIL-31 responses were approximately 1:1,000, and of anti-eIL-S response approximately 1:3,000.

Horses with eIL-31-C-His-VLP Treatments and Vaccinations Post Previous eIL-5—C-His-VLP Treatments and Vaccination, Respectively:

Maxisorp 96 well ELISA plates (Nunc) were coated over night with 50 μl purified eIL-5—C-His (5 μg/ml) or eIL-31-C-His (5 μg/ml). Plates were washed 3 times with PBST blocked with 5% BSA/PBST (Thermo Scientific) for 2 hours at room temperature. Then plates were washed 3 times with PBST and three-fold dilutions of horse sera were added in Superblock and incubated at room temperature for 2 h. The plates were subsequently washed 3 times with PBST and incubated with anti-equine IgG conjugated with HRP (dilution 1:2000) at room temperature for 30 min. The plates were again washed 4 times with PBS and 50 μl/well developing solution (TMB) was added. After approximately 2 minutes of reaction at room temperature the ELISA was stopped with 25 μl per well 5% $H_2SO_4$. Absorbance was measured at 450 nm on a Tecan M200 spectrophotometer or Tecan Spark (Tecan, Austria).

Preimmune sera and post immunization day 42 from two horses vaccinated with eIL-31-C-His-CMVtt830 was collected and analyzed by ELISA. These horses had been vaccinated in the previous year with eIL-5—C-His-CMVtt830 vaccine. Antibody titers were assessed upon two vaccinations and effects of vaccination on dermatitis disease symptoms, pruritus and blood eosinophilia are recorded. Horse sera were blotted as delta $OD_{50}$ ($\Delta OD_{50}$) values, which were calculated from OD450 values for each dilution subtracted by corresponding naïve serum dilution. The result of vaccination in horses shows that immunological tolerance towards the self-antigens eIL-31 was overcome, although horses had been vaccinated in the previous year with the eIL-5—C-His-CMVtt830 vaccine using the same VLP backbone (FIG. 5E). Half maximal titers on day 42 of anti-eIL-31 responses were above 1:2'500.

E. In Vivo Efficacy:

Case Study 1:

eIL-5-C-His-Qβ/eIL-31-C-His-Qβ combinatory vaccinations. A pruritic allergic dermatitis affected Icelandic horse (positively tested for *Alnus, Rumex crispus, D. farinae, Tyrophagus, Acarus siro* and *Culicoides* by allergy screening using Greer allergens performed by IDEXX Diavet, Switzerland) was vaccinated with a combinatory vaccine of eIL-5-C-His-Qβ and eIL-31-C-His-Qβ in order to assess ability to induce auto-antibodies against IL-5 and IL-31 at the same time.

A first horse was vaccinated subcutaneously for two times using eIL-5-C-His-Qβ/eIL-31-C-His-Qβ combinatory vaccine. 300 μg of each vaccine in a total volume of 1 ml in PBS is injected subcutaneously per vaccination date. The horse was injected on day −62 and −40 and with eIL5-C-His-Qβ vaccine in 1,000 μl of PBS and on day 0 and 19 with 300 μg of eIL-31-C-His-Qβ vaccine in 1,000 μl of PBS. Antibody titers in serum from day 42, 93 and 118 were analyzed by ELISA. Antibody titer against both cytokines had been established upon combinatory vaccination with eIL-5-C-His-Qβ and eIL-31-C-His-Qβ vaccines (FIG. 5B, anti-eIL-S antibodies, black circles, anti-IL-31 antibodies, grey circles).

Case Study 2:

eIL-5-C-His-CMVtt830/eIL-31-C-His-CMVtt830 combination vaccinations. A pruritic allergic dermatitis affected Icelandic horse (positively tested for *Culex, Culicoides, Simulium* sp., *Stomoxys* c., and *Tabanus* by allergy screening using Greer allergens performed by IDEXX Diavet, Switzerland) was vaccinated with a combination vaccine consisting of eIL-5—C-His-CMVtt830 and IL-31-C-His-CMVtt830 in order to assess antibody titers and effects of vaccination on dermatitis disease symptoms, pruritus and blood eosinophilia.

A first horse was vaccinated subcutaneously for three times using eIL-5—C-His-CMVtt830/eIL-31-C-His-CMVtt830 combination vaccine. 300 μg of each vaccine in a total volume of 2 ml in 20 mM $Na_2PO_4$/2 mM EDTA, pH 7.5 is injected subcutaneously per vaccination date. The horse was injected on day 0, day 28, and day 105. Antibody titers against IL-5 and IL-31 in serum were analyzed by ELISA (FIG. 5C). Before and after vaccinations, eosinophil counts in blood were analyzed and dermatitis lesions and pruritus are scored by a symptoms scoring described in Example 7 and 8, respectively. Eosinophil levels in blood decreased upon immunization using eIL-5-C-His-CMVtt830/eIL-31-C-His-CMVtt830 combination vaccine (FIG. 5F). In line with decreasing eosinophil levels, the skin lesion scores decreased and the course of lesion scores showed reduced values compared to first measurement (FIG. 5G). Comparable to lesion score, the course of pruritus score decreased post second immunization with a long period of absent itch (FIG. 5H). When comparing mean pruritus scores from season before treatment and season with treatment, the pruritus was strongly decrease in the presence of vaccine (FIG. 5I).

Case Study 3:

Horse with eIL-31-C-His-CMVtt830 alone. A pruritic allergic dermatitis affected Icelandic horse (positively tested for *Alnus, Rumex crispus, D. farinae*, Tyrophagus, and *Acarus siro* by allergy screening using Greer allergens performed by IDEXX Diavet, Switzerland) was vaccinated with IL-31-C-His-CMVtt830 vaccine alone in order to assess antibody titers and effects of vaccination on dermatitis disease symptoms, pruritus and blood eosinophilia.

A first horse was vaccinated subcutaneously for three times using eIL-31-C-His-CMVtt830 vaccine. 300 μg of the vaccine in a total volume of 1 ml in 20 mM $Na_2PO_4$/2 mM EDTA, pH 7.5 was injected subcutaneously per vaccination date. The horse was injected on day 0, day 28, and day 101. Antibody titer against IL-31 in serum was analyzed by ELISA (FIG. 5A). Before and after vaccinations, eosinophil counts in blood were analyzed and dermatitis lesions and pruritus are scored by a symptoms scoring described in Example 7 and 8, respectively. Mean skin lesion score in the treatment season using eIL-31-C-His-CMVtt830 vaccine led to reduced scores when comparing to previous untreated season (FIG. 5J). Comparably, when comparing mean pruritus scores from season before treatment and season with treatment, the pruritus was strongly decrease in the presence of vaccine (FIG. 5K).

Example 6

Coupling of eIL-5 Antigens to Different VLPs, Immunization of Horses and Demonstration of Efficacy in IBH Prone Horses A. Coupling of eIL5-C-His to VLP of Qβ

Qβ VLP comprising coat proteins of SEQ ID NO:24 was produced as described in WO 02/056905 and reacted with a 10 fold molar excess of the heterobifunctional cross-linker succinimidyl-6(β-maleimidopropionamido)hexanoate (SMPH) (Pierce). Unreacted crosslinker was removed by passage over a PD-10 desalting column (GE Healthcare). The recombinant, purified and refolded eIL-5-C-His was reduced for 1 h with an equimolar excess amount of tri(2-carboxyethyl)phosphine hydrochloride (TCEP) in PBS pH 8.0 to reduce the cysteine residue contained in the linker. The reduced eIL-5-C-His was then mixed with the derivatized Qβ VLPs at a molar ratio of Qβ monomer to eIL-5-C-His protein of 1:2 and co-incubated for 4 hours at 22° C. to allow cross-linking. Optionally, the reaction was dialysed 12 hours against PBS pH 7.4 using a 300 kDa cut-off dialysis membrane or free uncoupled eIL-5-C-His was removed by either size exclusion chromatography or tangential flow filtration using 100 kDa MWCO.

Analysis: Coomassie staining of SDS-PAGE (FIG. 6A): Qβ, eIL5-C-His and eIL5-C-His-Qβ VLP were separated by SDS-PAGE. Subsequently gel was stained with Coomassie-Blue (0.025% Coomassie Brilliant BlueR-250, 40% methanol, 10% acetic acid) and de-stained with destainer (40% methanol, 10% acetic acid).

Western blot staining with anti-His antibody (FIG. 6B): Qβ, eIL5-C-His and IL5-C-His-Qβ vaccine were separated by SDS-PAGE and electroblotted onto a nitrocellulose membrane. The membrane was blocked for 1 h with 5% (w/v) BSA powder in PBST, then incubated with 10 ml of 1:800 diluted anti-His antibody (Penta-His Antibody, BSA-free, mouse monoclonal IgG1, CatNo. 34660) in 1% BSA (w/v) powder in PBST. The membrane was washed with PBST for 15 minutes and then incubated for 1 h with 10 ml 1% (w/v) BSA in PBST anti-mouse IgG antibody conjugated with horse radish peroxidase (HRP) at a dilution of 1:10,000.

The membrane was washed for 15 minutes in PBS and developed with ECL (Amersham Pharmacia, Sweden) and exposed to Photographic film.

The covalent chemical coupling of eIL5-C-His to the virus-like particle Qβ was assessed by SDS-PAGE and Western blot analyses. Coomassie blue stained gels of the coupling reaction demonstrated the appearance of bands with molecular weights corresponding to those predicted for equine IL5-C-His covalently linked to Qβ (FIG. 6A). Furthermore, Western blot analyses showed co-localization of these bands when stained with anti-His antibody (FIG. 6B).

B. Coupling of eIL5-C-His to CMVtt830 VLP

CMVtt830 VLP comprising modified CMV polypeptides of SEQ ID NO:20 was produced as described in WO 2016/062720 and reacted with a 10 fold molar excess of the heterobifunctional cross-linker succinimidyl-6(β-maleimidopropionamido)-hexanoate (SMPH) (Pierce). Unreacted crosslinker was removed by passage over a PD-10 desalting column (GE Healthcare). The recombinant, purified and refolded eIL-5-C-His was reduced for 1 h with an equimolar excess amount of tri(2-carboxyethyl)phosphine hydrochloride (TCEP) in PBS or 20 mM $Na_2PO_4$/2 mM EDTA, pH 7.5 to reduce the cysteine residue contained in the linker. The reduced eIL-5-C-His was then mixed with the derivatized CMVtt830 VLPs at a molar ratio of VLP monomer to eIL-5-C-His protein of 1:2 and co-incubated for 4 hours at 22° C. to allow cross-linking. Optionally, the reaction was dialysed 12 hours against PBS pH 7.4 or 20 mM $Na_2PO_4$/2 mM EDTA, pH 7.5 using a 300 kDa cut-off dialysis membrane or free uncoupled eIL-5-C-His was removed by either size exclusion chromatography or tangential flow filtration using 100 kDa MWCO.

Analysis: Coomassie staining of SDS-PAGE (FIG. 6C): CMVtt830, eIL5-C-His, eIL5-C-His-CMVtt830 VLP were separated by SDS-PAGE. Subsequently gel was stained with Coomassie-Blue (0.025% Coomassie Brilliant BlueR-250, 40% methanol, 10% acetic acid) and de-stained with destainer (40% methanol, 10% acetic acid).

Western blot staining with anti-His antibody (FIG. 6D): CMV-tt830, eIL5-C-His, eIL5-C-His-CMVtt830 VLP were separated by SDS-PAGE and electroblotted onto a nitrocellulose membrane. The membrane was blocked for 1 h with 5% (w/v) BSA powder in PBST, then incubated with 10 ml of 1:1000 diluted anti-His antibody (monoclonal anti-His Tag antibody HRPO conjugate, Novagen CatNo. 71840) in 1% BSA (w/v) powder in PBST. The membrane was washed with PBST for 15 minutes and then developed with ECL (Amersham Pharmacia, Sweden) and exposed to Photographic film.

The covalent chemical coupling of eIL5-C-His to the CMVtt830 VLP was assessed by SDS-PAGE and Western blot analyses. Coomassie blue stained gels of the coupling reaction demonstrated the appearance of bands with molecular weights corresponding to those predicted for equine IL5-C-His covalently linked to CMV-tt830(FIG. 6C). Furthermore, Western blot analyses showed co-localization of these bands when stained with anti-His antibody (FIG. 6D).

C. Immunization Protocol

Horses, eIL-5-C-His-Qβ VLP.

In order to generate self-reactive antibodies to equine IL-5, horses were injected subcutaneously on day 0, 21, and 42 with 300 μg of eIL5-C-His-Qβ VLP in 1,000 μl of PBS mixed 30 min prior to injection with 300 µl alum. When indicated, a booster was given on day 124. Alternatively horses have been injected subcutaneously on day 0, 28, 56, and 84 with 300 µg of eIL5-C-His-Qβ VLP in 1,000 µl of PBS without presence of adjuvants. For follow-up on second year treatment, horses were subcutaneously boosted twice in a four-weekly interval with 300 µg of eIL5-C-His-Qβ VLP in 1,000 µl of PBS without presence of adjuvants. Horses were bled prior to immunization and at least on day 42, day 56 of the immunization protocol and various additional time points post day 56. Sera were analyzed by ELISA. Sera were analyzed by ELISA.

Horses, eIL-5-C-His-CMVtt830.

In order to generate self-reactive antibodies to equine IL-5, horses were injected subcutaneously on day 0, 28, 56, 84 and day 126 with 400 µg of eIL5-C-His-CMVtt830 VLP in 1,000 µl of PBS without presence of adjuvants. Horses were bled prior to immunization and at least either on day 56 and 84 of the immunization protocol and various additional time points post day 84. Sera were analyzed by ELISA. Sera were analyzed by ELISA.

D. Sera Analysis by ELISA

Maxisorp 96 well ELISA plates (Nunc) were coated over night with 50 µl purified eIL-5-C-His, Qβ or purified CMVtt830 (5 µg/ml). Plates were washed 3 times with PBST blocked with Superblock (Thermo Scientific) in PBS for 2 hours at room temperature. Then plates were washed 3 times with PBST and three-fold dilutions of horse sera were added in Superblock (Thermo Scientific) in PBS and incubated at room temperature for 2 h. The plates were subsequently washed 3 times with PBST and incubated with anti-equine IgG conjugated with HRP (dilution 1:2000) at room temperature for 30 min. The plates were again washed 4 times with PBS and 50 µl/well developing solution (TMB) were added. After approximately 2 minutes of reaction at room temperature the ELISA was stopped with 25 µl per well 5% $H_2SO_4$. Absorbance was measured at 450 nm on a Tecan M200 spectrophotometer (Tecan, Austria).

Pre-immune sera and various sera post immunization from horses vaccinated with eIL5-C-His-Qβ VLP were collected and analyzed by ELISA for antibodies against eIL-5-C-His (FIG. 7A) and antibodies against Qβ VLP (FIG. 7B). Pre-immune sera and various sear post immunization from eIL-5-C-His-CMVtt830 VLP vaccinated horses have been analyzed for antibodies against eIL-5-C-His (FIG. 7C) and antibodies against CMVtt830 (FIG. 7D). Horse sera were blotted as delta $OD_{50}$ ($\Delta OD_{50}$) values, which were calculated from OD450 values for each dilution subtracted by corresponding naïve serum dilution. The result of vaccination in horses shows that immunological tolerance towards the self-antigen IL-5 was overcome. Half maximal titer at peak of response was in the range between 1:1,000-1:50,000.

E. In Vivo Efficacy in Horses

Correlating Eosinophil Levels in Blood and IBH Disease Symptoms.

EDTA blood from 12 IBH affected Icelandic horses was taken and eosinophil levels were analyzed. Further disease symptom scoring was assessed during season, i.e. during the months from April to October. Levels of eosinophils in blood were correlated to average disease symptoms measure by lesion symptom scoring. Lesion symptom scoring was done according to Example 7. Indeed a positive correlation between number of eosinophils in blood of sick horses and IBH lesion intensity scores was found ($R^2$=0.9227, $p<0.0001$, n=12) (FIG. 7E) showing that the inventive compositions and their use in a method of immunizing horses affected with IBH are beneficial for the treatment of IBH.

Double-Blind Placebo Controlled Randomized Study IL-5-C-His-Qβ.

Ten IBH affected Icelandic horses were enclosed in a double-blind placebo controlled randomized study in order to assess effects of vaccination on disease symptoms and blood eosinophilia. In the IBH season previous to vaccination (April-October) a bi-weekly symptom scoring was assessed for all horses and blood eosinophilia was quantified beginning of August. Before the following IBH season started, six Icelandic horses were immunized with 300 µg eIL-5-C-His-Qβ and four Icelandic horses received placebo on day 0, 21 and 42 (February/March). The vaccine was administered in 1 ml PBS. All injections were administered in the presence of freshly (approx. 30 min before injection) premixed with 0.3 ml alum (Imject Alum, Thermo Scientific, CatNo. 77161). All horses receive a booster vaccination on day 124 and antibody titers and eosinophil counts were measured monthly from March until October. Furthermore, lesion scoring was evaluated bi-weekly. Moreover, health status as well as parasitic status of the horses was analyzed in March and October.

Follow-Up Study IL-5-C-His-Qβ.

Ten horses from double-blind placebo controlled randomized study using IL-5—C-His-Qβ have been followed-up in the following season 2016. The previously six vaccinated horses received two booster immunizations of 300 µg of eIL-5-C-His-Qβ in February and March with a four weeks interval. The previously four placebo horses received active immunization of 300 µg of eIL-5-C-His-Qβ on day 0, 28, 56, and 84. The vaccine for all horses was administered in 1 ml PBS without presence of adjuvants in the follow-up year. Antibody titers and eosinophil counts were measured monthly from January and March until October. Furthermore, lesion scoring was evaluated bi-weekly to monthly. Moreover, health status as well as parasitic status of the horses was analyzed in January and October. Lesion severity was followed from April until October. Timeline of antibody titer against Qβ (FIG. 7A) and eIL-5 (FIG. 7B) was followed over the whole season. The horses had been vaccinated by three injections starting in February in a three-week interval followed by a booster immunization approximately two months after the last injection. The established antibody titers against eIL-5 in the active horses varied with a huge magnitude at the beginning, however, were less variable in terms of titer above effectiveness after the boost (FIG. 7B).

For the subsequent follow-up season, the study was unblinded and continued as half cross-over study, all horses received vaccine. Detailed study regimen as follows: before the subsequent IBH season started all placebo horses were immunized four times in four-weekly intervals starting in January and all vaccine horses from previous season received two booster immunizations in a 4 weekly interval starting in February. In the follow-up year all vaccinations were administered without the presence of alum.

Lesion scores comparing vaccinated horses with placebo horses from April until September or October, respectively, in pre-evaluation year 2014, first year treatment 2015 (double-blind placebo controlled randomized study), and year $2^{nd}$ year treatment 2016 (follow-up study). More than 80% of vaccinated horses (V1: first year study and V2: second year study) achieved a 50% and higher improvement in lesion scores during treatment year(s). Even almost 20% of vaccinated horses (V1: first year study and V2: first and second year study) achieved a 75% and higher improvement in lesion scores during treatment year(s) (FIG. 7F). In the placebo group no horse reached 50% or 75% improvement in lesion scores (FIG. 7F). Therefore, eIL-5-C-His-Qβ vaccine had beneficial effects on lesion severity and thus therapeutically improved disease symptoms.

Double-Blind Placebo Controlled Randomized Study IL-5-C-His-CMVtt830.

Thirty-four IBH affected Icelandic horses were enclosed in a double-blind placebo controlled randomized study in order to assess effects of vaccination on disease symptoms and blood eosinophilia. In the IBH season previous to vaccination (April-October 2015) a monthly symptom scoring was assessed for all horses and blood eosinophilia was quantified at one time point during season. Before the following IBH season started, eighteen Icelandic horses were immunized with 400 µg eIL-5-C-His-CMVtt830 and fifteen Icelandic horses received placebo on day 0, 28, 56 and 84 (January until April 2016). The vaccine was administered in 1 ml PBS without presence of adjuvants. All horses received a booster vaccination on day 126 and antibody titers, eosinophil counts and lesion scores were measured monthly from January and March until October 2016.

Lesion scores comparing vaccinated horses with placebo horses from April until September or October in pre-evaluation year 2015 and treatment year 2016. Clinical scores of eIL-5-C-His-CMVtt830 vaccinated horses (black continuous line) were found to be strongly decreased when comparing to pre-evaluation season (black dotted line) and also to placebo-treated horses (grey lines) from the same season (grey continuous line) (FIG. 7G). Reduction of lesion scores between treatment year and pre-evaluation year in eIL-5-C-His-CMVtt830 vaccinated horses was found to be statistically significantly larger when comparing to placebo-treated horses. Moreover, 47% and 16% of vaccinated horses achieved a 50% (and higher) and 75% (and higher) improvement in lesion scores during treatment year, respectively (FIG. 7H). In the placebo group no horse reached 75% reduction, and only 7% reached a reduction of 50% improvement in lesion scores (FIG. 7H). Therefore, IL-5—C-His-CMVtt830 vaccine had beneficial effects on lesion severity and thus therapeutically improved disease symptoms.

Example 7

Dermatitis Symptom Lesion Scoring

For allergic dermatitis symptom scoring, the location (tail, mane, belly, flank, face, ear, leg, and the like) where lesions occur are recorded. Each location is divided into 3 parts: up, middle, down. Further according to the number of lesions, each location is classified into light and strong. Dependent on how many parts are affected (up/middle/down) and how many lesions per location are found (light/strong), 1 to 4 points can be scored (1 point=one part affected, lesion light; 4 points=all three parts affected, lesion strong).

Moreover, these locations are classified for 6 further properties: size (diameter), blood, hair loss, scales, crust, and lichenification/swelling. For all these properties also 1 to 4 points can be scored. Size is divided into <0.5 cm (1 point), 0.5≥x≥1 cm (2 points), 1≥x≥2 cm (3 points), and ≥2 cm (4 points). Blood is divided into intact epidermis (1 point), mild (2 points), moderate (3 points), and severe (4 points). Hair loss is divided into mild (1 point), moderate (2 points), severe (3 points), and no hair (4 points). Scales is divided into none (1 point), tiny, few (2 points), moderate, mid-size (3 points), and many, big (4 points). Crust is divided into none (1 point), tiny (2 points), half (3 points), and total (4 points). Lichenification and/or swelling is divided into none (1 point), mild (2 points), moderate (3 points), and severe (4 points).

Additionally, if sheath or udder is swollen, minimally 5 or maximally 20 points can be scored: grade 1 (5 points), grade 2 (10 points), grade 3 (15 points), and grade 4 (20 points).

Finally all points are added up and are the allergic dermatitis symptom score.

Example 8

Pruritus Scoring

Assessment of pruritus scoring during the time of the visit of each horse. Light, moderate and severe scratching at different locations of the body are scored. Each part of the body is scored separately. Furthermore, intensity of head shaking, also distinguished in light, moderate and severe, is scored. Additionally, unresting behavior overall is judged, also distinguished in light, moderate and severe. Light gives one point, moderate two points, and severe three points. All points are added up and give the pruritic score.

Example 9

Mouse Allergic Dermatitis Model, Vaccination of Mice, and Analysis of Antibody Titer, Local IL-31 mRNA Expression in the Skin, Anti-Allergen IgE and IgG Level, and Ear Swelling Upon Allergen Challenge on the Skin A. Mouse Allergic Dermatitis Model (Modified Atopic March Model)

Mice were sensitized against ovalbumin (Ova), a model allergen. Ova was chosen in order to show independence of *Culicoides* allergen and thus independence of IBH, highlighting a general allergic pruritus phenomenon. In order that mice develop an allergic dermatitis, mice were first challenged once intraperitoneally (i.p.) with 1 µg Ova (Sigma Aldrich) in 10 mg/ml alum (Thermo Scientific) in PBS on day 0 and then subsequently challenged topically by the epicutaneous (e.c.) route with 200 µg Ova in 2 nmol MC903 (Calcipotriol) on tape stripped skin right ear. The topical skin sensitization was done in on days 0 (=day 21 of vaccination protocol), 2, 4, 6, 8, and 10. Later the mice were challenged via the skin on the left ear on day 17, 18, 19, and 20 by 200 µg Ova. Dermatitis and pruritus development were followed subsequently, scored according to Example 7 and 8 and ear swelling of challenged left ear was quantified by measurement of ear thickness. Moreover, IL-31 mRNA was quantified by qPCR in the challenged ear on day 22. Also, allergic condition towards ova was quantified by anti-ova IgG and IgE antibody levels in serum on day 22. Five groups of mice were included in the allergic dermatitis experiment, n=6 mice: group 1 was vaccinated with mIL-31-C-His-CMV and received an ova challenge on the left ear; group 2 was vaccinated with CMVtt830 VLP and received an ova challenge on the left ear; group 3 was vaccinated with mIL-5-C-His-Qβ & mIL-31-C-His-CMVtt830 combination and received an ova challenge on the left ear; and groups 4 was vaccinated using CMVtt830 VLP, but received a PBS control challenge on the left ear.

B. Vaccination of Mice

In order to generate antibodies against murine IL-5 and/or IL-31 in mice, C57BL/6 or BALB/c mice were injected subcutaneously or intravenously on day 0, 14 and 28 with 25 or 50 µg of mIL-5-C-His-Qβ VLP and mIL-31-C-His-CMVtt830 in 100 µl PBS or 20 mM Na$_2$PO$_4$/2 mM EDTA, pH 7.5, respectively. The composition mIL-5-C-His-Qβ VLP was prepared in analogous manner as described in Zou, Vaccine 28 (2010) 3192-3200 and the eIL-5 and eIL-31 counterparts described herein. The composition mIL-31-C-His-CMVtt830 comprising mIL-31 (SEQ ID NO: 28) and mIL-31-C-His (SEQ ID NO:29), respectively, were prepared in analogous manner as described herein for the eIL-5 and eIL-31 counterparts. Mice were bled prior to immunization and at day 41 of the immunization protocol. Sera were analyzed by ELISA.

C. Antibody Titer Analysis

Maxisorp 96 well ELISA plates (Nunc) were coated over night with 50 µl purified mIL-5-C-His or mIL-31-C-His (10 µg/ml). Plates were washed 3 times with PBST blocked with Superblock (Thermo Scientific) for 2 hours at room temperature. Then plates were washed 3 times with PBST and three-fold dilutions of mouse or horse sera were added in Superblock and incubated at room temperature for 2 h. The plates were subsequently washed 3 times with PBST and incubated with anti-mouse IgG or anti-equine IgG conjugated with HRP (dilution 1:2000) at room temperature for 30 min. The plates were again washed 4 times with PBS and 50 µl/well developing solution (TMB) were added. After approximately 2 minutes of reaction at room temperature the ELISA was stopped with 25 µl per well 5% H$_2$SO$_4$. Absorbance was measured at 450 nm on a Tecan M200 or Tecan Spark spectrophotometer (Tecan, Austria).

Preimmune sera and day 41 sera from mice vaccinated with mIL-5-C-His-Qβ and/or mIL-31-C-His-CMVtt830 were collected and analyzed by ELISA. Mouse sera was blotted as delta OD$_{50}$ (ΔOD$_{50}$) values. The result of vaccination in mice shows that immunological tolerance towards the self-antigens IL-5 and IL-31 was overcome (FIG. 8A and FIG. 8B). Mice vaccinated with mIL-5-C-His-Qβ established anti-IL-5 antibody titers of approximately 1:2000 (FIG. 8A, black circles). Mice vaccinated with mIL-31-C-His-CMVtt830 established anti-IL-5 antibody titers of approximately 1:300 (FIG. 8A, grey circles), and mice vaccinated against combination using mIL-5-C-His-Qβ/mIL-31-C-His-CMVtt830 combination vaccination established anti-IL-5 antibody titers of approximately 1:1000 (FIG. 8B, black circles) and anti-IL-31 antibody titers of approximately 1:200 (FIG. 8B, grey circles). Half maximal titer at peak of response were approximately 1:1,000.

D. RNA Isolation and cDNA Transcription of Challenged Ears

Ear skin biopsies were stored in Trizol Reagent (Life Technologies) at −80° C. and total RNA was isolated using High Pure RNA Isolation Kit (Roche) including DNase I treatment and inactivation. RNA was transcribed into cDNA using Reverse Transcription System (Promega) and mouse IL-31 mRNA level and housekeeping βactin gene were amplified by PCR and quantified by qPCR.

E. Mouse IL-31 & βActin qPCR

Amplification of mouse IL-31 (mIL-31) mouse βactin (mβactin) in skin biopsies using the gene-specific RT$^2$ qPCR Primer Assay (Qiagen) for mIL-31 and the gene-specific primers for mβactin (forward primer: GGCTGTAT-TCCCCTCCATCG—SEQ ID NO:30; reverse primer: CCAGTTGGTAACAATGCCATGT—SEQ ID NO:31). The PCR was done using FastStart Universal SYBR Green Master (Roche).

Murine IL-31 mRNA expression levels is shown in ova challenged ears of ova allergic mice vaccinated with either mIL-31-C-His-CMV (group 1), CMVtt830 VLP (group 2), mIL-5-C-His-Qβ & mIL-31-C-His-CMVtt830 combination (group 3). A second CMVtt830 VLP vaccinated group 4 was challenged with PBS control instead of ova. The ova challenged groups of mice, which have been vaccinated against mIL-31, either group 1 vaccinated using mIL-31-C-His-CMVtt830 alone or group 3 vaccinated using mIL-5-Qβ & mIL-31-C-His-CMVtt830 combination; showed low mIL-31 mRNA levels in ova challenged ears; comparably mIL-31 mRNA levels of CMVtt830 VLP vaccinated group 4 challenged with PBS control. In contrast, group 2 CMVtt830 VLP vaccinated mice with ova challenged ears, showed increased mIL-31 mRNA expression. Thus, vaccination against mIL-31 efficiently reduced mIL-31 expression upon ova allergen challenge in the skin (FIG. 8C).

E. Anti-Allergen (Ova) IgE and IgG Level

IgE:

Maxisorp 96 well ELISA plates (Nunc) were coated over night 50 µl with anti-mouse IgE monoclonal antibody (3 µg/ml). Plates were washed 3 times with PBST blocked with 2.5% milk powder in PBS for 2 hours at room temperature. Then plates were washed 3 times with PBST and three-fold dilutions of mouse sera were added in Superblock and incubated at room temperature for 2 h. The plates were subsequently washed 3 times with PBST and incubated biotinylated Ova (dilution 1:250) at room temperature for 2 hours at room temperature. The plates were subsequently washed 3 times with PBST and Streptavidin-HRP (Biolegend) was added. The plates were again washed 4 times with PBS and 50 µl/well developing solution (TMB) were added. After approximately 2 minutes of reaction at room temperature the ELISA was stopped with 25 µl per well 5% H$_2$SO$_4$. Absorbance was measured at 450 nm on a Tecan M200 or Tecan Spark spectrophotometer (Tecan, Austria).

IgG:

Maxisorp 96 well ELISA plates (Nunc) were coated over night with 50 µl purified Ova (10 µg/ml). Plates were washed 3 times with PBST blocked with Superblock (Thermo Scientific) for 2 hours at room temperature. Then plates were washed 3 times with PBST and three-fold dilutions of mouse sera were added in Superblock and incubated at room temperature for 2 h. The plates were subsequently washed 3 times with PBST and incubated with anti-murine IgG conjugated with HRP (dilution 1:2000) at room temperature for 30 min. The plates were again washed 4 times with PBS and 50 µl/well developing solution (TMB) were added. After approximately 2 minutes of reaction at room temperature the ELISA was stopped with 25 µl per well 5% H$_2$SO$_4$. Absorbance was measured at 450 nm on a Tecan M200 or Tecan Spark spectrophotometer (Tecan, Austria).

Preimmune sera and day 22 sera (of allergic dermatitis time line, experimental endpoint) from ova sensitized mice additionally vaccinated with mIL-31-C-His-CMVtt830 (group 1), CMVtt830 VLP (group 2 and 4), or mIL-5-C-His-Qβ & mIL-31-C-His-CMVtt830 combination (group 3) were collected and analyzed by ELISA. Groups 1-3 have been challenged with ova allergen, group 4 was challenged with PBS on the challenge ear. Anti-ova IgG (FIG. 8D) and anti-ova IgE (FIG. 8E) antibody titers show allergen sensitization to ova allergen of the different groups mice. All groups of mice developed an allergic immune response towards ova (FIGS. 8D & 8E).

F. Ear Swelling Upon Ova Allergen Challenge of Ear

Ova allergen challenge on the left ear was done following the ova sensitization using an i.p injection and skin sensitization on the right ear of the mice. Ear swelling was quantified by measuring ear thickness on day 17, 18, 19, 20, 21, and 22. Percentage of increase of ear thickness compared to day 17 (first day of challenge) is shown (FIG. 8F). Group 2 vaccinated against CMVtt830 VLP receiving ova challenge showed a continuous increase of ear thickness on the challenged ear (FIG. 8F, triangle). The mIL-31-C-His-CMVtt830 alone (FIG. 8F, filled circle), and mIL-5C-His-Qβ & mIL-31-C-His-CMVtt830 combination (FIG. 8F, square) vaccinated groups that received an ova challenge were protected from an increase in ear thickness, and showed comparable values to CMVtt830 VLP (dotted line) vaccinated group that received a PBS control challenge. Thus vaccination against either IL-31 or IL-5 or a combination of both protected mice from ear swelling upon allergen challenge when using the model allergen ova in a skin sensitization and challenge model.

The invention claimed is:

1. A method of treatment of a condition or disorder selected from a pruritic condition or an allergic condition of an equine mammal, wherein said method comprises administering an effective amount of a composition to said equine mammal, wherein said composition comprises:
   (a) a core particle with at least one first attachment site; and
   (b) at least one antigen with at least one second attachment site, wherein said at least one antigen is an equine Interleukin-31 antigen (eIL-31 antigen), wherein said eIL-31 antigen comprises a protein with the amino acid sequence selected from SEQ ID NO:1 or a protein with an amino acid sequence of at least 90% sequence identity with SEQ ID NO:1;
   wherein (a) and (b) are linked through said at least one first and said at least one second attachment site via at least one non-peptide covalent bond, and wherein said condition or disorder is not insect bite hypersensitivity (IBH) of an equine mammal.

2. The method according to claim 1, wherein said composition further comprises:
   (c) a second core particle with at least one first attachment site; and
   (d) at least one second antigen with at least one second attachment site, wherein said at least one second antigen is an equine Interleukin-5 antigen (eIL-5 antigen), wherein said eIL-5 antigen comprises a protein with the amino acid sequence selected from SEQ ID NO:6 or a protein with an amino acid sequence of at least 90% sequence identity with SEQ ID NO:6;
   wherein (c) and (d) are linked through said at least one first and said at least one second attachment site via at least one non-peptide covalent bond.

3. The method according to claim 1, wherein said eIL-31 antigen comprises a protein with the amino acid sequence selected from SEQ ID NO:1, SEQ ID NO:2, SEQ ID NO:3, SEQ ID NO:4, SEQ ID NO:5.

4. The method according to claim 2, wherein said eIL-5 antigen comprises a protein with the amino acid sequence selected from SEQ ID NO:6, SEQ ID NO:7, SEQ ID NO:8, SEQ ID NO:9 and SEQ ID NO:10.

5. The method according to claim 1, wherein said core particle is a virus-like particle (VLP).

6. The method according to claim 5, wherein said VLP is derived from a plant virus or is a VLP of an RNA bacteriophage.

7. The method according to claim 5, wherein said VLP is a modified VLP comprising at least one modified VLP polypeptide, wherein said modified VLP polypeptide comprises:
(a) a VLP polypeptide, and
(b) a T helper cell epitope,
wherein said VLP polypeptide comprises,
(i) an amino acid sequence of a coat protein of a virus, or
(ii) a mutated amino acid sequence, wherein the amino acid sequence to be mutated is an amino acid sequence of said coat protein of a virus, and wherein said mutated amino acid sequence and said coat protein of a virus share a sequence identity of at least 90%.

8. The method according to claim 5, wherein said VLP is a modified VLP of cucumber mosaic virus (CMV), wherein said modified VLP of CMV comprises at least one modified CMV polypeptide, wherein said modified CMV polypeptide comprises:
(a) a CMV polypeptide, and
(b) a T helper cell epitope; and
wherein said CMV polypeptide comprises:
(i) an amino acid sequence of a coat protein of CMV; or
(ii) a mutated amino acid sequence, wherein the amino acid sequence to be mutated is an amino acid sequence of a coat protein of CMV, and wherein said mutated amino acid sequence and said coat protein of CMV share a sequence identity of at least 90%.

9. The method according to claim 8, wherein said T helper cell epitope replaces a N-terminal region of said CMV polypeptide, and wherein said N-terminal region of said CMV polypeptide is amino acids 2-12 of SEQ ID NO:15.

10. The method according to claim 8, wherein said CMV polypeptide comprises an amino acid sequence of a coat protein of CMV, wherein said amino acid sequence comprises SEQ ID NO:15 or an amino acid sequence having a sequence identity of at least 95% of SEQ ID NO:15; and also wherein said amino acid sequence comprises SEQ ID NO:27, and wherein said T helper cell epitope replaces the N-terminal region of said CMV polypeptide, and wherein said replaced N-terminal region of said CMV polypeptide consists of 11 to 13 consecutive amino acids.

11. The method according to claim 8, wherein said modified CMV polypeptide comprises an amino acid sequence of SEQ ID NO:20 or SEQ ID NO:21.

12. The method according to claim 1, wherein said pruritic condition or said allergic condition is selected from atopic dermatitis, eczema, psoriasis, scleroderma, pruritus, allergic dermatitis, bacterial folliculitis, dermatophytosis, recurrent urticaria, heaves, inflammatory airway disease, recurrent airway obstruction, airway hyper-responsiveness, chronic obstruction pulmonary disease, and inflammatory processes resulting from autoimmunity.

13. The method according to claim 1, wherein said administration of said composition reduces at least one parameter or symptom associated with said pruritic condition or said allergic condition as compared to said at least one parameter or symptom associated with said pruritic condition or said allergic condition before said administration.

14. The method according to claim 13, wherein said at least one parameter or symptom associated with said pruritic condition or said allergic condition is the level or severity grade of skin lesions or the level of pruritus.

15. The method according to claim 14, wherein said reduction of said level or severity grade of skin lesions is determined by a symptom lesion scoring test and said reduction of said level of pruritus is determined by a pruritus scoring test.

16. The method according to claim 13, wherein said at least one parameter or symptom associated with said pruritic condition or said allergic condition is the level of pruritus, and wherein said reduction of said level of pruritus is determined by the reduction of scratching at least one location of the body of said equine mammal.

* * * * *